United States Patent
Bass et al.

(10) Patent No.: US 11,957,739 B2
(45) Date of Patent: Apr. 16, 2024

(54) COMPOSITIONS AND METHODS FOR TREATING CANCER USING RHOA DOMINANT NEGATIVE FORMS

(71) Applicant: Dana-Farber Cancer Institute, Inc., Boston, MA (US)

(72) Inventors: Adam Bass, Somerville, MA (US); Haisheng Zhang, Newton, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 993 days.

(21) Appl. No.: 16/761,540

(22) PCT Filed: Nov. 5, 2018

(86) PCT No.: PCT/US2018/059188
§ 371 (c)(1),
(2) Date: May 5, 2020

(87) PCT Pub. No.: WO2019/094326
PCT Pub. Date: May 16, 2019

(65) Prior Publication Data
US 2020/0261550 A1  Aug. 20, 2020

Related U.S. Application Data

(60) Provisional application No. 62/583,166, filed on Nov. 8, 2017.

(51) Int. Cl.
| | | |
|---|---|---|
| A61K 38/00 | (2006.01) | |
| A61K 38/46 | (2006.01) | |
| A61K 39/00 | (2006.01) | |
| G01N 33/574 | (2006.01) | |
| A61K 45/06 | (2006.01) | |
| A61K 48/00 | (2006.01) | |

(52) U.S. Cl.
CPC .......... *A61K 38/46* (2013.01); *A61K 39/0011* (2013.01); *G01N 33/574* (2013.01); *A61K 39/001164* (2018.08); *A61K 45/06* (2013.01); *A61K 48/00* (2013.01)

(58) Field of Classification Search
CPC ........ A61K 39/0011; A61K 39/001164; A61K 48/00; G01N 33/574; A61P 35/00
See application file for complete search history.

(56) References Cited

U.S. PATENT DOCUMENTS

| | | | | |
|---|---|---|---|---|
| 2001/0044414 A1* | 11/2001 | Clark | .................. | G01N 33/574 435/6.14 |
| 2005/0209147 A1* | 9/2005 | Laudanna | .............. | A61K 47/64 514/1.2 |
| 2006/0105374 A1 | 5/2006 | Sebti | | |
| 2007/0161060 A1 | 7/2007 | Anderson et al. | | |
| 2009/0220985 A1 | 9/2009 | Peck et al. | | |
| 2016/0159905 A1* | 6/2016 | Abdiche | ............ | A61K 39/3955 435/254.2 |
| 2020/0261550 A1 | 8/2020 | Bass et al. | | |

FOREIGN PATENT DOCUMENTS

| | | | | |
|---|---|---|---|---|
| WO | WO-2009/076966 A2 | 6/2009 | | |
| WO | WO-2009089040 A1 * | 7/2009 | ......... | A61K 48/0075 |
| WO | WO-2019/094326 A1 | 5/2019 | | |

OTHER PUBLICATIONS

Skolnick et al. (Trends in Biotech., 18(1):34-39, 2000) (Year: 2000).*
Frixen et al Journal of Cell Biology vol. 113(1):173 (1991). (Year: 1991).*
Sakata-Yanagimoto et al Nature Genetics vol. 46 p. 171 (2014) (Year: 2014).*
Guilford et al Nature vol. 392 p. 402 (1998) (Year: 1998).*
Bhowmick et al., "Transforming Growth Factor-b1 Mediates Epithelial to Mesenchymal Transdifferentiation through a RhoAdependent Mechanism," Molecular Biology of the Cell, 12(1):27-36 (2001).
International Search Report and Written Opinion for International Application No. PCT/US2018/059188 dated Feb. 14, 2019.
Shankar et al., "Actin Cytoskeleton Regulation of Epithelial Mesenchymal Transition in Metastatic Cancer Cells," PLoS One, 10(3):1-12 (2015).
Zhou et al., "RhoA Mutations Identified in Diffuse Gastric Cancer," Cancer Cell, 26(1):9-11 (2014).
Cancer Genome Atlas Research Network, "Comprehensive molecular characterization of gastric adenocarcinoma." *Nature* 513.7517: 202 (2014).
Extended European Search Report for EP Application PCT/US2018/059188 dated Jul. 21, 2021.
Fan, Daiming "Frontier of tumor research vol. 3", *Xi'an Jiaotong University Press*, pp. 114-115 (2003).
Sun, Xiaojie., "Molecular Diagnosis and Targeted Therapy of Tumor", *Second Military Medical University Press*, p. 129 (2009).
Sutter et al., "Gene therapy for gastric cancer: is it promising?", *World Journal of Gastroenterology* 12.3: 380 (2006).

* cited by examiner

*Primary Examiner* — Sheela J. Huff
(74) *Attorney, Agent, or Firm* — Foley Hoag LLP

(57) ABSTRACT

The present invention provides compositions and methods for treating cancers with reduced or absent CDH1 using a RHOA dominant negative polypeptide or biologically active fragment thereof, and/or a nucleic acid encoding a RHOA dominant negative polypeptide or biologically active fragment thereof.

14 Claims, 4 Drawing Sheets
Specification includes a Sequence Listing.

COMPOSITIONS AND METHODS FOR TREATING CANCER USING RHOA DOMINANT NEGATIVE FORMS

CROSS-REFERENCE TO RELATED APPLICATION

This application is the U.S. national phase of International Patent Application No. PCT/US2018/059188, filed on 5 Nov. 2018, which claims the benefit of U.S. Provisional Application Ser. No. 62/583,166, filed on 8 Nov. 2017; the entire contents of each of said applications are incorporated herein in their entirety by this reference.

SEQUENCE LISTING

The present specification makes reference to a Sequence Listing (submitted electronically as a .txt file named "DFS-19801_Sequence_Listing" on May 5, 2020). The .txt file was generated on Dec. 5, 2018 and is 12,543 bytes in size. The entire contents of the Sequence Listing are herein incorporated by reference.

BACKGROUND OF THE INVENTION

Gastric cancer is the third leading cause of cancer mortality worldwide (Sutter et al. (2006) *World J. Gastroenterol.* 12:380-387; Zhou et al. (2014) *Cancer Cell* 16:9-11; Cancer Genome Atlas Research Network (2014) *Nature* 513:202-209). Although gastric carcinoma has marked heterogeneity, the two most salient subtypes are intestinal gastric cancer (IGC) and diffuse gastric cancer (DGC). DGC owes its name to its characteristic lack of cellular cohesion, invasion throughout the stroma, and poor cellular differentiation (often with a signet-ring cell morphology). Families with a hereditary form of DGC carry a mutation in CDH1, which encodes the cellular adhesion protein E-Cadherin (Guilford et al. (1998) *Nature* 392:402-405). Beyond hereditary DGC, the vastly more common sporadic form of DGC has also been associated with E-cadherin loss, through either somatic mutation or promoter hypermethylation. DGC initiation typically follows loss of tumor suppressor CDH1. EMT cancers have similar features with the E-cadherin loss diffuse gastric cancer.

RHOA mutations were identified recurrently within DGC, which implicates RHOA as a novel candidate driver of DGC. RhoA is a member of the Rho family of small GTPase-Ras-like proteins that act as an intermediary between cell surface receptors and different intracellular signaling proteins. Similar to other GTPases, RhoA cycles between an inactive, GDP-bound configuration and an active GTP-bound configuration that interacts with downstream effectors, such as ROCK, that impact the structure and dynamics of the actin cytoskeleton, cell migration, cytokinesis, and cell cycle. RhoA overexpression has been observed in various cancers, and RhoA activity has been implicated in tumorigenesis and tumor cell invasion (Karlsson et al. (2009) *Biochim Biophys Acta.* 1796:91-98). It remains to be clarified, however, whether RHOA mutations merely attenuate physiologic RhoA activity or, alternatively, if these mutations result in gain of function.

Thus, gastric cancer, as well as other epithelial/mesenchyma transition (EMT) cancers, characterized by reduced and/or absent CDH1 expression are prone to early invasion and metastasis, and lack effective molecularly targeted therapies. Accordingly, a great need in the art exists to identify new therapeutic targets for EMT cancers like DGC.

SUMMARY OF THE INVENTION

The present invention is based in part on the discovery that small GTPase RHOA dominant negative forms (e.g., RHOA T19N, RHOA G17E, or RHOA G17V) modulate hyperproliferation of cancer cells having reduced and/or absent CDH1 expression, such as in CDH1-null cancer cells, whereas cancer cells wherein CDH1 expression is intact are spared.

In one aspect, a method of treating a subject afflicted with cancer that has a reduced level of CDH1 is provided, the method comprising administering to the subject a therapeutically effective amount of at least one agent selected from the group consisting of 1) a nucleic acid encoding a RHOA dominant negative polypeptide or biologically active fragment thereof and 2) a RHOA dominant negative polypeptide or biologically active fragment thereof.

Numerous embodiments are further provided that can be applied to any aspect of the present invention and/or combined with any other embodiment described herein. For example, in one embodiment, the cancer has a loss of CDH1 expression. In another embodiment, the cancer is undergoing or has undergone epithelal to mesenchymal transition (EMT). In still another embodiment, the cancer is selected from the group consisting of diffuse gastric cancer (DGC), lobular breast cancer, metastatic breast cancer, metastatic lung cancer, metastatic non small-cell lung cancer, colon cancer, pancreatic cancer, prostate cancer, brain cancer and melanoma. In yet another embodiment, the agent is selected from the group consisting of (i) a RHOA dominant negative polypeptide that is at least 80% identical over its full length to a polypeptide selected from the group consisting of SEQ ID NO: 1, 2, and 3, or a biologically active fragment thereof; and (ii) a nucleic acid sequence that encodes a RHOA dominant negative polypeptide or a biologically active fragment thereof of (i), wherein the nucleic acid sequence is at least 80% identical over its full length to a nucleic acid sequence selected from the group consisting of SEQ ID NO: 4, 5, 6, 7, 8, 9, 10, and 11, or a portion thereof that encodes the biologically active fragment. In another embodiment, the agent comprises a RHOA dominant negative polypeptide sequence of SEQ ID NO: 1, 2, or 3. In still another embodiment, the agent is a RHOA dominant negative polypeptide, or biologically active fragment thereof, and further comprises a heterologous polypeptide fused thereto. In yet another embodiment, the fused polypeptide has greater half-life and/or cell permeability than the corresponding unfused RHOA dominant negative polypeptide, or biologically active fragment thereof. In another embodiment, the heterologous polypeptide is an Fc domain and/or a cell permeable peptide. In still another embodiment, the agent is a nucleic acid that is comprised within an expression vector or a cell. In yet another embodiment, the method further comprises administering to the subject an immunotherapy and/or cancer therapy, optionally wherein the immunotherapy and/or cancer therapy is administered before, after, or concurrently with the agent. In another embodiment, the immunotherapy is cell-based. In still another embodiment, the immunotherapy comprises a cancer vaccine and/or virus. In yet another embodiment, the immunotherapy inhibits an immune checkpoint. In another embodiment, the immune checkpoint is selected from the group consisting of CTLA-4, PD-1, VISTA, B7-H2, B7-H3, PD-L1, B7-H4, B7-H6, ICOS, HVEM, PD-L2, CD160, gp49B, PIR-B, KIR family receptors, TIM-1, TIM-3, TIM-4, LAG-3, GITR, 4-IBB, OX-40, BTLA, SIRPalpha (CD47), CD48, 2B4 (CD244), B7.1, B7.2, ILT-2, ILT-4, TIGIT, HHLA2, butyrophilins, and A2aR. In still another embodiment, the cancer therapy is selected from the group consisting of radiation, a radiosensitizer, and a chemotherapy. In yet another embodiment, the agent reduces the number of viable or proliferating cells in the cancer, and/or reduces the volume or size of a tumor comprising the cancer cells. In another embodiment, the method further comprises administering to the subject at least one additional therapeutic agent or regimen for treating the cancer.

In another aspect, a method of reducing viability or proliferation of cancer cells which have a reduced level of CDH1 is provided, the method comprising contacting the cancer cells with at least one agent selected from the group consisting of 1) a nucleic acid encoding a RHOA dominant negative polypeptide or biologically active fragment thereof and 2) a RHOA dominant negative polypeptide or biologically active fragment thereof.

As described above, numerous embodiments are further provided that can be applied to any aspect of the present invention and/or combined with any other embodiment described herein. For example, in one embodiment, the cancer cells have a loss of CDH1 expression. In another embodiment, the cancer cells are undergoing or have undergone epithilal to mesenchymal transition (EMT). In still another embodiment, the cancer cells are obtained from a subject having a cancer selected from the group consisting of diffuse gastric cancer (DGC), lobular breast cancer, metastatic breast cancer, metastatic lung cancer, metastatic non small-cell lung cancer, colon cancer, pancreatic cancer, prostate cancer, brain cancer and melanoma. In yet another embodiment, the agent is selected from the group consisting of (i) a RHOA dominant negative polypeptide that is at least 80% identical over its full length to a polypeptide selected from the group consisting of SEQ ID NO: 1, 2, and 3, or a biologically active fragment thereof; and (ii) a nucleic acid sequence that encodes a RHOA dominant negative polypeptide or a biologically active fragment thereof of (i), wherein the nucleic acid sequence is at least 80% identical over its full length to a nucleic acid sequence selected from the group consisting of SEQ ID NO: 4, 5, 6, 7, 8, 9, 10, and 11, or a portion thereof that encodes the biologically active fragment. In another embodiment, the agent comprises a RHOA dominant negative polypeptide sequence of SEQ ID NO: 1, 2, or 3. In still another embodiment, the agent is a RHOA dominant negative polypeptide, or biologically active fragment thereof, and further comprises a heterologous polypeptide fused thereto. In yet another embodiment, the fused polypeptide has greater half-life and/or cell permeability than the corresponding unfused RHOA dominant negative polypeptide, or biologically active fragment thereof. In another embodiment, the heterologous polypeptide is an Fc domain and/or a cell permeable peptide. In still another embodiment, the agent is a nucleic acid that is comprised within an expression vector or a cell. In yet another embodiment, the method further comprises contacting the cancer cells with an immunotherapy and/or cancer therapy, optionally wherein the immunotherapy and/or cancer therapy is administered before, after, or concurrently with the agent. In another embodiment, the immunotherapy comprises a cancer vaccine and/or virus. In still another embodiment, the immunotherapy inhibits an immune checkpoint. In yet another embodiment, the immune checkpoint is selected from the group consisting of CTLA-4, PD-1, VISTA, B7-H2, B7-H3, PD-L1, B7-H4, B7-H6, ICOS, HVEM, PD-L2, CD160, gp49B, PIR-B, KIR family receptors, TIM-1, TIM-3, TIM-4, LAG-3, GITR, 4-IBB, OX-40, BTLA, SIRPalpha (CD47), CD48, 2B4 (CD244), B7.1, B7.2, ILT-2, ILT-4, TIGIT, HHLA2, butyrophilins, and A2aR. In another embodiment, the cancer therapy is selected from the group consisting of radiation, a radiosensitizer, and a chemotherapy.

In still another aspect, a method of assessing the efficacy of the agent of claim 1 for treating a cancer that has a reduced level of CDH1 in a subject is provided, the method comprising: a) detecting in a subject sample at a first point in time the number of viable and/or proliferating cancer cells; b) repeating step a) during at least one subsequent point in time after administration of the agent; and c) comparing number of viable and/or proliferating cancer cells detected in steps a) and b), wherein the absence of, or a significant decrease in number of viable and/or proliferating cancer cells in the subsequent sample as compared to the amount in the sample at the first point in time, indicates that the agent treats cancer in the subject.

As described above, numerous embodiments are further provided that can be applied to any aspect of the present invention and/or combined with any other embodiment described herein. For example, in one embodiment, between the first point in time and the subsequent point in time, the subject has undergone treatment, completed treatment, and/or is in remission for the cancer. In another embodiment, the first and/or at least one subsequent sample is selected from the group consisting of ex vivo and in vivo samples. In still another embodiment, the first and/or at least one subsequent sample is obtained from an animal model of the cancer. In yet another embodiment, the first and/or at least one subsequent sample is a portion of a single sample or pooled samples obtained from the subject. In another embodiment, the sample comprises cells, serum, peritumoral tissue, and/or intratumoral tissue obtained from the subject. In still another embodiment, the method further comprises determining responsiveness to the agent by measuring at least one criteria selected from the group consisting of clinical benefit rate, survival until mortality, pathological complete response, semi-quantitative measures of pathologic response, clinical complete remission, clinical partial remission, clinical stable disease, recurrence-free survival, metastasis free survival, disease free survival, circulating tumor cell decrease, circulating marker response, and RECIST criteria. In yet another embodiment, the agent is administered in a pharmaceutically acceptable formulation. In another embodiment, the step of administering or contacting occurs in vivo, ex vivo, or in vitro. In still another embodiment, the subject is an animal model of the cancer, optionally wherein the animal model is a mouse model. In yet another embodiment, the subject is a mammal. In another embodiment, the mammal is a mouse or human. In still another embodiment, the mammal is a human.

In yet another aspect, a cell-based assay for screening for agents that reduce viability or proliferation of a cancer cell with a reduced level of CDH1 is provided, the assay comprising:

a) contacting the cancer cell with a test agent selected from the group consisting of 1) a nucleic acid encoding a RHOA mutant, or biologically active fragment thereof and 2) a RHOA mutant polypeptide, or biologically active fragment thereof; and b) determining a reduced viability or proliferation of the cancer cell relative to a control, thereby identifying the test agent to reduce viability or proliferation of the cancer cell. In one embodiment, the control is a cancer cell not contacted with the test agent. In another embodiment, the control is a cancer cell contacted with an anti-cancer agent. In still another embodiment, the cancer cell is isolated from an animal model of cancer, or a human patient afflicted with cancer. In yet another embodiment, the step of contacting occurs in vivo, ex vivo, or in vitro.

Figure 1:
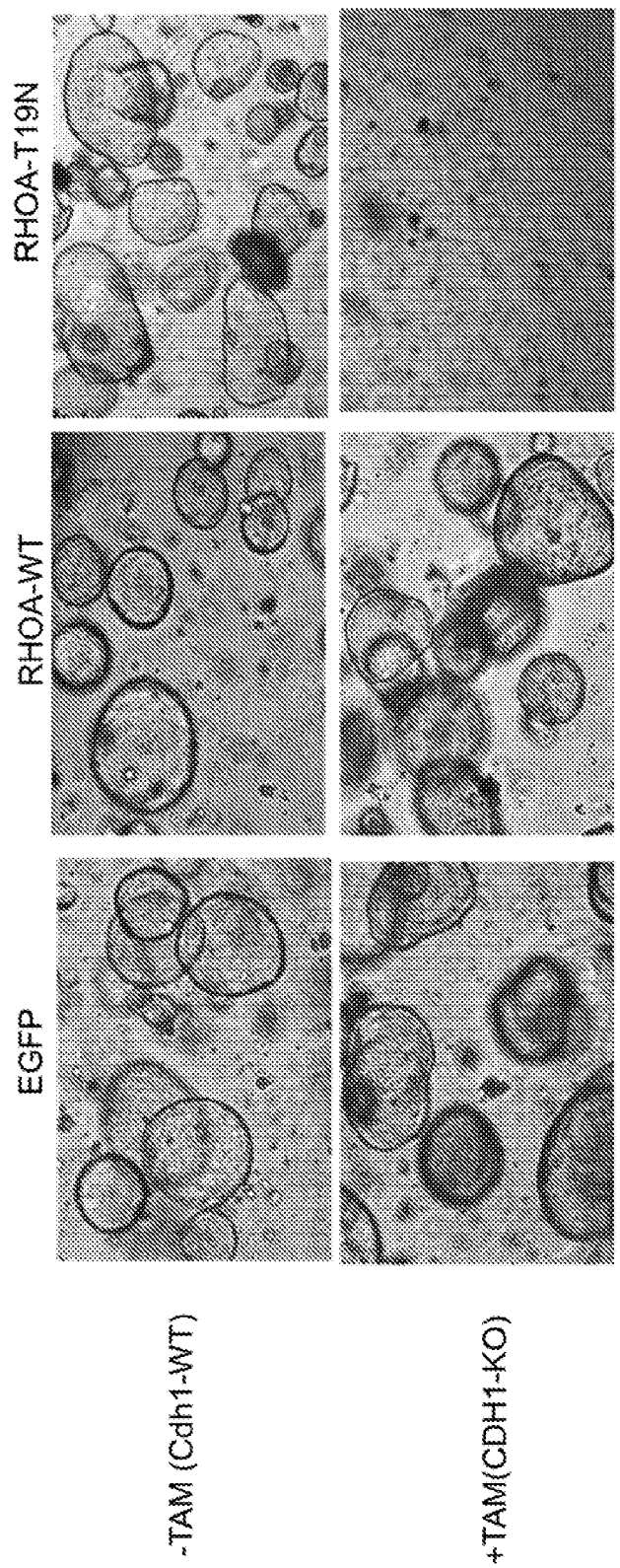
FIG. 1 shows that RHOA-T19N ectopic expression specifically kills CDH1-null stomach organoids. Mist1CreER, Cdh1$^{F/F}$ organoids were infected with plx307 lenti-EGFP/RHOA-WT/RHO-T19N virus, and the stably infected organoids were selected by adding puro for 1 week. The cells were then treated with or without tamoxifen to activate Cre to induce E-cadherin loss. The RHOA ectopic expression and E-Cadherin loss were validated both Western blot and Tomato/GFP color switch determinations.
Figure 2:
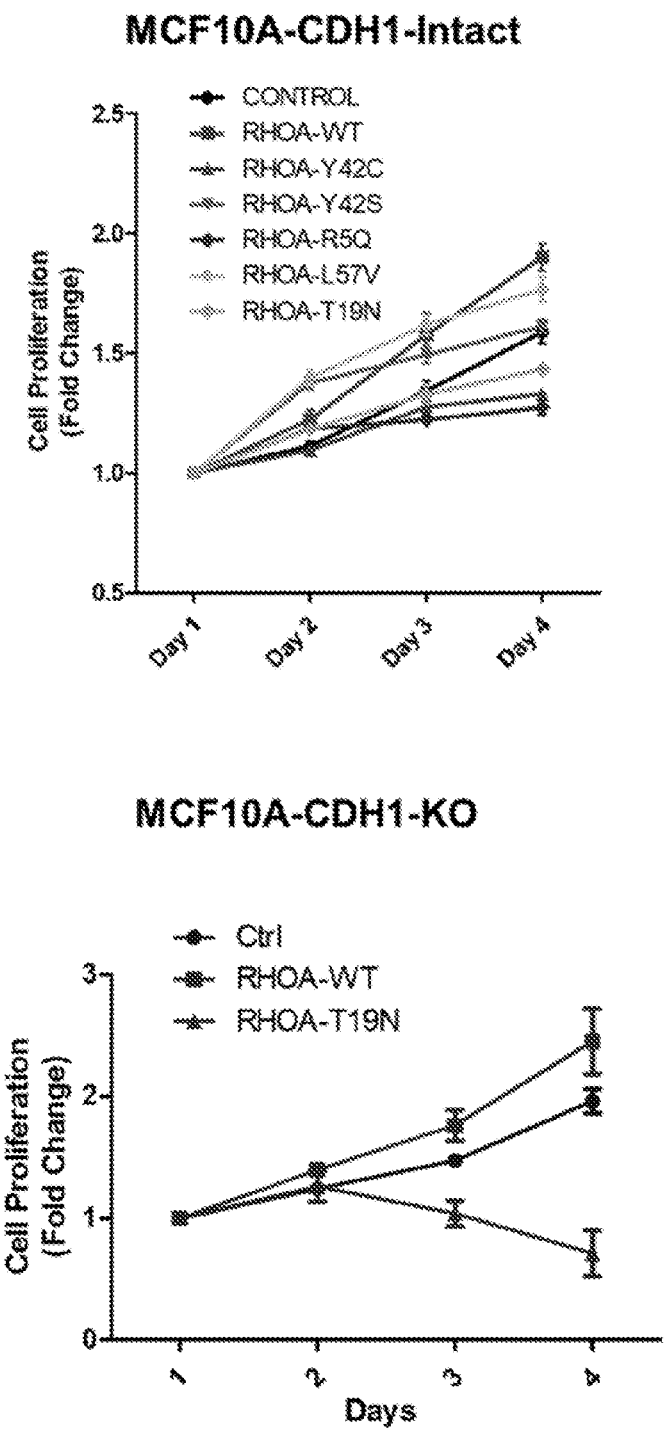
FIG. 2 shows that RHOA-T19N ectopic expression specifically kills CDH1-null breast epithelial MCF10A cells. Isogenic MCF10A-CDH1-intact cells were infected with different constitutive RHOA mutant virus and the stably infected cells were selected by adding puro for 1 week. The cells were then plated in 96-well plates for analysis using a cell titer glo assay. The MCF10A-CDH1-K0 cells were infected with different Dox-inducible RHOA mutant viruses and the stably-infected cells were selected by adding puro for 1 week. The cells were then plated in 96-well plates with Dox induction for cell titer glo assay analysis.
Figure 3:
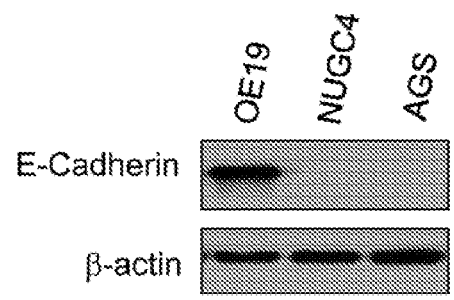
FIG. 3 shows that RHOA-T19N can significantly inhibit NUGC4 tumor growth. Diffuse gastric cancer (DGC) NUGC4 cells were confirmed for total E-cadherin loss by Western blot analysis. The cells were then stably infected with Dox-inducible lenti-RHOA virus using puro selection. Three million NUGC4 cells were injected into the flank of nude mice. After 2 weeks, regular food was changed to food with Dox in order to induce mutant RHOA expression. N=3 mice for each group. P<0.0001: Ctrl-VS-T19N.
Figure 3:
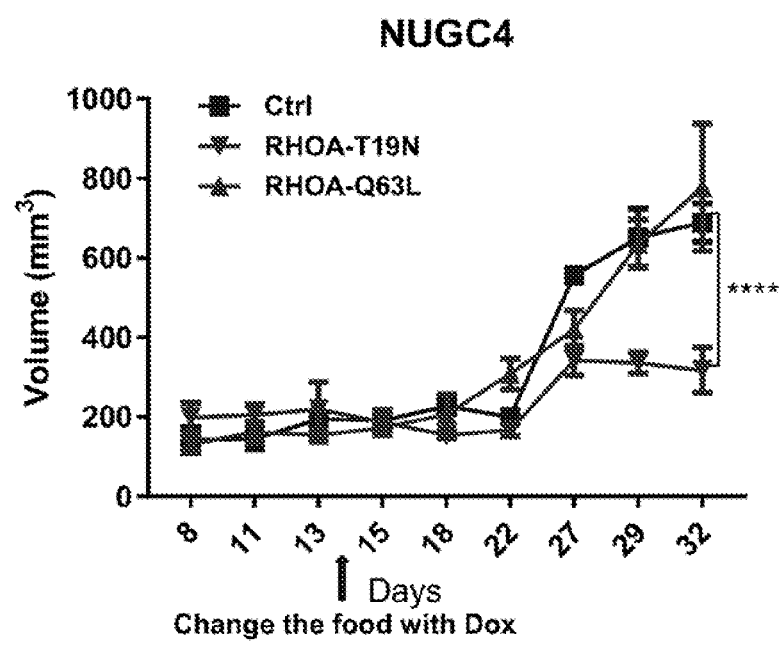
Figure 4:
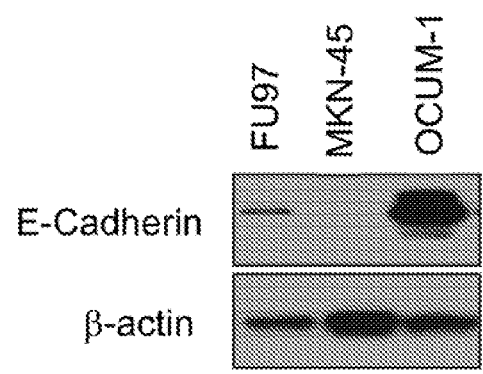
FIG. 4 shows that RHOA-T19N can significantly inhibit MKN45 tumor growth. The diffuse adenocarcinoma MKN45 cells were confirmed for total E-cadherin loss by Western blot analysis. The cells were then stably infected with Dox-inducible *lenti*-RHOA virus using puro selection. Three million MKN45 cells were injected into the flank of nude mice. After 2 weeks, regular food was changed to food with Dox in order to induce mutant RHOA expression. N=3 mice for each group. P<0.0001: Ctrl-VS-T19N.
Figure 4:
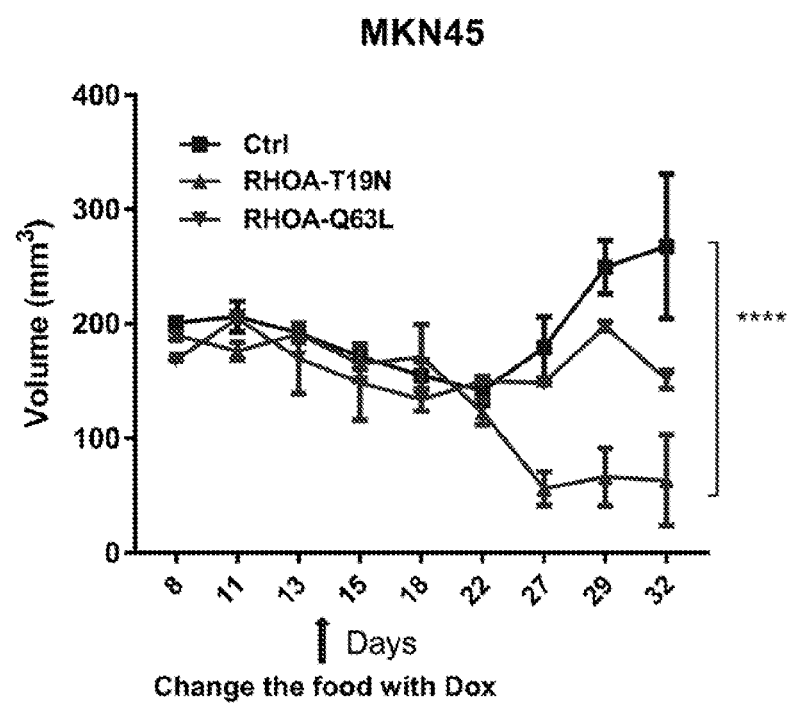

For any figure showing a bar histogram, the bars from left to right for each indication correspond directly and in order to the boxes from top to bottom of the legend, as shown.

DETAILED DESCRIPTION OF THE INVENTION

The present invention is based in part on the discovery that small GTPase RHOA dominant negative forms (e.g., RHOA T19N, RHOA G17E, or RHOA G17V) modulate hyperproliferation of cancer cells having reduced and/or absent CDH1 expression, such as in CDH1-null cancer cells, whereas cancer cells wherein CDH1 expression is intact are spared. For example, the RHOA T19N dominant negative form specifically kills CDH1-null MCF10A cells, but spares CDH1-intact MCF10A cells. Similar results were found using isogenic stomach organoid models. Ectopic expression of RHOA-T19N, for example, specifically kills CDH1-null stomach organoids. In addition, RHOA-T19N can significantly inhibit tumor growth of the E-cadherin loss NUGC4 and MKN45 diffuse gastric cell lines. Accordingly, the present invention relates, in part, to methods and agents for treating cancer with reduced level of CDH1 using dominant negative RHOA.

I. Definitions

The articles "a" and "an" are used herein to refer to one or to more than one (i.e., to at least one) of the grammatical object of the article. By way of example, "an element" means one element or more than one element.

Unless otherwise specified herein, the terms "antibody" and "antibodies" broadly encompass naturally-occurring forms of antibodies (e.g., IgG, IgA, IgM, IgE) and recombinant antibodies such as single-chain antibodies, chimeric and humanized antibodies and multi-specific antibodies, as well as fragments and derivatives of all of the foregoing, which fragments and derivatives have at least an antigenic binding site. Antibody derivatives may comprise a protein or chemical moiety conjugated to an antibody.

The term "antibody" as used herein also includes an "antigen-binding portion" of an antibody (or simply "antibody portion"). The term "antigen-binding portion", as used herein, refers to one or more fragments of an antibody that retain the ability to specifically bind to an antigen. It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent polypeptides (known as single chain Fv (scFv); see e.g., Bird et al. (1988) *Science* 242:423-426; and Huston et al. (1988) *Proc. Natl. Acad. Sci. USA* 85:5879-5883; and Osbourn et al. 1998, Nature Biotechnology 16: 778). Such single chain antibodies are also intended to be encompassed within the term "antigen-binding portion" of an antibody. Any VH and VL sequences of specific scFv can be linked to human immunoglobulin constant region cDNA or genomic sequences, in order to generate expression vectors encoding complete IgG polypeptides or other isotypes. VH and VL can also be used in the generation of Fab, Fv or other fragments of immunoglobulins using either protein chemistry or recombinant DNA technology. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) *Proc. Natl. Acad. Sci. USA* 90:6444-6448; Poljak, R. J., et al. (1994) *Structure* 2:1121-1123).

Still further, an antibody or antigen-binding portion thereof may be part of larger immunoadhesion polypeptides, formed by covalent or noncovalent association of the antibody or antibody portion with one or more other proteins or peptides. Examples of such immunoadhesion polypeptides include use of the streptavidin core region to make a tetrameric scFv polypeptide (Kipriyanov, S. M., et al. (1995) *Human Antibodies and Hybridomas* 6:93-101) and use of a cysteine residue, a marker peptide and a C-terminal polyhistidine tag to make bivalent and biotinylated scFv polypeptides (Kipriyanov, S. M., et al. (1994) *Mol. Immunol.* 31:1047-1058). Antibody portions, such as Fab and F(ab')2 fragments, can be prepared from whole antibodies using conventional techniques, such as papain or pepsin digestion, respectively, of whole antibodies. Moreover, antibodies, antibody portions and immunoadhesion polypeptides can be obtained using standard recombinant DNA techniques, as described herein.

Antibodies may be polyclonal or monoclonal; xenogeneic, allogeneic, or syngeneic; or modified forms thereof (e.g., humanized, chimeric, etc.). Antibodies may also be fully human. The terms "monoclonal antibodies" and "monoclonal antibody composition", as used herein, refer to a population of antibody polypeptides that contain only one species of an antigen binding site capable of immunoreacting with a particular epitope of an antigen, whereas the term "polyclonal antibodies" and "polyclonal antibody composition" refer to a population of antibody polypeptides that contain multiple species of antigen binding sites capable of interacting with a particular antigen. A monoclonal antibody composition typically displays a single binding affinity for a particular antigen with which it immunoreacts.

The term "antisense" nucleic acid polypeptide comprises a nucleotide sequence which is complementary to a "sense" nucleic acid encoding a protein, e.g., complementary to the coding strand of a double-stranded cDNA polypeptide, complementary to an mRNA sequence or complementary to the coding strand of a gene. Accordingly, an antisense nucleic acid polypeptide can hydrogen bond to a sense nucleic acid polypeptide.

The term "body fluid" refers to fluids that are excreted or secreted from the body as well as fluids that are normally not (e.g., amniotic fluid, aqueous humor, bile, blood and blood plasma, cerebrospinal fluid, cerumen and earwax, cowper's fluid or pre-ejaculatory fluid, chyle, chyme, stool, female ejaculate, interstitial fluid, intracellular fluid, lymph, menses, breast milk, mucus, pleural fluid, peritoneal fluid, pus, saliva, sebum, semen, serum, sweat, synovial fluid, tears, urine, vaginal lubrication, vitreous humor, vomit). In a preferred embodiment, body fluids are restricted to blood-related fluids, including whole blood, serum, plasma, and the like.

The terms "cancer" or "tumor" or "hyperproliferative disorder" refer to the presence of cells possessing characteristics typical of cancer-causing cells, such as uncontrolled proliferation, immortality, metastatic potential, rapid growth and proliferation rate, and certain characteristic morphological features. Cancer is generally associated with uncontrolled cell growth, invasion of such cells to adjacent tissues, and the spread of such cells to other organs of the body by vascular and lymphatic menas. Cancer invasion occurs when cancer cells intrude on and cross the normal boundaries of adjacent tissue, which can be measured by assaying cancer cell migration, enzymatic destruction of basement membranes by cancer cells, and the like. In some embodiments, a particular stage of cancer is relevant and such stages can include the time period before and/or after angiogenesis, cellular invasion, and/or metastasis. Cancer cells are often in the form of a solid tumor, but such cells may exist alone within an animal, or may be a non-tumorigenic cancer cell, such as a leukemia cell. Cancers include, but are not limited to, B cell cancer, e.g., multiple myeloma, Waldenström's macroglobulinemia, the heavy chain diseases, such as, for example, alpha chain disease, gamma chain disease, and mu chain disease, benign monoclonal gammopathy, and immunocytic amyloidosis, melanomas, breast cancer, lung cancer, bronchus cancer, colorectal cancer, prostate cancer, pancreatic cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematological tissues, and the like. Other non-limiting examples of types of cancers applicable to the methods encompassed by the present invention include human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, liver cancer, choriocarcinoma, seminoma, embryonal carcinoma, Wilms' tumor, cervical cancer, bone cancer, brain tumor, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease. In some embodiments, the cancer whose phenotype is determined by the method of the present invention is an epithelial cancer such as, but not limited to, bladder cancer, breast cancer, cervical cancer, colon cancer, gynecologic cancers, renal cancer, laryngeal cancer, lung cancer, oral cancer, head and neck cancer, ovarian cancer, pancreatic cancer, prostate cancer, or skin cancer. In other embodiments, the cancer is breast cancer, prostate cancer, lung cancer, or colon cancer. In still other embodiments, the epithelial cancer is non-small-cell lung cancer, nonpapillary renal cell carcinoma, cervical carcinoma, ovarian carcinoma (e.g., serous ovarian carcinoma), or breast carcinoma. The epithelial cancers may be characterized in various other ways including, but not limited to, serous, endometrioid, mucinous, clear cell, brenner, or undifferentiated. In some embodiments, the present invention is used in the treatment, diagnosis, and/or prognosis melanoma and its subtypes.

The term "classifying" includes "to associate" or "to categorize" a sample with a disease state. In certain instances, "classifying" is based on statistical evidence, empirical evidence, or both. In certain embodiments, the methods and systems of classifying use of a so-called training set of samples having known disease states. Once established, the training data set serves as a basis, model, or template against which the features of an unknown sample are compared, in order to classify the unknown disease state of the sample. In certain instances, classifying the sample is akin to diagnosing the disease state of the sample. In certain other instances, classifying the sample is akin to differentiating the disease state of the sample from another disease state.

The term "coding region" refers to regions of a nucleotide sequence comprising codons which are translated into amino acid residues, whereas the term "noncoding region" refers to regions of a nucleotide sequence that are not translated into amino acids (e.g., 5' and 3' untranslated regions).

The term "complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

The term "control" refers to any reference standard suitable to provide a comparison to the expression products in the test sample. In one embodiment, the control comprises obtaining a "control sample" from which expression product levels are detected and compared to the expression product levels from the test sample. Such a control sample may comprise any suitable sample, including but not limited to a sample from a control cancer patient (can be stored sample or previous sample measurement) with a known outcome; normal tissue or cells isolated from a subject, such as a normal patient or the cancer patient, cultured primary cells/tissues isolated from a subject such as a normal subject or the cancer patient, adjacent normal cells/tissues obtained from the same organ or body location of the cancer patient, a tissue or cell sample isolated from a normal subject, or a primary cells/tissues obtained from a depository. In another preferred embodiment, the control may comprise a reference standard expression product level from any suitable source, including but not limited to housekeeping genes, an expression product level range from normal tissue (or other previously analyzed control sample), a previously determined expression product level range within a test sample from a group of patients, or a set of patients with a certain outcome (for example, survival for one, two, three, four years, etc.) or receiving a certain treatment. It will be understood by those of skill in the art that such control samples and reference standard expression product levels can be used in combination as controls in the methods of the present invention. In one embodiment, the control may comprise normal or non-cancerous cell/tissue sample. In another preferred embodiment, the control may comprise an expression level for a set of patients, such as a set of cancer patients, or for a set of cancer patients receiving a certain treatment, or for a set of patients with one outcome versus another outcome. In the former case, the specific expression product level of each patient can be assigned to a percentile level of expression, or expressed as either higher or lower than the mean or average of the reference standard expression level. In another preferred embodiment, the control may comprise normal cells, cells from patients treated with combination chemotherapy and cells from patients having benign cancer. In another embodiment, the control may also comprise a measured value for example, average level of expression of a particular gene in a population compared to the level of expression of a housekeeping gene in the same population. Such a population may comprise normal subjects, cancer patients who have not undergone any treatment (i.e., treatment naive), cancer patients undergoing therapy, or patients having benign cancer. In another preferred embodiment, the control comprises a ratio transformation of expression product levels, including but not limited to determining a ratio of expression product levels of two genes in the test sample and comparing it to any suitable ratio of the same two genes in a reference standard; determining expression product levels of the two or more genes in the test sample and determining a difference in expression product levels in any suitable control; and determining expression product levels of the two or more genes in the test sample, normalizing their expression to expression of housekeeping genes in the test sample, and comparing to any suitable control. In particularly preferred embodiments, the control comprises a control sample which is the same lineage and/or type as the test sample. In another embodiment, the control may comprise expression product levels grouped as percentiles within or based on a set of patient samples, such as all patients with cancer. In one embodiment a control expression product level is established wherein higher or lower levels of expression product relative to, for instance, a particular percentile, are used as the basis for predicting outcome. In another preferred embodiment, a control expression product level is established using expression product levels from cancer control patients with a known outcome, and the expression product levels from the test sample are compared to the control expression product level as the basis for predicting outcome. As demonstrated by the data below, the methods of the present invention are not limited to use of a specific cut-point in comparing the level of expression product in the test sample to the control.

As used herein, the term "costimulate" with reference to activated immune cells includes the ability of a costimulatory molecule to provide a second, non-activating receptor mediated signal (a "costimulatory signal") that induces proliferation or effector function. For example, a costimulatory signal can result in cytokine secretion, e.g., in a T cell that has received a T cell-receptor-mediated signal. Immune cells that have received a cell-receptor mediated signal, e.g., via an activating receptor are referred to herein as "activated immune cells."

The term "diagnosing cancer" includes the use of the methods, systems, and code of the present invention to determine the presence or absence of a cancer or subtype thereof in an individual. The term also includes methods, systems, and code for assessing the level of disease activity in an individual. Diagnosis can be performed directly by the agent providing therapeutic treatment. Alternatively, a person providing therapeutic agent can request the diagnostic assay to be performed. The diagnostician and/or the therapeutic interventionist can interpret the diagnostic assay results to determine a therapeutic strategy. Similarly, such alternative processes can apply to other assays, such as prognostic assays.

A molecule is "fixed" or "affixed" to a substrate if it is covalently or non-covalently associated with the substrate such the substrate can be rinsed with a fluid (e.g., standard saline citrate, pH 7.4) without a substantial fraction of the molecule dissociating from the substrate.

The term "gene expression data" or "gene expression level" as used herein refers to information regarding the relative or absolute level of expression of a gene or set of genes in a cell or group of cells. The level of expression of a gene may be determined based on the level of RNA, such as mRNA, encoded by the gene. Alternatively, the level of expression may be determined based on the level of a polypeptide or fragment thereof encoded by the gene. Gene expression data may be acquired for an individual cell, or for a group of cells such as a tumor or biopsy sample. Gene expression data and gene expression levels can be stored on computer readable media, e.g., the computer readable medium used in conjunction with a microarray or chip reading device. Such gene expression data can be manipulated to generate gene expression signatures.

The term "gene expression signature" or "signature" as used herein refers to a group of coordinately expressed genes. The genes making up this signature may be expressed in a specific cell lineage, stage of differentiation, or during a particular biological response. The genes can reflect biological aspects of the tumors in which they are expressed, such as the cell of origin of the cancer, the nature of the non-malignant cells in the biopsy, and the oncogenic mechanisms responsible for the cancer.

The term "homologous" or "homology" as used herein, refers to nucleotide sequence similarity between two regions of the same nucleic acid strand or between regions of two different nucleic acid strands. When a nucleotide residue position in both regions is occupied by the same nucleotide residue, then the regions are homologous at that position. A first region is homologous to a second region if at least one nucleotide residue position of each region is occupied by the same residue. Homology between two regions is expressed in terms of the proportion of nucleotide residue positions of the two regions that are occupied by the same nucleotide residue. By way of example, a region having the nucleotide sequence 5'-ATTGCC-3' and a region having the nucleotide sequence 5'-TATGGC-3' share 50% homology. Preferably, the first region comprises a first portion and the second region comprises a second portion, whereby, at least about 50%, and preferably at least about 75%, at least about 90%, or at least about 95% of the nucleotide residue positions of each of the portions are occupied by the same nucleotide residue. More preferably, all nucleotide residue positions of each of the portions are occupied by the same nucleotide residue.

The term "host cell" is intended to refer to a cell into which a nucleic acid of the present invention, such as a recombinant expression vector of the present invention, has been introduced. The terms "host cell" and "recombinant host cell" are used interchangeably herein. It should be understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

The term "humanized antibody," as used herein, is intended to include antibodies made by a non-human cell having variable and constant regions which have been altered to more closely resemble antibodies that would be made by a human cell, for example, by altering the non-human antibody amino acid sequence to incorporate amino acids found in human germline immunoglobulin sequences. Humanized antibodies may include amino acid residues not encoded by human germline immunoglobulin sequences (e.g., mutations introduced by random or site-specific mutagenesis in vitro or by somatic mutation in vivo), for example in the CDRs.

The term "humanized antibody", as used herein, also includes antibodies in which CDR sequences derived from the germline of another mammalian species, such as a mouse, have been grafted onto human framework sequences.

As used herein, the term "immune cell" refers to cells that play a role in the immune response. Immune cells are of hematopoietic origin, and include lymphocytes, such as B cells and T cells; natural killer cells; myeloid cells, such as monocytes, macrophages, eosinophils, mast cells, basophils, and granulocytes.

As used herein, the term "immune response" includes T cell mediated and/or B cell mediated immune responses. Exemplary immune responses include T cell responses, e.g., cytokine production and cellular cytotoxicity. In addition, the term immune response includes immune responses that are indirectly effected by T cell activation, e.g., antibody production (humoral responses) and activation of cytokine responsive cells, e.g., macrophages.

The term "immunotherapeutic agent" can include any molecule, peptide, antibody or other agent which can stimulate a host immune system to generate an immune response to a tumor or cancer in the subject. Various immunotherapeutic agents are useful in the compositions and methods described herein. Numerous anti-cancer agents in the immunotherapeutic agent class are well-known in the art and include, without limitation, antibodies that block or inhibit the function of PD-1, PD-L1, PD-L2, CTLA4, and the like. As used herein, the term "inhibit" includes the decrease, limitation, or blockage, of, for example a particular action, function, or interaction. For example, cancer is "inhibited" if at least one symptom of the cancer, such as hyperproliferative growth, is alleviated, terminated, slowed, or prevented. As used herein, cancer is also "inhibited" if recurrence or metastasis the cancer is reduced, slowed, delayed, or prevented.

As used herein, the term "inhibitory signal" refers to a signal transmitted via an inhibitory receptor (e.g., CTLA-4 or PD-1) for a polypeptide on an immune cell. Such a signal antagonizes a signal via an activating receptor (e.g., via a TCR, CD3, BCR, or Fc polypeptide) and can result in, e.g., inhibition of second messenger generation; an inhibition of proliferation; an inhibition of effector function in the immune cell, e.g., reduced phagocytosis, reduced antibody production, reduced cellular cytotoxicity, the failure of the immune cell to produce mediators, (such as cytokines (e.g., IL-2) and/or mediators of allergic responses); or the development of anergy.

As used herein, the term "interaction," when referring to an interaction between two molecules, refers to the physical contact (e.g., binding) of the molecules with one another.

Generally, such an interaction results in an activity (which produces a biological effect) of one or both of said molecules. The activity may be a direct activity of one or both of the molecules. Alternatively, one or both molecules in the interaction may be prevented from binding their ligand, and thus be held inactive with respect to ligand binding activity (e.g., binding its ligand and triggering or inhibiting an immune response). To inhibit such an interaction results in the disruption of the activity of one or more molecules involved in the interaction. To enhance such an interaction is to prolong or increase the likelihood of said physical contact, and prolong or increase the likelihood of said activity.

An "isolated antibody," as used herein, is intended to refer to an antibody that is substantially free of other antibodies having different antigenic specificities. Moreover, an isolated antibody may be substantially free of other cellular material and/or chemicals.

As used herein, an "isolated protein" refers to a protein that is substantially free of other proteins, cellular material, separation medium, and culture medium when isolated from cells or produced by recombinant DNA techniques, or chemical precursors or other chemicals when chemically synthesized. An "isolated" or "purified" protein or biologically active portion thereof is substantially free of cellular material or other contaminating proteins from the cell or tissue source from which the antibody, polypeptide, peptide or fusion protein is derived, or substantially free from chemical precursors or other chemicals when chemically synthesized. The language "substantially free of cellular material" includes preparations, in which compositions of the present invention are separated from cellular components of the cells from which they are isolated or recombinantly produced. In one embodiment, the language "substantially free of cellular material" includes preparations of having less than about 30%, 20%, 10%, or 5% (by dry weight) of cellular material. When an antibody, polypeptide, peptide or fusion protein or fragment thereof, e.g., a biologically active fragment thereof, is recombinantly produced, it is also preferably substantially free of culture medium, i.e., culture medium represents less than about 20%, more preferably less than about 10%, and most preferably less than about 5% of the volume of the protein preparation.

A "kit" is any manufacture (e.g., a package or container) comprising at least one reagent, e.g., a probe, for specifically detecting or modulating the expression of a marker of the present invention. The kit may be promoted, distributed, or sold as a unit for performing the methods of the present invention.

The term "diffuse gastric cancer" refers to a specific type of stomach cancer, sometimes also called "signet ring cell gastric cancer" or "linitis plastic." It tends to affect much of the stomach rather than staying in one area of the stomach. There is no solid tumor. Instead, cancerous (malignant) cells multiply underneath the stomach lining, making the lining thick and rigid. The invasive nature of this type of cancer makes it highly likely that these cancer cells will spread (metastasize) to other tissues, such as the liver or nearby bones. Approximately 20% of all stomach cancers are diffuse gastric cancers, and a small number of these are due to hereditary diffuse gastric cancer (HDGC). HDGC is an inherited, genetic condition. The gene most commonly associated with HDGC is called CDH1. A mutation (alteration) in the CDH1 gene gives a person an increased risk of developing gastric cancer and other cancers associated with HDGC. Other genes including CTNNA/may be associated with HDGC.

Endoscopy and barium X-ray analysescan be used to diagonose stomach cancer. One or more of the tests selected from CT scan, PET scan, endoscopic ultrasound, and laparoscopic staging can be used to determine the stage of a gastric tumor. The diffuse gastric cancer is difficult to diagnose because the cancer is not visible on upper endoscopy. For this reason, most cases of diffuse gastric cancer are diagnosed at late stages (III or IV) and associated with a lower survival rate. Families with multiple cases of diffuse gastric cancer, as well as patients diagnosed with diffuse gastric cancer before age 40, are recommended for testing for CDH1 gene mutations. The current screening recommendations are upper endoscopy with biopsies on an annual basis. Surgery (e.g., partial gastrectomy or total gastrectomy) is the most common treatment approach, especially when the illness is at an early stage. For more advanced stomach cancer, treatments in addition to surgery, such as chemotherapy, radiation therapy, or a combination of these approaches may be used.

The term "lobular breast cancer", also called invasive lobular carcinoma (ILC), refers to cancer that has broken through the wall of the lobule and begun to invade the tissues of the breast. ILC is the second most common type of breast cancer after invasive ductal carcinoma (cancer that begins in the milk-carrying ducts and spreads beyond it). According to the American Cancer Society, more than 180,000 women in the United States find out they have invasive breast cancer each year. About 10% of all invasive breast cancers are invasive lobular carcinomas.

ILC can be more difficult to diagnose than other forms of breast cancer because it spreads in a unique pattern of branching. Diagnosing invasive lobular carcinoma usually involves a combination of procedures, which include physical examination of the breasts, mammography, ultrasound, breast MRI, and biopsy (e.g., fine needle aspiration biopsy, core needle biopsy, incisional biopsy, or excisional biopsy). The tissue samples are sent to a pathologist for examination under a microscope. The pathologist looks for the cell appearance and growth patterns that are typical of invasive lobular carcinoma. The pathologist may also order a special test called an E-cadherin protein study. Testing invasive lobular carcinoma cells for this mutation can help distinguish it from lobular carcinoma in situ, a group of abnormal cells in the lobule that are not cancer. Invasive lobular carcinoma is described on a scale from stage I (the earliest stage) through stage IV (the most advanced stage). Staging has to do with the size of the tumors, lymph node involvement, and whether they have spread to other areas of the body. Higher numbers represent more advanced stages.

The treatments for invasive lobular carcinoma fall into two broad categories: local treatments and systemic treatments. Local treatments such as surgery and radiation therapy are given to treat the invasive lobular carcinoma (ILC) itself and any nearby areas that may be affected by cancer, such as the chest and lymph nodes. Possible surgical procedures include lumpectomy, mastectomy, sentinel lymph node dissection, and axillary lymph node dissection. Possible ways of giving radiation therapy include external beam radiation, internal partial-breast irradiation, and external partial-breast irradiation. Unlike local treatments, which focus on the area (or areas) where the invasive lobular carcinoma (ILC) was found, systemic treatments involve the entire body. Treatments such as chemotherapy, hormonal therapy, and other targeted therapies are used to destroy any cancer cells that may have left the original tumor, as well as to reduce the risk of the invasive lobular carcinoma coming back. Just some examples of the many chemotherapies that may be used to treat invasive lobular carcinoma include Adriamycin, Ellence, Cytoxan, Taxotere, Taxol, Xeloda, Ixempra, methotrexate, and fluorouracil. Hormonal therapy, also called anti-estrogen therapy, works by lowering the amount of estrogen in the body or blocking the estrogen from signaling breast cancer cells to grow. There are two types of hormonal therapy that are most frequently used: Selective estrogen receptor modulators (SERMs) and Aromatase inhibitors. Other types of hormonal therapy include estrogen receptor downregulators (ERDs) and ovarian shutdown or removal. HER2-targeted therapies (e.g., Herceptin or Tykerb) can be used if an invasive lobular carcinoma is HER2-positive. Like hormonal therapy and HER2-targeted therapies, other targeted therapies are designed to interfere with a certain process that enables breast cancer cells to grow and thrive. Just one example is Avastin (chemical name: bevacizumab), a medication that targets a protein called vascular endothelial growth factor (VEGF), which can prevent it from stimulating the formation and growth of new blood vessels.

TABLE 1

Markers of EMT

| Acquired markers | | Attenuated markers | |
|---|---|---|---|
| Name | EMT type | Name | EMT type |
| Cell-surface proteins | | | |
| N-cadherin | 1, 2 | E-cadherin | 1, 2, 3 |
| OB-cadherin | 3 | ZO-1 | 1, 2, 3 |
| α5β1 integrin | 1, 3 | | |
| αVβ6 integrin | 1, 3 | | |
| Syndecan-1 | 1, 3 | | |
| Cytoskeletal markers | | | |
| FSP1 | 1, 2, 3 | Cytokeratin | 1, 2, 3 |
| α-SMA | 2, 3 | | |
| Vimentin | 1, 2 | | |
| β-Catenin | 1, 2, 3 | | |
| ECM proteins | | | |
| α1(I) collagen | 1, 3 | α1(IV) collagen | 1, 2, 3 |
| α1(III) collagen | 1, 3 | Laminin 1 | 1, 2, 3 |
| Fibronectin | 1, 2 | | |
| Laminin 5 | 1, 2 | | |
| Transcription factors | | | |
| Snail1 (Snail) | 1, 2, 3 | | |
| Snail2 (Slug) | 1, 2, 3 | | |
| ZEB1 | 1, 2, 3 | | |
| CBF-A/KAP-1 complex | 2, 3 | | |
| Twist | 1, 2, 3 | | |
| LEF-1 | 1, 2, 3 | | |
| Ets-1 | 1, 2, 3 | | |
| FOXC2 | 1, 2 | | |
| Goosecoid | 1, 2 | | |
| MicroRNAs | | | |
| miR10b | 2 | Mir-200 family | 2 |
| miR-21 | 2, 3 | | |

ZEB1, zinc finger E-box binding homeobox 1.

The term "epithelial—mesenchymal transition (EMT)," refers to a biologic process that allows a polarized epithelial cell, which normally interacts with basement membrane via its basal surface, to undergo multiple biochemical changes that enable it to assume a mesenchymal cell phenotype, which includes enhanced migratory capacity, invasiveness, elevated resistance to apoptosis, and greatly increased production of ECM components. The completion of an EMT is signaled by the degradation of underlying basement membrane and the formation of a mesenchymal cell that can migrate away from the epithelial layer in which it originated. A number of distinct molecular processes are engaged in order to initiate an EMT and enable it to reach completion. These include activation of transcription factors, expression of specific cell-surface proteins, reorganization and expression of cytoskeletal proteins, production of ECM-degrading enzymes, and changes in the expression of specific microRNAs. In many cases, the involved factors are also used as biomarkers to demonstrate the passage of a cell through an EMT. Loss of E-cadherin is considered to be a fundamental event in EMT. EMT is essential for numerous developmental processes including mesoderm formation and neural tube formation. EMT has also been shown to occur in wound healing, in organ fibrosis and in the initiation of metastasis for cancer progression. Initiation of metastasis requires invasion, which is enabled by EMT. Carcinoma cells in primary tumor lose cell-cell adhesion mediated by E-cadherin repression and break through the basement membrane with increased invasive properties, and enter the bloodstream through intravasation. The term "EMT cancer" refers to any cancer type that is undergoing or has undergone the EMT process. EMT cancers include but are not limited to diffuse gastric cancer, lobular breast cancer, metastatic breast cancer, metastatic lung cancer, metastatic non small-cell lung cancer, colon cancer, pancreatic cancer, prostate cancer, brain cancer and melanoma.

With EMT, epithelial cells transitioning towards a more mesenchymal state lose polarity; increase their nuclear expression of several transcription factors (see Table 1); lose the expression of E-cadherin, syndecan-1, and zona occludens 1 (ZO-1); increase their synthesis of cytoskeletal proteins (see below); rearrange actin stress fibers; become spindle-shaped; and become more migratory. These EMT-like cells can also be resistant to apoptosis and cancer chemotherapy.

A variety of biomarkers have been used to demonstrate EMT, some of which are acquired and some of which are attenuated during transition (see Table 1). A change in expression of E-cadherin is the prototypical epithelial cell marker of EMT and loss of E-cadherin function promotes EMT. The cadherin switch from E-cadherin to N-cadherin, which is expressed in mesenchymal cells, fibroblasts, cancer cells, and neural tissue, has often been used to monitor the progress of EMT. FSP1 is a member of the family of $Ca^{2+}$-binding S100 proteins. It is a prototypical fibroblast marker for detecting EMT in cancer and fibrogenesis. Snail transcription factors are one prominent example of a common downstream target of various signaling pathways that regulates EMT.

The term "modulate" includes up-regulation and down-regulation, e.g., enhancing or inhibiting a response.

The "normal" or "control" level of expression of a biomarker, such as CDH1, RHOA, and the like, is the level of expression of the biomarker in cells of a subject, e.g., a human patient, not afflicted with disease of interest, such as cancer. An "over-expression" or "significantly higher level of expression" of a biomarker refers to an expression level in a test sample that is greater than the standard error of the assay employed to assess expression, and is preferably at least 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more higher than the expression activity or level of the biomarker in a control sample (e.g., sample from a healthy subject not having the disease of interest) and preferably, the average expression level of the biomarker in several control samples. A "significantly lower level of expression" of a biomarker refers to an expression level in a test sample that is at least 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more lower than the expression level of the biomarker in a control sample (e.g., sample from a healthy subject not having the the disease of interest) and preferably, the average expression level of the biomarker in several control samples.

The term "pre-malignant lesions" as described herein refers to a lesion that, while not cancerous, has potential for becoming cancerous. It also includes the term "pre-malignant disorders" or "potentially malignant disorders." In particular this refers to a benign, morphologically and/or histologically altered tissue that has a greater than normal risk of malignant transformation, and a disease or a patient's habit that does not necessarily alter the clinical appearance of local tissue but is associated with a greater than normal risk of precancerous lesion or cancer development in that tissue (leukoplakia, erythroplakia, erytroleukoplakia lichen planus (lichenoid reaction) and any lesion or an area which histological examination showed atypia of cells or dysplasia.

The term "probe" refers to any molecule which is capable of selectively binding to a specifically intended target molecule, for example, a nucleotide transcript or protein encoded by or corresponding to a marker. Probes can be either synthesized by one skilled in the art, or derived from appropriate biological preparations. For purposes of detection of the target molecule, probes may be specifically designed to be labeled, as described herein. Examples of molecules that can be utilized as probes include, but are not limited to, RNA, DNA, proteins, antibodies, and organic molecules.

The term "prognosis" includes a prediction of the probable course and outcome of cancer or the likelihood of recovery from the disease. In some embodiments, the use of statistical algorithms provides a prognosis cancer in an individual. For example, the prognosis can be surgery, development of a clinical subtype of melanoma, development of one or more clinical factors, development of intestinal cancer, or recovery from the disease. In some embodiments, the term "good prognosis" indicates that the expected or likely outcome after treatment of melanoma is good. The term "poor prognosis" indicates that the expected or likely outcome after treatment of melanoma is not good.

The term "resistance" refers to an acquired or natural resistance of a cancer sample or a mammal to a cancer therapy (i.e., being nonresponsive to or having reduced or limited response to the therapeutic treatment), such as having a reduced response to a therapeutic treatment by 25% or more, for example, 30%, 40%, 50%, 60%, 70%, 80%, or more, to 2-fold, 3-fold, 4-fold, 5-fold, 10-fold, 15-fold, 20-fold or more. The reduction in response can be measured by comparing with the same cancer sample or mammal before the resistance is acquired, or by comparing with a different cancer sample or a mammal who is known to have no resistance to the therapeutic treatment. A typical acquired resistance to chemotherapy is called "multidrug resistance." The multidrug resistance can be mediated by P-glycoprotein or can be mediated by other mechanisms, or it can occur when a mammal is infected with a multi-drug-resistant microorganism or a combination of microorganisms. The determination of resistance to a therapeutic treatment is routine in the art and within the skill of an ordinarily skilled clinician, for example, can be measured by cell proliferative assays and cell death assays as described herein as "sensitizing." In some embodiments, the term "reverses resistance" means that the use of a second agent in combination with a primary cancer therapy (e.g., chemotherapeutic or radiation therapy) is able to produce a significant decrease in tumor volume at a level of statistical significance (e.g., p<0.05) when compared to tumor volume of untreated tumor in the circumstance where the primary cancer therapy (e.g., chemotherapeutic or radiation therapy) alone is unable to produce a statistically significant decrease in tumor volume compared to tumor volume of untreated tumor. This generally applies to tumor volume measurements made at a time when the untreated tumor is growing log rhythmically.

The term "sensitize" means to alter cancer cells or tumor cells in a way that allows for more effective treatment of the associated cancer with a cancer therapy (e.g., chemotherapeutic or radiation therapy. In some embodiments, normal cells are not affected to an extent that causes the normal cells to be unduly injured by the cancer therapy (e.g., chemotherapy or radiation therapy). An increased sensitivity or a reduced sensitivity to a therapeutic treatment is measured according to a known method in the art for the particular treatment and methods described herein below, including, but not limited to, cell proliferative assays (Tanigawa N, Kern D H, Kikasa Y, Morton D L, Cancer Res 1982; 42: 2159-2164), cell death assays (Weisenthal L M, Shoemaker R H, Marsden J A, Dill P L, Baker J A, Moran E M, Cancer Res 1984; 94: 161-173; Weisenthal L M, Lippman M E, Cancer Treat Rep 1985; 69: 615-632; Weisenthal L M, In: Kaspers G J L, Pieters R, Twentyman P R, Weisenthal L M, Veerman A J P, eds. Drug Resistance in Leukemia and Lymphoma. Langhorne, P A: Harwood Academic Publishers, 1993: 415-432; Weisenthal L M, Contrib Gynecol Obstet 1994; 19: 82-90). The sensitivity or resistance may also be measured in animal by measuring the tumor size reduction over a period of time, for example, 6 month for human and 4-6 weeks for mouse. A composition or a method sensitizes response to a therapeutic treatment if the increase in treatment sensitivity or the reduction in resistance is 25% or more, for example, 30%, 40%, 50%, 60%, 70%, 80%, or more, to 2-fold, 3-fold, 4-fold, 5-fold, 10-fold, 15-fold, 20-fold or more, compared to treatment sensitivity or resistance in the absence of such composition or method. The determination of sensitivity or resistance to a therapeutic treatment is routine in the art and within the skill of an ordinarily skilled clinician. It is to be understood that any method described herein for enhancing the efficacy of a cancer therapy can be equally applied to methods for sensitizing hyperproliferative or otherwise cancerous cells (e.g., resistant cells) to the cancer therapy.

The term "RHOA" refers to Ras Homolog Family Member A, a member of the Rho family of small GTPases, which cycle between inactive GDP-bound and active GTP-bound states and function as molecular switches in signal transduction cascades. Rho proteins promote reorganization of the actin cytoskeleton and regulate cell shape, attachment, and motility. Overexpression of this gene is associated with tumor cell proliferation and metastasis. Multiple alternatively spliced variants have been identified. The term "RHOA" is intended to include fragments, variants (e.g., allelic variants), and derivatives thereof. Representative human RHOA cDNA and human RHOA protein sequences are well-known in the art and are publicly available from the National Center for Biotechnology Information (NCBI). Human RHOA isoforms include the longest isoform 1 (NM_001664.3 and NP_001655.1), the shorter isoforms 2

(NM_001313941.1 and NP_001300870.1; which differs in the 5' UTR compared to variant 1 but encodes the same protein), 3 (NM_001313943.1 and NP_001300872.1; which contains an alternate 3' coding exon, resulting in a shorter and distinct C-terminus compared to isoform 1), 4 (NM_001313944.1 and NP_001300873.1; which uses two alternate in-frame splice sites in the 3' coding region, resulting in a shorter isoform compared to isoform 1), 5 (NM_001313945.1 and NP_001300874.1; which uses an alternate splice site in the 5' region and uses a downstream start codon, resulting in a shorter N-terminus compared to isoform 1), 6 (NM_001313946.1 and NP_001300875.1; which lacks lacks two alternate in-frame exons in the 3' coding region, resulting in a shorter isoform compared to isoform 1), and 7 (NM_001313947.1 and NP_001300876.1; which lacks an alternate exon in the 5' coding region which results in a frameshift, resulting in a shorter isoform with distinct C-terminus compared to isoform 1). Nucleic acid and polypeptide sequences of RHOA orthologs in organisms other than humans are well-known and include, for example, chimpanzee RHOA (XM_001163851.5 and XP_001163851.3), dog RHOA (NM_001003273.3 and NP_001003273.2), cattle RHOA (NM_176645.3 and NP_788818.1), mouse RHOA (NM_001313961.1 and NP_001300890.1; NM_001313962.1 and NP_001300891.1; and NM_016802.5 and NP_058082.2), and rat RHOA (XM_006243699.1 and XP_006243761.1; XM_006243700.1 and XP_006243762.1; and XM_006243701.1 and XP_006243763.1).

The term "dominant negative RHOA" refers to a RHOA gene or protein which harbors one or more mutations and therefore fails to bind GTP, acts in a dominat-negative fashion to inhibit RhoA GTP loading leading to attenuation of endogenous RHOA and other GTPases. In some embodiments, they can sequester other GTPase activating proteins and guanine exchange factors. These mutations include, but are not limited to, T19N, G17V, and G17E. Exemplary "dominant negative RhoA" are shown by the sequences presented in Table 2 and Table 3.

The term "CDH1" refers to cadherin 1, a classical cadherin of the cadherin superfamily. This gene is present in a gene cluster with other members of the cadherin family on chromosome 16. Alternative splicing results in multiple transcript variants, at least one of which encodes a preproprotein that is proteolytically processed to generate the mature glycoprotein. This calcium-dependent cell-cell adhesion protein is comprised of five extracellular cadherin repeats, a transmembrane region and a highly conserved cytoplasmic tail. The structure-function relationship of the protein is well known. For example, the intracellular domain contains a highly-phosphorylated region vital to catenin molecules (e.g., beta-catenin) binding and, therefore, to E-cadherin function. Mutations in this gene are correlated with gastric, breast, colorectal, thyroid and ovarian cancer. In-frame skipping of exons 8 or 9 and deletion of exon 10 have been demonstrated with diffuse-type gastric cancer. Point mutations in exons 7 (invasive breast carcinoma), 12 and 13 (endometrial carcinoma) and 16 (ovarian carcinoma) have also been demonstrated that mostly affects the extracellular domain of E-cadherin. Probably the best known tumours exhibiting mutations of CDH1 are invasive lobular carcinoma of the breast and diffuse gastric cancer, with approximately 50% of these tumours being affected. A germ line mutation of CDH1 has been detected in various families, that results in the development of poorly differentiated diffuse-type adenocarcinomas with signet-ring cells. The term "hereditary diffuse gastric cancer (HDGC) syndrome" has been coined to describe affected patients. Loss of function of CDH1 gene contributes to cancer progression by increasing proliferation, invasion, and/or metastasis. The ectodomain of this protein could also mediate bacterial adhesion to mammalian cells and the cytoplasmic domain is required for internalization.

Multiple alternatively spliced variants have been identified. The term "CDH1" is intended to include fragments, variants (e.g., allelic variants), and derivatives thereof. Representative human CDH1 cDNA and human CDH1 protein sequences are well-known in the art and are publicly available from the National Center for Biotechnology Information (NCBI). Human CDH1 isoforms include the longest isoform 1 (NM_004360.4 and NP_004351.1), the shorter isoforms 2 (NM_001317184.1 and NP_001304113.1; which lacks an alternate exon in the central coding region compared to variant 1), 3 (NM_001317185.1 and NP_001304114.1; which uses an alternate splice site in an exon in its 5' UTR, resulting in a different 5' UTR and the use of a downstream start site compared to variant 1), and 4 (NM_001317186.1 and NP_001304115.1; which lacks an exon in its 5' UTR, resulting in a different 5' UTR and the use of a downstream start site compared to variant 1). Nucleic acid and polypeptide sequences of CDH1 orthologs in organisms other than humans are well-known and include, for example, chimpanzee CDH1 (XM_001168150.4 and XP_001168150.1; XM_016930064.1 and XP_016785553.1; XM_016930063.1 and XP_016785552.1), monkey CDH1 (XM_015126485.1 and XP_014981971.1; 2.XM_015126486.1 and XP_014981972.1), dog CDH1 (NM_001287125.1 and NP_001274054.1), cattle CDH1 (NM_001002763.1 and NP_001002763.1), mouse CDH1 (NM_009864.3 and NP_033994.1), and rat CDH1 (NM_031334.1 and NP_112624.1).

The term "synergistic effect" refers to the combined effect of two or more anticancer agents or chemotherapy drugs can be greater than the sum of the separate effects of the anticancer agents or chemotherapy drugs alone.

The term "subject" refers to any healthy animal, mammal or human, or any animal, mammal or human afflicted with a condition of interest (e.g., cancer). The term "subject" is interchangeable with "patient." In some embodiments, a subject does not have any cancer other than melanoma. In other embodiments, the subject has melanoma but does not have one or more other cancers of interest. For example, in some embodiments, a subject does not have renal cell carcinoma, head or neck cancer, and/or lung cancer.

The language "substantially free of chemical precursors or other chemicals" includes preparations of antibody, polypeptide, peptide or fusion protein in which the protein is separated from chemical precursors or other chemicals which are involved in the synthesis the protein. In one embodiment, the language "substantially free of chemical precursors or other chemicals" includes preparations of antibody, polypeptide, peptide or fusion protein having less than about 30% (by dry weight) of chemical precursors or non-antibody, polypeptide, peptide or fusion protein chemicals, more preferably less than about 20% chemical precursors or non-antibody, polypeptide, peptide or fusion protein chemicals, still more preferably less than about 10% chemical precursors or non-antibody, polypeptide, peptide or fusion protein chemicals, and most preferably less than about 5% chemical precursors or non-antibody, polypeptide, peptide or fusion protein chemicals.

The term "substantially pure cell population" refers to a population of cells having a specified cell marker characteristic and differentiation potential that is at least about 50%, preferably at least about 75-80%, more preferably at least about 85-90%, and most preferably at least about 95% of the cells making up the total cell population. Thus, a "substantially pure cell population" refers to a population of cells that contain fewer than about 50%, preferably fewer than about 20-25%, more preferably fewer than about 10-15%, and most preferably fewer than about 5% of cells that do not display a specified marker characteristic and differentiation potential under designated assay conditions.

As used herein, the term "survival" includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g., time of diagnosis or start of treatment) and end point (e.g., death, recurrence or metastasis). In addition, criteria for efficacy of treatment can be expanded to include response to chemotherapy, probability of survival, probability of metastasis within a given time period, and probability of tumor recurrence.

A "transcribed polynucleotide" or "nucleotide transcript" is a polynucleotide (e.g., an mRNA, hnRNA, cDNA, mature miRNA, pre-miRNA, pri-miRNA, miRNA*, piwiRNA, anti-miRNA, or a miRNA binding site, or a variant thereof or an analog of such RNA or cDNA) which is complementary to or homologous with all or a portion of a mature mRNA made by transcription of a marker of the present invention and normal post-transcriptional processing (e.g., splicing), if any, of the RNA transcript, and reverse transcription of the RNA transcript. In some embodiments, transcribed polynucleotides are "long non-coding RNAs" or "lcRNAs" that are defined as transcribed polynucleotides that do not naturally encode a translated protein. lcRNAs are generally sequences longer than about 100 nucleotides and can be as long as up to tens of kilobases, although the length definition is a matter of convenience for distinguishing traditionally small nucleic acids like microRNAs, siRNAs, and piwi-associated RNAs. lcRNAs may be located separate from protein coding genes (long intergenic ncRNAs or lincRNAs), or reside near or within protein coding genes (Guttman et al. (2009) Nature 458:223-227; Katayama et al. (2005) Science 309:1564-1566; Kim et al. (2010) Nature 465:182-187; De Santa et al. (2010) PLoS Biol. 8:e1000384).

As used herein, the term "vector" refers to a nucleic acid capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" or simply "expression vectors." In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

As used herein, the term "unresponsiveness" includes refractivity of immune cells to stimulation, e.g., stimulation via an activating receptor or a cytokine. Unresponsiveness can occur, e.g., because of exposure to immunosuppressants or exposure to high doses of antigen. As used herein, the term "anergy" or "tolerance" includes refractivity to activating receptor-mediated stimulation. Such refractivity is generally antigen-specific and persists after exposure to the tolerizing antigen has ceased. For example, anergy in T cells (as opposed to unresponsiveness) is characterized by lack of cytokine production, e.g., IL-2. T cell anergy occurs when T cells are exposed to antigen and receive a first signal (a T cell receptor or CD-3 mediated signal) in the absence of a second signal (a costimulatory signal). Under these conditions, reexposure of the cells to the same antigen (even if reexposure occurs in the presence of a costimulatory polypeptide) results in failure to produce cytokines and, thus, failure to proliferate. Anergic T cells can, however, proliferate if cultured with cytokines (e.g., IL-2). For example, T cell anergy can also be observed by the lack of IL-2 production by T lymphocytes as measured by ELISA or by a proliferation assay using an indicator cell line. Alternatively, a reporter gene construct can be used. For example, anergic T cells fail to initiate IL-2 gene transcription induced by a heterologous promoter under the control of the 5' IL-2 gene enhancer or by a multimer of the AP1 sequence that can be found within the enhancer (Kang et al. (1992) Science 257:1134).

The term "isolated polypeptide" refers to a polypeptide, in certain embodiments prepared from recombinant DNA or RNA, or of synthetic origin, or some combination thereof, which (1) is not associated with proteins that it is normally found within nature, (2) is isolated from the cell in which it normally occurs, (3) is isolated free of other proteins from the same cellular source, (4) is expressed by a cell from a different species, or (5) does not occur in nature.

The terms "label" or "labeled" refer to incorporation or attachment, optionally covalently or non-covalently, of a detectable marker into a molecule, such as a polypeptide. Various methods of labeling polypeptides are known in the art and may be used. Examples of labels for polypeptides include, but are not limited to, the following: radioisotopes, fluorescent labels, heavy atoms, enzymatic labels or reporter genes, chemiluminescent groups, biotinyl groups, predetermined polypeptide epitopes recognized by a secondary reporter (e.g., leucine zipper pair sequences, binding sites for secondary antibodies, metal binding domains, epitope tags). Examples and use of such labels are described in more detail below. In some embodiments, labels are attached by spacer arms of various lengths to reduce potential steric hindrance.

The term "treating" a condition means taking steps to obtain beneficial or desired results, including clinical results, such as mitigating, alleviating or ameliorating one or more symptoms of a disease; diminishing the extent of disease; delaying or slowing disease progression; ameliorating and palliating or stabilizing a metric (statistic) of disease; causing the subject to experience a reduction, delayed progression, regression or remission of the disorder and/or its symptoms. In one embodiment, recurrence of the disorder and/or its symptoms is prevented. In the preferred embodiment, the subject is cured of the disorder and/or its symptoms. In some embodiments, "treatment" or "treating" can also refer to therapy, prevention and prophylaxis and particularly refers to the administration of medicine or the performance of medical procedures with respect to a patient, for either prophylaxis (prevention) or to cure (if possible) or reduce the extent of or likelihood of occurrence of the infirmity or malady or condition or event in the instance where the patient is afflicted. More particularly, as related to the present invention, "treatment" or "treating" is defined as the application or administration of a therapeutic agent to a patient, or application or administration of a therapeutic agent to an isolated tissue or cell line from a patient, who has a disease, a symptom of disease or a predisposition toward development of a disease. Treatment can slow, cure, heal, alleviate, relieve, alter, mitigate, remedy, ameliorate, improve or affect the disease, a symptom of the disease or the predisposition toward disease.

There is a known and definite correspondence between the amino acid sequence of a particular protein and the nucleotide sequences that can code for the protein, as defined by the genetic code (shown below). Likewise, there is a known and definite correspondence between the nucleotide sequence of a particular nucleic acid and the amino acid sequence encoded by that nucleic acid, as defined by the genetic code.

| GENETIC CODE | |
|---|---|
| Alanine (Ala, A) | GCA, GCC, GCG, GCT |
| Arginine (Arg, R) | AGA, ACG, CGA, CGC, CGG, CGT |
| Asparagine (Asn, N) | AAC, AAT |
| Aspartic acid (Asp, D) | GAC, GAT |
| Cysteine (Cys, C) | TGC, TGT |
| Glutamic acid (Glu, E) | GAA, GAG |
| Glutamine (Gln, Q) | CAA, CAG |
| Glycine (Gly, G) | GGA, GGC, GGG, GGT |
| Histidine (His, H) | CAC, CAT |
| Isoleucine (Ile, I) | ATA, ATC, ATT |
| Leucine (Leu, L) | CTA, CTC, CTG, CTT, TTA, TTG |
| Lysine (Lys, K) | AAA, AAG |
| Methionine (Met, M) | ATG |
| Phenylalanine (Phe, F) | TTC, TTT |
| Proline (Pro, P) | CCA, CCC, CCG, CCT |
| Serine (Ser, S) | AGC, AGT, TCA, TCC, TCG, TCT |
| Threonine (Thr, T) | ACA, ACC, ACG, ACT |
| Tryptophan (Trp, W) | TGG |
| Tyrosine (Tyr, Y) | TAC, TAT |
| Valine (Val, V) | GTA, GTC, GTG, GTT |
| Termination signal (end) | TAA, TAG, TGA |

An important and well-known feature of the genetic code is its redundancy, whereby, for most of the amino acids used to make proteins, more than one coding nucleotide triplet may be employed (illustrated above). Therefore, a number of different nucleotide sequences may code for a given amino acid sequence. Such nucleotide sequences are considered functionally equivalent since they result in the production of the same amino acid sequence in all organisms (although certain organisms may translate some sequences more efficiently than they do others). Moreover, occasionally, a methylated variant of a purine or pyrimidine may be found in a given nucleotide sequence. Such methylations do not affect the coding relationship between the trinucleotide codon and the corresponding amino acid.

In view of the foregoing, the nucleotide sequence of a DNA or RNA coding for a fusion protein or polypeptide of the present invention (or any portion thereof) can be used to derive the fusion protein or polypeptide amino acid sequence, using the genetic code to translate the DNA or RNA into an amino acid sequence. Likewise, for a fusion protein or polypeptide amino acid sequence, corresponding nucleotide sequences that can encode the fusion protein or polypeptide can be deduced from the genetic code (which, because of its redundancy, will produce multiple nucleic acid sequences for any given amino acid sequence). Thus, description and/or disclosure herein of a nucleotide sequence which encodes a fusion protein or polypeptide should be considered to also include description and/or disclosure of the amino acid sequence encoded by the nucleotide sequence. Similarly, description and/or disclosure of a fusion protein or polypeptide amino acid sequence herein should be considered to also include description and/or disclosure of all possible nucleotide sequences that can encode the amino acid sequence.

Finally, exemplary nucleic acid and protein sequences of dominant negative RHOA encompassed within the scope of compositions-of-matter and methods of the present invention are shown below.

TABLE 2 amino acid sequences of RHOA dominant negative forms

SEQ ID NO: 1 Human RHOA T19N amino acid seqeunce
MAAIRKKLVIVGDGACGKNCLLIVFSKDQFPEVYVPTVFENYVADIEVDG
KQVELALWDTAGQEDYDRLRPLSYPDTDVILMCFSIDSPDSLENIPEKWT
PEVKHFCPNVPIILVGNKKDLRNDEHTRRELAKMKQEPVKPEEGRDMANR
IGAFGYMECSAKTKDGVREVFEMATRAALQARRGKKKSGCLVL SEQ ID NO: 2 Human RHOA G17V amino acid seqeunce
MAAIRKKLVIVGDGACVKTCLLIVFSKDQFPEVYVPTVFENYVADIEVDG
KQVELALWDTAGQEDYDRLRPLSYPDTDVILMCFSIDSPDSLENIPEKWT
PEVKHFCPNVPIILVGNKKDLRNDEHTRRELAKMKQEPVKPEEGRDMANR
IGAFGYMECSAKTKDGVREVFEMATRAALQARRGKKKSGCLVL SEQ ID NO: 3 Human RHOA G17E amino acid seqeunce
MAAIRKKLVIVGDGACEKTCLLIVESKDQFPEVYVPTVFENYVADIEVDG
KQVELALWDTAGQEDYDRLRPLSYPDTDVILMCFSIDSPDSLENIPEKWT
PEVKHFCPNVPIILVGNKKDLRNDEHTRRELAKMKQEPVKPEEGRDMANR
IGAFGYMECSAKTKDGVREVFEMATRAALQARRGKKKSGCLVL

TABLE 3 cDNA sequences of RHOA dominant negative forms

SEQ ID NO: 4 Human RHOA T19N cDNA sequence,
variant 1
atggctgccatccggaagaaactggtgattgttggtgatggagcctgtgg
aaagAATtgcttgctcatagtcttcagcaaggaccagttcccagaggtgt
atgtgcccacagtgtttgagaactatgtggcagatatcgaggtggatgga
aagcaggtagagttggctttgtgggacacagctgggcaggaagattatga
tcgcctgaggcccctctcctacccagataccgatgttatactgatgtgtt
tttccatcgacagccctgatagtttagaaaacatcccagaaaagtggacc
ccagaagtcaagcatttctgtcccaacgtgcccatcatcctggttgggaa
taagaaggatcttcggaatgatgagcacacaaggcgggagctagccaaga
tgaagcaggagccggtgaaacctgaagaaggcagagatatggcaaacagg
attggcgcttttgggtacatggagtgttcagcaaagaccaaagatggagt
gagagaggttttttgaaatggctacgagagctgctctgcaagctagacgtg
ggaagaaaaaatctgggtgccttgtcttgtga SEQ ID NO: 5 Human RHOA T19N cDNA sequence,
variant 2
atggctgccatccggaagaaactggtgattgttggtgatggagcctgtgg
aaagAACtgcttgctcatagtcttcagcaaggaccagttcccagaggtgt
atgtgcccacagtgtttgagaactatgtggcagatatcgaggtggatgga
aagcaggtagagttggctttgtgggacacagctgggcaggaagattatga
tcgcctgaggcccctctcctacccagataccgatgttatactgatgtgtt
tttccatcgacagccctgatagtttagaaaacatcccagaaaagtggacc
ccagaagtcaagcatttctgtcccaacgtgcccatcatcctggttgggaa
taagaaggatcttcggaatgatgagcacacaaggcgggagctagccaaga
tgaagcaggagccggtgaaacctgaagaaggcagagatatggcaaacagg
attggcgcttttgggtacatggagtgttcagcaaagaccaaagatggagt
gagagaggttttttgaaatggctacgagagctgctctgcaagctagacgtg
ggaagaaaaaatctgggtgccttgtcttgtga TABLE 3-continued cDNA sequences of RHOA dominant negative forms SEQ ID NO: 6 Human RHOA G17V cDNA sequence,
variant 1
atggctgccatccggaagaaactggtgattgttggtgatggagcctgtGT
Taagacatgcttgctcatagtcttcagcaaggaccagttcccagaggtgt
atgtgcccacagtgtttgagaactatgtggcagatatcgaggtggatgga
aagcaggtagagttggctttgtgggacacagctgggcaggaagattatga
tcgcctgaggccctctcctacccagataccgatgttatactgatgtgtt
tttccatcgacagccctgatagtttagaaaacatcccagaaaagtggacc
ccagaagtcaagcatttctgtcccaacgtgcccatcatcctggttgggaa
taagaaggatcttcggaatgatgagcacacaaggcgggagctagccaaga
tgaagcaggagccggtgaaacctgaagaaggcagagatatggcaaacagg
attggcgcttttgggtacatggagtgttcagcaaagaccaaagatggagt
gagagaggttttttgaaatggctacgagagctgctctgcaagctagacgtg
ggaagaaaaaatctgggtgccttgtcttgtga SEQ ID NO: 8 Human RHOA G17V cDNA sequence,
variant 2
atggctgccatccggaagaaactggtgattgttggtgatggagcctgtGT
Caagacatgcttgctcatagtcttcagcaaggaccagttcccagaggtgt
atgtgcccacagtgtttgagaactatgtggcagatatcgaggtggatgga
aagcaggtagagttggctttgtgggacacagctgggcaggaagattatga
tcgcctgaggccctctcctacccagataccgatgttatactgatgtgtt
tttccatcgacagccctgatagtttagaaaacatcccagaaaagtggacc
ccagaagtcaagcatttctgtcccaacgtgcccatcatcctggttgggaa
taagaaggatcttcggaatgatgagcacacaaggcgggagctagccaaga
tgaagcaggagccggtgaaacctgaagaaggcagagatatggcaaacagg
attggcgcttttgggtacatggagtgttcagcaaagaccaaagatggagt
gagagaggttttttgaaatggctacgagagctgctctgcaagctagacgtg
ggaagaaaaaatctgggtgccttgtcttgtga SEQ ID NO: 8 Human RHOA G17V cDNA sequence,
variant 3
atggctgccatccggaagaaactggtgattgttggtgatggagcctgtGT
Gaagacatgcttgctcatagtcttcagcaaggaccagttcccagaggtgt
atgtgcccacagtgtttgagaactatgtggcagatatcgaggtggatgga
aagcaggtagagttggctttgtgggacacagctgggcaggaagattatga
tcgcctgaggccctctcctacccagataccgatgttatactgatgtgtt
tttccatcgacagccctgatagtttagaaaacatcccagaaaagtggacc
ccagaagtcaagcatttctgtcccaacgtgcccatcatcctggttgggaa
taagaaggatcttcggaatgatgagcacacaaggcgggagctagccaaga
tgaagcaggagccggtgaaacctgaagaaggcagagatatggcaaacagg
attggcgcttttgggtacatggagtgttcagcaaagaccaaagatggagt
gagagaggttttttgaaatggctacgagagctgctctgcaagctagacgtg
ggaagaaaaaatctgggtgccttgtcttgtga SEQ ID NO: 9 Human RHOA G17V cDNA sequence,
variant 4
atggctgccatccggaagaaactggtgattgttggtgatggagcctgtGT
Aaagacatgcttgctcatagtcttcagcaaggaccagttcccagaggtgt
atgtgcccacagtgtttgagaactatgtggcagatatcgaggtggatgga
aagcaggtagagttggctttgtgggacacagctgggcaggaagattatga
tcgcctgaggccctctcctacccagataccgatgttatactgatgtgtt
tttccatcgacagccctgatagtttagaaaacatcccagaaaagtggacc
ccagaagtcaagcatttctgtcccaacgtgcccatcatcctggttgggaa
taagaaggatcttcggaatgatgagcacacaaggcgggagctagccaaga
tgaagcaggagccggtgaaacctgaagaaggcagagatatggcaaacagg
attggcgcttttgggtacatggagtgttcagcaaagaccaaagatggagt
gagagaggttttttgaaatggctacgagagctgctctgcaagctagacgtg
ggaagaaaaaatctgggtgccttgtcttgtga SEQ ID NO: 10 Human RHOA G17E cDNA sequence,
variant 1
atggctgccatccggaagaaactggtgattgttggtgatggagcctgtGA
Aaagacatgcttgctcatagtcttcagcaaggaccagttcccagaggtgt
atgtgcccacagtgtttgagaactatgtggcagatatcgaggtggatgga
aagcaggtagagttggctttgtgggacacagctgggcaggaagattatga
tcgcctgaggccctctcctacccagataccgatgttatactgatgtgtt
tttccatcgacagccctgatagtttagaaaacatcccagaaaagtggacc
ccagaagtcaagcatttctgtcccaacgtgcccatcatcctggttgggaa
taagaaggatcttcggaatgatgagcacacaaggcgggagctagccaaga
tgaagcaggagccggtgaaacctgaagaaggcagagatatggcaaacagg
attggcgcttttgggtacatggagtgttcagcaaagaccaaagatggagt
gagagaggttttttgaaatggctacgagagctgctctgcaagctagacgtg
ggaagaaaaaatctgggtgccttgtcttgtga TABLE 3-continued cDNA sequences of RHOA dominant negative forms SEQ ID NO: 11 Human RHOA G17E cDNA sequence,
variant 2
atggctgccatccggaagaaactggtgattgttggtgatggagcctgtGA
Gaagacatgcttgctcatagtcttcagcaaggaccagttcccagaggtgt
atgtgcccacagtgtttgagaactatgtggcagatatcgaggtggatgga
aagcaggtagagttggctttgtgggacacagctgggcaggaagattatga
tcgcctgaggccctctcctacccagataccgatgttatactgatgtgtt
tttccatcgacagccctgatagtttagaaaacatcccagaaaagtggacc
ccagaagtcaagcatttctgtcccaacgtgcccatcatcctggttgggaa
taagaaggatcttcggaatgatgagcacacaaggcgggagctagccaaga
tgaagcaggagccggtgaaacctgaagaaggcagagatatggcaaacagg
attggcgcttttgggtacatggagtgttcagcaaagaccaaagatggagt
gagagaggttttttgaaatggctacgagagctgctctgcaagctagacgtg
ggaagaaaaaatctgggtgccttgtcttgtga Included in Table 2 are polypeptide molecules comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with an amino acid sequence of any SEQ ID NO listed in Table 2, or a portion thereof. Such polypeptides can have a function of the full-length polypeptide as described further herein, such as reducing the number of viable or proliferating cells in the cancer, and/or reduces the volume or size of a tumor comprising the cancer cells. Polypeptides with or without signal peptides, and/or including or only the proprotein, and/or including or only the mature protein are further included.

Included in Table 3 are RNA nucleic acid molecules (e.g., thymines replaced with uredines), as well as DNA or RNA nucleic acid sequences comprising a nucleic acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with the nucleic acid sequence of any SEQ ID NO listed in Table 3, or a portion thereof. Such nucleic acid molecules can have a function of the full-length nucleic acid as described further herein, such as encoding a protein that reduces the number of viable or proliferating cells in the cancer, and/or reduces the volume or size of a tumor comprising the cancer cells. Nucleic acids encoding the polypeptides with or without signal peptides, and/or including or only the proprotein, and/or including or only the mature protein are further included.

II. Agents and Compositions a. Isolated Nucleic Acids

One aspect of the present invention pertains to methods utilizing isolated nucleic acid molecules that encode a RHOA dominant negative polypeptide, or biologically active portions thereof. As used herein, the term "nucleic acid molecule" is intended to include DNA molecules (i.e., cDNA or genomic DNA) and RNA molecules (i.e., mRNA) and analogs of the DNA or RNA generated using nucleotide analogs. The nucleic acid molecule can be single-stranded or double-stranded, but preferably is double-stranded DNA. An "isolated" nucleic acid molecule is one which is separated from other nucleic acid molecules which are present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated nucleic acid molecule that encodes a RHOA dominant negative polypeptide, or biologically active portions thereof, can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived (e.g., cancer cells harboring the RHOA dominant negative mutations). Moreover, an "isolated" nucleic acid molecule, such as a cDNA molecule, can be substantially free of other cellular material, or culture medium when produced by recombinant techniques, or chemical precursors or other chemicals when chemically synthesized.

A nucleic acid molecule that encodes a RHOA dominant negative polypeptide, or biologically active portions thereof, of the present invention, e.g., a nucleic acid molecule having the nucleotide sequence of SEQ ID NO 4, 5, 6, 7, 8, 9, 10, or 11, or a nucleotide sequence which is at least about 50%, preferably at least about 60%, more preferably at least about 70%, yet more preferably at least about 80%, still more preferably at least about 90%, and most preferably at least about 95% or more (e.g., about 98%) homologous to the nucleotide sequence shown in SEQ ID NO 4, 5, 6, 7, 8, 9, 10, or 11, or a portion thereof (i.e., 100, 200, 300, 400, 450, 500, or more nucleotides), can be isolated using standard molecular biology techniques and the sequence information provided herein. For example, a human RHOA domain negative mutant cDNA can be isolated from a human cancer cell line using all or portion of SEQ ID NO 4, 5, 6, 7, 8, 9, 10, or 11, or fragment thereof, as a hybridization probe and standard hybridization techniques (i.e., as described in Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N Y, 1989). Moreover, a nucleic acid molecule encompassing all or a portion of SEQ ID NO 4, 5, 6, 7, 8, 9, 10, or 11, or a nucleotide sequence which is at least about 50%, preferably at least about 60%, more preferably at least about 70%, yet more preferably at least about 80%, still more preferably at least about 90%, and most preferably at least about 95% or more homologous to the nucleotide sequence shown in SEQ ID NO 4, 5, 6, 7, 8, 9, 10, or 11, or fragment thereof, can be isolated by the polymerase chain reaction using oligonucleotide primers designed based upon the sequence of SEQ ID NO 4, 5, 6, 7, 8, 9, 10, or 11, or fragment thereof, or the homologous nucleotide sequence. For example, mRNA can be isolated from cancer cells (i.e., by the guanidinium-thiocyanate extraction procedure of Chirgwin et al. (1979) *Biochemistry* 18: 5294-5299) and cDNA can be prepared using reverse transcriptase (i.e., Moloney MLV reverse transcriptase, available from Gibco/BRL, Bethesda, MD; or AMV reverse transcriptase, available from Seikagaku America, Inc., St. Petersburg, FL). Synthetic oligonucleotide primers for PCR amplification can be designed based upon the nucleotide sequence shown in SEQ ID NO 4, 5, 6, 7, 8, 9, 10, or 11, or fragment thereof, or to the homologous nucleotide sequence. A nucleic acid of the invention can be amplified using cDNA or, alternatively, genomic DNA, as a template and appropriate oligonucleotide primers according to standard PCR amplification techniques. In addition, a nucleic acid of the invention can be generated by site-directed mutagenesis technique using cDNA, or genomic DNA of wild-type RHOA as a template and specific oligonucleotide primers that contain the intented mutation. The nucleic acid so amplified or generated can be cloned into an appropriate vector and characterized by DNA sequence analysis. Furthermore, oligonucleotides corresponding to a RHOA dominant negative mutant nucleotide sequence can be prepared by standard synthetic techniques, i.e., using an automated DNA synthesizer.

Probes based on the RHOA dominant negative mutant nucleotide sequences can be used to detect transcripts or genomic sequences encoding the same or homologous proteins. In preferred embodiments, the probe further comprises a label group attached thereto, i.e., the label group can be a radioisotope, a fluorescent compound, an enzyme, or an enzyme co-factor. Such probes can be used as a part of a diagnostic test kit for identifying cells or tissue which express a RHOA dominant negative polypeptide, such as by measuring a level of a RHOA dominant negative polypeptide-encoding nucleic acid in a sample of cells from a subject, i.e., detecting mRNA levels of RHOA dominant negative polypeptides.

Nucleic acid molecules encoding other RHOA dominant negative mutants and thus having a nucleotide sequence which differs from the sequences of SEQ ID NOs 4-11, or fragment thereof, are contemplated. Moreover, nucleic acid molecules encoding RHOA dominant negative mutants from different species, and thus which have a nucleotide sequence which differs from the sequences of SEQ ID NOs 4-11 are also intended to be within the scope of the present invention. For example, chimpanzee or monkey RHOA dominant negative mutant cDNA can be identified based on the nucleotide sequence of a human and/or mouse RHOA dominant negative mutant.

In one embodiment, the nucleic acid molecule(s) of the invention encodes a protein or portion thereof which includes an amino acid sequence which is sufficiently homologous to an amino acid sequence of SEQ ID NO 1, 2, or 3, or fragment thereof, such that the protein or portion thereof reduces the number of viable or proliferating cells in the cancer, and/or reduces the volume or size of a tumor comprising the cancer cells. Methods and assays for measuring each such biological activity are well-known in the art and representative, non-limiting embodiments are described in the Examples below and Definitions above.

As used herein, the language "sufficiently homologous" refers to proteins or portions thereof which have amino acid sequences which include a minimum number of identical or equivalent (e.g., an amino acid residue which has a similar side chain as an amino acid residue in SEQ ID NO 1, 2, or 3, or fragment thereof) amino acid residues to an amino acid sequence of SEQ ID NO 1, 2, or 3, or fragment thereof, such that the protein or portion thereof reduces the number of viable or proliferating cells in the cancer, and/or reduces the volume or size of a tumor comprising the cancer cells.

In another embodiment, the protein is at least about 50%, preferably at least about 60%, more preferably at least about 70%, 75%, 80%, 85%, 90%, 91%, 92%, 93%, 94%, 95%, 96%, 97%, 98%, 99% or more homologous to the entire amino acid sequence of SEQ ID NO 1, 2, or 3, or a fragment thereof.

Portions of proteins encoded by the RHOA dominant negative mutant nucleic acid molecule of the present invention are preferably biologically active portions of the RHOA dominant negative polypeptide. As used herein, the term "biologically active portion of RHOA dominant negative polypeptide" is intended to include a portion, e.g., a domain/motif, of RHOA dominant negative polypeptide that has one or more of the biological activities of the full-length RHOA dominant negative polypeptide, respectively.

Standard binding assays, e.g., immunoprecipitations and yeast two-hybrid assays, as described herein, or functional assays, e.g., RNAi or overexpression experiments, can be performed to determine the ability of a RHOA dominant negative polypeptide or a biologically active fragment thereof to maintain a biological activity of the full-length RHOA dominant negative polypeptide.

The invention further encompasses nucleic acid molecules that differ from the nucleotide sequence shown in SEQ ID NO 4, 5, 6, 7, 8, 9, 10, or 11, or fragment thereof due to degeneracy of the genetic code and thus encode the same RHOA dominant negative polypeptide as that encoded by the nucleotide sequence shown in SEQ ID NO 4, 5, 6, 7, 8, 9, 10, or 11, or fragment thereof. In another embodiment, an isolated nucleic acid molecule of the invention has a nucleotide sequence encoding a protein having an amino acid sequence shown in SEQ ID NO 1, 2, or 3, or fragment thereof, or a protein having an amino acid sequence which is at least about 70%, 75%, 80%, 85%, 90%, 91%, 92%, 93%, 94%, 95%, 96%, 97%, 98%, 99% or more homologous to the amino acid sequence of SEQ ID NO 1, 2, or 3, or fragment thereof, or differs by at least 1, 2, 3, 5 or 10 amino acids but not more than 30, 20, 15 amino acids from SEQ ID NO 1, 2, or 3. In another embodiment, a nucleic acid encoding a RHOA dominant negative polypeptide consists of nucleic acid sequence encoding a portion of a full-length RHOA dominant negative polypeptide fragment of interest that is less than 195, 190, 185, 180, 175, 170, 165, 160, 155, 150, 145, 140, 135, 130, 125, 120, 115, 110, 105, 100, 95, 90, 85, 80, 75, or 70 amino acids in length.

It will be appreciated by those skilled in the art that DNA sequence polymorphisms that lead to changes in the amino acid sequences of RHOA dominant negative polypeptides may exist within a population (e.g., a mammalian population, e.g., a human population). Such genetic polymorphism in the dominant negative RHOA gene may exist among individuals within a population due to natural allelic variation. As used herein, the terms "gene" and "recombinant gene" refer to nucleic acid molecules comprising an open reading frame encoding a dominant negative RHOA protein, preferably a mammalian, e.g., human, dominant negative RHOA protein. Such natural allelic variations can typically result in 1-5% variance in the nucleotide sequence of the dominant negative RHOA gene. Any and all such nucleotide variations and resulting amino acid polymorphisms in dominant negative RHOA that are the result of natural allelic variation and that do not alter the functional activity of dominant negative RHOA are intended to be within the scope of the invention. Moreover, nucleic acid molecules encoding dominant negative RHOA proteins from other species, and thus which have a nucleotide sequence which differs from the sequences of SEQ ID NOs 4-11, are intended to be within the scope of the invention. Nucleic acid molecules corresponding to natural allelic variants and homologues of the human or mouse dominant negative RHOA cDNAs of the present invention can be isolated based on their homology to the human or mouse dominant negative RHOA nucleic acid sequences disclosed herein using the human or mouse cDNA, or a portion thereof, as a hybridization probe according to standard hybridization techniques under stringent hybridization conditions (as described herein).

In addition to naturally-occurring allelic variants of the RHOA dominant negative mutant sequence that may exist in the population, the skilled artisan will further appreciate that changes can be introduced by mutation into the nucleotide sequence of SEQ ID NO 4, 5, 6, 7, 8, 9, 10, or 11, or fragment thereof, thereby leading to changes in the amino acid sequence of the encoded RHOA dominant negative polypeptide, without altering the functional ability of the RHOA dominant negative polypeptide. For example, nucleotide substitutions leading to amino acid substitutions at "non-essential" amino acid residues can be made in the sequence of SEQ ID NO 1, 2, or 3, or fragment thereof. A "non-essential" amino acid residue is a residue that can be altered from the sequence of RHOA dominant negative polypeptide (e.g., the sequence of SEQ ID NO 1, 2, or 3, or fragment thereof) without significantly altering the activity of RHOA dominant negative polypeptide, whereas an "essential" amino acid residue is required for RHOA dominant negative polypeptide activity. Other amino acid residues, however, (e.g., those that are not conserved or only semi-conserved between mouse and human) may not be essential for activity and thus are likely to be amenable to alteration without altering RHOA dominant negative polypeptide activity. Furthermore, amino acid residues that are essential for RHOA dominant negative polypeptide functions related to cancer cell variability and/or proliferation, but not essential for other RHOA dominant negative polypeptide functions, are likely to be amenable to alteration.

Accordingly, another aspect of the present invention pertains to nucleic acid molecules encoding RHOA dominant negative polypeptides that contain changes in amino acid residues that are not essential for RHOA dominant negative polypeptide activity. Such RHOA dominant negative polypeptides differ in amino acid sequence from SEQ ID NO 1, 2, or 3, or fragment thereof, yet retain at least one of the RHOA dominant negative polypeptide activities described herein. In one embodiment, the isolated nucleic acid molecule comprises a nucleotide sequence encoding a protein, wherein the protein lacks one or more RHOA dominant negative polypeptide domains. As stated in the Definitions section, the structure-function relationship of RHOA dominant negative polypeptide is known such that the ordinarily skilled artisan readily understands the regions that may be mutated or otherwise altered while preserving at least one biological activity of RHOA dominant negative polypeptide.

"Sequence identity or homology", as used herein, refers to the sequence similarity between two polypeptide molecules or between two nucleic acid molecules. When a position in both of the two compared sequences is occupied by the same base or amino acid monomer subunit, e.g., if a position in each of two DNA molecules is occupied by adenine, then the molecules are homologous or sequence identical at that position. The percent of homology or sequence identity between two sequences is a function of the number of matching or homologous identical positions shared by the two sequences divided by the number of positions compared×100. For example, if 6 of 10, of the positions in two sequences are the same then the two sequences are 60% homologous or have 60% sequence identity. By way of example, the DNA sequences ATTGCC and TATGGC share 50% homology or sequence identity. Generally, a comparison is made when two sequences are aligned to give maximum homology. Unless otherwise specified "loop out regions", e.g., those arising from deletions or insertions in one of the sequences are counted as mismatches.

The comparison of sequences and determination of percent homology between two sequences can be accomplished using a mathematical algorithm. Preferably, the alignment can be performed using the Clustal Method. Multiple alignment parameters include GAP Penalty=10, Gap Length Penalty=10. For DNA alignments, the pairwise alignment parameters can be Htuple=2, Gap penalty=5, Window=4, and Diagonal saved=4. For protein alignments, the pairwise alignment parameters can be Ktuple=1, Gap penalty=3, Window=5, and Diagonals Saved=5.

In a preferred embodiment, the percent identity between two amino acid sequences is determined using the Needleman and Wunsch (*J. Mol. Biol.* (48):444-453 (1970)) algorithm which has been incorporated into the GAP program in the GCG software package (available online), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available online), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (CABIOS, 4:11-17 (1989)) which has been incorporated into the ALIGN program (version 2.0) (available online), using a PAM120 weight residue table, a gap length penalty of 12 and a gap penalty of 4.

An isolated nucleic acid molecule encoding a RHOA dominant negative polypeptide homologous to the protein of SEQ ID NO 1, 2, or 3, or fragment thereof, can be created by introducing one or more nucleotide substitutions, additions or deletions into the nucleotide sequence of SEQ ID NO 4, 5, 6, 7, 8, 9, 10, or 11, or fragment thereof, or a homologous nucleotide sequence such that one or more amino acid substitutions, additions or deletions are introduced into the encoded protein. Mutations can be introduced into SEQ ID NO 4, 5, 6, 7, 8, 9, 10, or 11, or fragment thereof, or the homologous nucleotide sequence by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), bet217-420 ranched side chains (e.g., threonine, valine, isoleucine) and aromatic side chains (e.g., tyrosine, phenylalanine, tryptophan, histidine). Thus, a predicted nonessential amino acid residue in RHOA dominant negative polypeptide is preferably replaced with another amino acid residue from the same side chain family. Alternatively, in another embodiment, mutations can be introduced randomly along all or part of a RHOA dominant negative polypeptide coding sequence, such as by saturation mutagenesis, and the resultant mutants can be screened for RHOA dominant negative polypeptide activity described herein to identify mutants that retain RHOA dominant negative polypeptide activity. Following mutagenesis of SEQ ID NO 4, 5, 6, 7, 8, 9, 10, or 11, or fragment thereof, the encoded protein can be expressed recombinantly (as described herein) and the activity of the protein can be determined using, for example, assays described herein.

RHOA dominant negative polypeptide levels may be assessed by any of a wide variety of well-known methods for detecting expression of a transcribed molecule or protein. Non-limiting examples of such methods include immunological methods for detection of proteins, protein purification methods, protein function or activity assays, nucleic acid hybridization methods, nucleic acid reverse transcription methods, and nucleic acid amplification methods.

In preferred embodiments, RHOA dominant negative polypeptide levels are ascertained by measuring gene transcript (e.g., mRNA), by a measure of the quantity of translated protein, or by a measure of gene product activity. Expression levels can be monitored in a variety of ways, including by detecting mRNA levels, protein levels, or protein activity, any of which can be measured using standard techniques. Detection can involve quantification of the level of gene expression (e.g., genomic DNA, cDNA, mRNA, protein, or enzyme activity), or, alternatively, can be a qualitative assessment of the level of gene expression, in particular in comparison with a control level. The type of level being detected will be clear from the context.

In a particular embodiment, the RHOA dominant negative polypeptide mRNA expression level can be determined both by in situ and by in vitro formats in a biological sample using methods known in the art. The term "biological sample" is intended to include tissues, cells, biological fluids and isolates thereof, isolated from a subject, as well as tissues, cells and fluids present within a subject. Many expression detection methods use isolated RNA. For in vitro methods, any RNA isolation technique that does not select against the isolation of mRNA can be utilized for the purification of RNA from cells (see, e.g., Ausubel et al., ed., *Current Protocols in Molecular Biology*, John Wiley & Sons, New York 1987-1999). Additionally, large numbers of tissue samples can readily be processed using techniques well known to those of skill in the art, such as, for example, the single-step RNA isolation process of Chomczynski (1989, U.S. Pat. No. 4,843,155).

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length cDNA, or a portion thereof, such as an oligonucleotide of at least 7, 15, 30, 50, 100, 250 or 500 nucleotides in length and sufficient to specifically hybridize under stringent conditions to a mRNA or genomic DNA encoding RHOA dominant negative polypeptide. Other suitable probes for use in the diagnostic assays of the invention are described herein. Hybridization of an mRNA with the probe indicates that RHOA dominant negative polypeptide is being expressed.

In one format, the mRNA is immobilized on a solid surface and contacted with a probe, for example by running the isolated mRNA on an agarose gel and transferring the mRNA from the gel to a membrane, such as nitrocellulose. In an alternative format, the probe(s) are immobilized on a solid surface and the mRNA is contacted with the probe(s), for example, in a gene chip array, e.g., an Affymetrix™ gene chip array. A skilled artisan can readily adapt known mRNA detection methods for use in detecting the level of the RHOA dominant negative mRNA expression levels.

An alternative method for determining the RHOA dominant negative mRNA expression level in a sample involves the process of nucleic acid amplification, e.g., by rtPCR (the experimental embodiment set forth in Mullis, 1987, U.S. Pat. No. 4,683,202), ligase chain reaction (Barany, 1991, *Proc. Natl. Acad. Sci. USA,* 88:189-193), self-sustained sequence replication (Guatelli et al., 1990, *Proc. Natl. Acad. Sci. USA* 87:1874-1878), transcriptional amplification system (Kwoh et al., 1989, *Proc. Natl. Acad. Sci. USA* 86:1173-1177), Q-Beta Replicase (Lizardi et al., 1988, *Bio/Technology* 6:1197), rolling circle replication (Lizardi et al., U.S. Pat. No. 5,854,033) or any other nucleic acid amplification method, followed by the detection of the amplified molecules using techniques well-known to those of skill in the art. These detection schemes are especially useful for the detection of nucleic acid molecules if such molecules are present in very low numbers. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, mRNA does not need to be isolated from the cells prior to detection. In such methods, a cell or tissue sample is prepared/processed using known histological methods. The sample is then immobilized on a support, typically a glass slide, and then contacted with a probe that can hybridize to the RHOA dominant negative mRNA.

As an alternative to making determinations based on the absolute RHOA dominant negative polypeptide expression level, determinations may be based on the normalized RHOA dominant negative polypeptide expression level. Expression levels are normalized by correcting the absolute RHOA dominant negative polypeptide expression level by comparing its expression to the expression of a non-RHOA dominant negative polypeptide gene, e.g., a housekeeping gene that is constitutively expressed. Suitable genes for normalization include housekeeping genes such as the actin gene, or epithelial cell-specific genes. This normalization allows the comparison of the expression level in one sample, e.g., a subject sample, to another sample, e.g., a normal sample, or between samples from different sources.

The level or activity of a RHOA dominant negative mutant can also be detected and/or quantified by detecting or quantifying the expressed polypeptide. The RHOA dominant negative polypeptide can be detected and quantified by any of a number of means well known to those of skill in the art. These may include analytic biochemical methods such as electrophoresis, capillary electrophoresis, high performance liquid chromatography (HPLC), thin layer chromatography (TLC), hyperdiffusion chromatography, and the like, or various immunological methods such as fluid or gel precipitin reactions, immunodiffusion (single or double), immunoelectrophoresis, radioimmunoassay (RIA), enzyme-linked immunosorbent assays (ELISAs), immunofluorescent assays, Western blotting, and the like. A skilled artisan can readily adapt known protein/antibody detection methods for use in determining whether cells express RHOA dominant negative polypeptide.

b. Recombinant Expression Vectors and Host Cells

Another aspect of the invention pertains to the use of vectors, preferably expression vectors, containing a nucleic acid encoding a RHOA dominant negative polypeptide (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions. In one embodiment, adenoviral vectors comprising a dominant negative RHOA nucleic acid molecule are used.

The recombinant expression vectors of the present invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; *Gene Expression Technology: Methods in Enzymology* 185, Academic Press, San Diego, CA (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein.

The recombinant expression vectors of the invention can be designed for expression of dominant negative RHOA in prokaryotic or eukaryotic cells. For example, dominant negative RHOA can be expressed in bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, CA (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) Gene 67:31-40), pMAL (New England Biolabs, Beverly, MA) and pRIT5 (Pharmacia, Piscataway, NJ) which fuse glutathione S-transferase (GST), maltose E binding protein, or protein A, respectively, to the target recombinant protein. In one embodiment, the coding sequence of dominant negative RHOA is cloned into a pGEX expression vector to create a vector encoding a fusion protein comprising, from the N-terminus to the C-terminus, and/or GST-thrombin cleavage site-dominant negative RHOA. The fusion protein can be purified by affinity chromatography using glutathione-agarose resin. Recombinant RHOA dominant negative polypeptide unfused to GST can be recovered by cleavage of the fusion protein with thrombin.

Examples of suitable inducible non-fusion E. coli expression vectors include pTrc (Amann et al., (1988) Gene 69:301-315) and pET 11d (Studier et al., Gene Expression Technology: Methods in Enzymology 185, Academic Press, San Diego, California (1990) 60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174 (DE3) from a resident λ prophage harboring a T7 gn1 gene under the transcriptional control of the lacUV 5 promoter.

One strategy to maximize recombinant protein expression in E. coli is to express the protein in a host bacteria with an impaired capacity to proteolytically cleave the recombinant protein (Gottesman, S., Gene Expression Technology: Methods in Enzymology 185, Academic Press, San Diego, California (1990) 119-128). Another strategy is to alter the nucleic acid sequence of the nucleic acid to be inserted into an expression vector so that the individual codons for each amino acid are those preferentially utilized in E. coli (Wada et al. (1992) Nucleic Acids Res. 20:2111-2118). Such alteration of nucleic acid sequences of the invention can be carried out by standard DNA synthesis techniques.

In another embodiment, the dominant negative RHOA expression vector is a yeast expression vector. Examples of vectors for expression in yeast S. cerivisae include pYepSec1 (Baldari, et al., (1987) EMBO J. 6:229-234), pMFa (Kurj an and Herskowitz, (1982) Cell 30:933-943), pJRY88 (Schultz et al., (1987) Gene 54:113-123), and pYES2 (Invitrogen Corporation, San Diego, CA).

Alternatively, dominant negative RHOA can be expressed in insect cells using baculovirus expression vectors. Baculovirus vectors available for expression of proteins in cultured insect cells (e.g., Sf 9 cells) include the pAc series (Smith et al. (1983) Mol. Cell Biol. 3:2156-2165) and the pVL series (Lucklow and Summers (1989) Virology 170:31-39).

In yet another embodiment, a nucleic acid of the invention is expressed in mammalian cells using a mammalian expression vector. Examples of mammalian expression vectors include pCDM8 (Seed, B. (1987) Nature 329:840) and pMT2PC (Kaufman et al. (1987) EMBO J. 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. Molecular Cloning: A Laboratory Manual. 2nd, ed., Cold Spring Harbor Laboratory, Cold Spring Harbor Laboratory Press, Cold Spring Harbor, N Y, 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) Genes Dev. 1:268-277), lymphoid-specific promoters (Calame and Eaton (1988) Adv. Immunol. 43:235-275), in particular promoters of T cell receptors (Winoto and Baltimore (1989) EMBO J. 8:729-733) and immunoglobulins (Banerji et al. (1983) Cell 33:729-740; Queen and Baltimore (1983) Cell 33:741-748), neuron-specific promoters (e.g., the neurofilament promoter; Byrne and Ruddle (1989) Proc. Natl. Acad. Sci. USA 86:5473-5477), pancreas-specific promoters (Edlund et al. (1985) Science 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) Science 249:374-379) and the α-fetoprotein promoter (Campes and Tilghman (1989) Genes Dev. 3:537-546).

Another aspect of the present invention pertains to host cells into which a recombinant expression vector or nucleic acid of the present invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, RHOA dominant negative polypeptide can be expressed in bacterial cells such as E. coli, insect cells, yeast or mammalian cells (such as Fao hepatoma cells, primary hepatocytes, Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (Molecular Cloning: A Laboratory Manual. 2nd, ed., Cold Spring Harbor Laboratory, Cold Spring Harbor Laboratory Press, Cold Spring Harbor, N Y, 1989), and other laboratory manuals.

A cell culture includes host cells, media and other byproducts. Suitable media for cell culture are well known in the art. A RHOA dominant negative polypeptide or fragment thereof, may be secreted and isolated from a mixture of cells and medium containing the polypeptide. Alternatively, a RHOA dominant negative polypeptide or fragment thereof, may be retained cytoplasmically and the cells harvested, lysed and the protein or protein complex isolated. A RHOA dominant negative polypeptide or fragment thereof, may be isolated from cell culture medium, host cells, or both using techniques known in the art for purifying proteins, including ion-exchange chromatography, gel filtration chromatography, ultrafiltration, electrophoresis, and inmmunoaffinity purification with antibodies specific for particular epitopes of dominant negative RHOA or a fragment thereof.

In some embodiments, RHOA dominant negative polypeptide, or biologically active fragment thereof, and may be fused to a heterologous polypeptide. In certain embodiments, the fused polypeptide has greater half-life and/or cell permeability than the corresponding unfused RHOA dominant negative polypeptide, or biologically active fragment thereof. For example, RHOA dominant negative polypeptide may be fused to a cell permeable peptide to facilitate the delivery of the RHOA dominant negative polypeptide into the intact cells. Cell Permeable Peptides, also known as Protein Transduction Domains (PTDs), are carriers with small peptide domains that can freely cross cell membranes. Several PTDs have been identified that allow a fused protein to efficiently cross cell membranes in a process known as protein transduction. Studies have demonstrated that a TAT peptide derived from the HIV TAT protein has the ability to transduce peptides or proteins into various cells. PTDs have been utilized in anticancer strategy, for example, a cell permeable Bcl-2 binding peptide, cpm1285, shows activity in slowing human myeloid leukemia growth in mice. Cell-permeable phosphopeptides, such as FGFR730pY, which mimics receptor binding sites for specific SH2 domain-containing proteins are potential tools for cancer research and cell signaling mechanism studies. In other embodiments, heterologous tags can be used for purification purposes (e.g., epitope tags and Fc fusion tags), according to standards methods known in the art.

Thus, a nucleotide sequence encoding all or a selected portion of a RHOA dominant negative polypeptide may be used to produce a recombinant form of the protein via microbial or eukaryotic cellular processes. Ligating the sequence into a polynucleotide construct, such as an expression vector, and transforming or transfecting into hosts, either eukaryotic (yeast, avian, insect or mammalian) or prokaryotic (bacterial cells), are standard procedures. Similar procedures, or modifications thereof, may be employed to prepare recombinant RHOA dominant negative polypeptides, or fragments thereof, by microbial means or tissue-culture technology in accord with the subject invention.

In another variation, protein production may be achieved using in vitro translation systems. In vitro translation systems are, generally, a translation system which is a cell-free extract containing at least the minimum elements necessary for translation of an RNA molecule into a protein. An in vitro translation system typically comprises at least ribosomes, tRNAs, initiator methionyl-tRNAMet, proteins or complexes involved in translation, e.g., eIF2, eIF3, the cap-binding (CB) complex, comprising the cap-binding protein (CBP) and eukaryotic initiation factor 4F (eIF4F). A variety of in vitro translation systems are well known in the art and include commercially available kits. Examples of in vitro translation systems include eukaryotic lysates, such as rabbit reticulocyte lysates, rabbit oocyte lysates, human cell lysates, insect cell lysates and wheat germ extracts. Lysates are commercially available from manufacturers such as Promega Corp., Madison, Wis.; Stratagene, La Jolla, Calif.; Amersham, Arlington Heights, Ill.; and GIBCO/BRL, Grand Island, N.Y. In vitro translation systems typically comprise macromolecules, such as enzymes, translation, initiation and elongation factors, chemical reagents, and ribosomes. In addition, an in vitro transcription system may be used. Such systems typically comprise at least an RNA polymerase holoenzyme, ribonucleotides and any necessary transcription initiation, elongation and termination factors. In vitro transcription and translation may be coupled in a one-pot reaction to produce proteins from one or more isolated DNAs.

In certain embodiments, the RHOA dominant negative polypeptide, or fragment thereof, may be synthesized chemically, ribosomally in a cell free system, or ribosomally within a cell. Chemical synthesis may be carried out using a variety of art recognized methods, including stepwise solid phase synthesis, semi-synthesis through the conformationally-assisted re-ligation of peptide fragments, enzymatic ligation of cloned or synthetic peptide segments, and chemical ligation. Native chemical ligation employs a chemoselective reaction of two unprotected peptide segments to produce a transient thioester-linked intermediate. The transient thioester-linked intermediate then spontaneously undergoes a rearrangement to provide the full length ligation product having a native peptide bond at the ligation site. Full length ligation products are chemically identical to proteins produced by cell free synthesis. Full length ligation products may be refolded and/or oxidized, as allowed, to form native disulfide-containing protein molecules. (see e.g., U.S. Pat. Nos. 6,184,344 and 6,174,530; and T. W. Muir et al., Curr. Opin. Biotech. (1993): vol. 4, p 420; M. Miller, et al., Science (1989): vol. 246, p 1149; A. Wlodawer, et al., Science (1989): vol. 245, p 616; L. H. Huang, et al., Biochemistry (1991): vol. 30, p 7402; M. Sclmolzer, et al., Int. J. Pept. Prot. Res. (1992): vol. 40, p 180-193; K. Rajarathnam, et al., Science (1994): vol. 264, p 90; R. E. Offord, "Chemical Approaches to Protein Engineering", in Protein Design and the Development of New therapeutics and Vaccines, J. B. Hook, G. Poste, Eds., (Plenum Press, New York, 1990) pp. 253-282; C. J. A. Wallace, et al., J. Biol. Chem. (1992): vol. 267, p 3852; L. Abrahmsen, et al., Biochemistry (1991): vol. 30, p 4151; T. K. Chang, et al., Proc. Natl. Acad. Sci. USA (1994) 91: 12544-12548; M. Schnlzer, et al., Science (1992): vol., 3256, p 221; and K. Akaji, et al., Chem. Pharm. Bull. (Tokyo) (1985) 33: 184).

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding dominant negative RHOA or can be introduced on a separate vector. Cells stably transfected with the introduced nucleic acid can be identified by drug selection (e.g., cells that have incorporated the selectable marker gene will survive, while the other cells die).

A host cell of the present invention, such as a prokaryotic or eukaryotic host cell in culture, can be used to produce (i.e., express) RHOA dominant negative polypeptide. Accordingly, the invention further provides methods for producing RHOA dominant negative polypeptide using the host cells of the invention. In one embodiment, the method comprises culturing the host cell of invention (into which a recombinant expression vector encoding dominant negative RHOA has been introduced) in a suitable medium until RHOA dominant negative polypeptide is produced. In another embodiment, the method further comprises isolating RHOA dominant negative polypeptide from the medium or the host cell.

The host cells of the invention can also be used to produce human or non-human transgenic animals and/or cells that, for example, overexpress RHOA dominant negative polypeptide or oversecrete RHOA dominant negative polypeptide. The non-human transgenic animals can be used in screening assays designed to identify agents or compounds, e.g., drugs, pharmaceuticals, etc., which are capable of ameliorating detrimental symptoms of selected disorders such as diffuse gastric cancer (DGC), lobular breast cancer, or other types of EMT cancers. For example, in one embodiment, a host cell of the present invention is a fertilized oocyte or an embryonic stem cell into which dominant negative RHOA-encoding sequences, or fragments thereof, have been introduced. Such host cells can then be used to create non-human transgenic animals in which exogenous dominant negative RHOA sequences have been introduced into their genome or homologous recombinant animals in which endogenous RHOA sequences have been altered. Such animals are useful for studying the function and/or activity of dominant negative RHOA, or fragments thereof, and for identifying and/or evaluating modulators of dominant negative RHOA activity. As used herein, a "transgenic animal" is a non-human animal, preferably a mammal, more preferably a rodent such as a rat or mouse, in which one or more of the cells of the animal includes a transgene. Other examples of transgenic animals include nonhuman primates, sheep, dogs, cows, goats, chickens, amphibians, etc. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a nonhuman animal, preferably a mammal, more preferably a mouse, in which an endogenous RHOA gene has been altered by homologous recombination between the endogenous gene and an exogenous DNA molecule introduced into a cell of the animal, e.g., an embryonic cell of the animal, prior to development of the animal.

A transgenic animal of the present invention can be created by introducing nucleic acids encoding dominant negative RHOA, or a fragment thereof, into the male pronuclei of a fertilized oocyte, e.g., by microinjection, retroviral infection, and allowing the oocyte to develop in a pseudopregnant female foster animal. The human dominant negative RHOA cDNA sequence can be introduced as a transgene into the genome of a nonhuman animal. Alternatively, a nonhuman homologue of the human dominant negative RHOA gene can be used as a transgene. Intronic sequences and polyadenylation signals can also be included in the transgene to increase the efficiency of expression of the transgene. A tissue-specific regulatory sequence(s) can be operably linked to the dominant negative RHOA transgene to direct expression of RHOA dominant negative polypeptide to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the dominant negative RHOA transgene in its genome and/or expression of dominant negative RHOA mRNA in tissues or cells of the animals. A transgenic founder animal can then be used to breed additional animals carrying the transgene. Moreover, transgenic animals carrying a transgene encoding dominant negative RHOA can further be bred to other transgenic animals carrying other transgenes.

To create a homologous recombinant animal, a vector is prepared which contains at least a portion of a dominant negative RHOA gene. The dominant negative RHOA gene can be a human gene, or a nonhuman homologue of a human dominant negative RHOA gene. For example, a human dominant negative RHOA gene can be used to construct a homologous recombination vector suitable for altering an endogenous RHOA gene, in the mouse genome. In the homologous recombination vector, the dominant negative mutations of the dominant negative RHOA gene is flanked at its 5' and 3' ends by additional nucleic acid of the RHOA gene to allow for homologous recombination to occur between the exogenous dominant negative RHOA gene carried by the vector and an endogenous RHOA gene in an embryonic stem cell. The additional flanking RHOA nucleic acid is of sufficient length for successful homologous recombination with the endogenous gene. Typically, several kilobases of flanking DNA (both at the 5' and 3' ends) are included in the vector (see e.g., Thomas, K. R. and Capecchi, M. R. (1987) *Cell* 51:503 for a description of homologous recombination vectors). The vector is introduced into an embryonic stem cell line (e.g., by electroporation) and cells in which the introduced dominant negative RHOA gene has homologously recombined with the endogenous RHOA gene are selected (see e.g., Li, E. et al. (1992) *Cell* 69:915). The selected cells are then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley (1991) *Current Opinion in Biotechnology* 2:823-829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In another embodiment, transgenic nonhuman animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *Proc. Natl. Acad. Sci. USA* 89:6232-6236. Another example of a recombinase system is the FLP recombinase system of *Saccharomyces cerevisiae* (O'Gorman et al. (1991) *Science*

251:1351-1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the nonhuman transgenic animals described herein can also be produced according to the methods described in Wilmut, I. et al. (1997) *Nature* 385:810-813 and PCT International Publication Nos. WO 97/07668 and WO 97/07669. In brief, a cell, e.g., a somatic cell, from the transgenic animal can be isolated and induced to exit the growth cycle and enter $G_O$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring borne of this female foster animal will be a clone of the animal from which the cell, e.g., the somatic cell, is isolated.

c. Isolated RHOA Dominant Negative Polypeptides

The present invention also provides soluble, purified and/or isolated forms of RHOA dominant negative polypeptide, or fragments thereof for use according to methods described herein.

In one aspect, a RHOA dominant negative polypeptide may comprise a full-length dominant negative RHOA amino acid sequence or a full-length dominant negative RHOA amino acid sequence with 1 to about 20 conservative amino acid substitutions. Amino acid sequence of any RHOA dominant negative polypeptide described herein can also be at least 50, 55, 60, 65, 70, 75, 80, 85, 90, 91, 92, 93, 94, 95, 96, 97, 98, 99, or 99.5% identical to an RHOA dominant negative polypeptide sequence of interest, described herein, well known in the art, or a fragment thereof. In addition, any RHOA dominant negative polypeptide, or fragment thereof, described herein can modulate (e.g., reduce) one or more of the following biological activities: cancer cell survival, cancer cell proliferation, and tumor size/volume.

In another aspect, the present invention contemplates a composition comprising an isolated RHOA dominant negative polypeptide and less than about 25%, or alternatively 15%, or alternatively 5%, contaminating biological macromolecules or polypeptides.

The present invention further provides compositions related to producing, detecting, or characterizing a RHOA dominant negative polypeptide, or fragment thereof, such as nucleic acids, vectors, host cells, and the like. Such compositions may serve as compounds that modulate a RHOA dominant negative polypeptide's expression and/or activity, such as antisense nucleic acids.

In certain embodiments, a RHOA dominant negative polypeptide of the invention may be a fusion protein containing a domain which increases its solubility and bioavailability and/or facilitates its purification, identification, detection, and/or structural characterization. In some embodiments, it may be useful to express a RHOA dominant negative fusion polypeptides in which the fusion partner enhances fusion protein stability in blood plasma and/or enhances systemic bioavailability. Exemplary domains, include, for example, glutathione S-transferase (GST), protein A, protein G, calmodulin-binding peptide, thioredoxin, maltose binding protein, HA, myc, poly arginine, poly His, poly His-Asp or FLAG fusion proteins and tags. Additional exemplary domains include domains that alter protein localization in vivo, such as signal peptides, type 21 secretion system-targeting peptides, transcytosis domains, nuclear localization signals, etc. In various embodiments, a RHOA dominant negative polypeptide of the invention may comprise one or more heterologous fusions. Polypeptides may contain multiple copies of the same fusion domain or may contain fusions to two or more different domains. The fusions may occur at the N-terminus of the polypeptide, at the C-terminus of the polypeptide, or at both the N- and C-terminus of the polypeptide. It is also within the scope of the invention to include linker sequences between a polypeptide of the invention and the fusion domain in order to facilitate construction of the fusion protein or to optimize protein expression or structural constraints of the fusion protein. In one embodiment, the linker is a linker described herein, e.g., a linker of at least 1, 2, 3, 4, 5, 6, 7, 8, 9, 10, 15, 20 or more amino acids. The linker can be, e.g., an unstructured recombinant polymer (URP), e.g., a URP that is 9, 10, 11, 12, 13, 14, 15, 20 amino acids in length, i.e., the linker has limited or lacks secondary structure, e.g., Chou-Fasman algorithm. An exemplary linker comprises (e.g., consists of) the amino acid sequence GGGGAGGGG. In another embodiment, the polypeptide may be constructed so as to contain protease cleavage sites between the fusion polypeptide and polypeptide of the invention in order to remove the tag after protein expression or thereafter. Examples of suitable endoproteases, include, for example, Factor Xa and TEV proteases.

In some embodiments, RHOA dominant negative polypeptides, or fragments thereof, are fused to an antibody (e.g., IgG1, IgG2, IgG3, IgG4) fragment (e.g., Fc polypeptides). Techniques for preparing these fusion proteins are known, and are described, for example, in WO 99/31241 and in Cosman et.al. (2001) *Immunity* 14:123-133. Fusion to an Fc polypeptide offers the additional advantage of facilitating purification by affinity chromatography over Protein A or Protein G columns.

In still another embodiment, a RHOA dominant negative polypeptide may be labeled with a fluorescent label to facilitate their detection, purification, or structural characterization. In an exemplary embodiment, a RHOA dominant negative polypeptide of the invention may be fused to a heterologous polypeptide sequence which produces a detectable fluorescent signal, including, for example, green fluorescent protein (GFP), enhanced green fluorescent protein (EGFP), *Renilla Reniformis* green fluorescent protein, GFPmut2, GFPuv4, enhanced yellow fluorescent protein (EYFP), enhanced cyan fluorescent protein (ECFP), enhanced blue fluorescent protein (EBFP), citrine and red fluorescent protein from discosoma (dsRED).

An "isolated" or "purified" protein or biologically active portion thereof is substantially free of cellular material when produced by recombinant DNA techniques, or chemical precursors or other chemicals when chemically synthesized. The language "substantially free of cellular material" includes preparations of RHOA dominant negative polypeptide in which the polypeptide is separated from cellular components of the cells in which it is naturally or recombinantly produced. In one embodiment, the language "substantially free of cellular material" includes preparations of RHOA dominant negative polypeptide having less than about 30% (by dry weight) of non-RHOA dominant negative polypeptide (also referred to herein as a "contaminating protein"), more preferably less than about 20% of non-RHOA dominant negative polypeptide, still more preferably less than about 10% of non-RHOA dominant negative polypeptide, and most preferably less than about 5% non-RHOA dominant negative polypeptide. When the RHOA dominant negative polypeptide or biologically active portion thereof is recombinantly produced, it is also preferably substantially free of culture medium, i.e., culture medium represents less than about 20%, more preferably less than about 10%, and most preferably less than about 5% of the volume of the protein preparation. The language "substantially free of chemical precursors or other chemicals" includes preparations of RHOA dominant negative polypeptide in which the polypeptide is separated from chemical precursors or other chemicals which are involved in the synthesis of the polypeptide. In one embodiment, the language "substantially free of chemical precursors or other chemicals" includes preparations of RHOA dominant negative polypeptide having less than about 30% (by dry weight) of chemical precursors of non-RHOA dominant negative polypeptide chemicals, more preferably less than about 20% chemical precursors of non-RHOA dominant negative polypeptide chemicals, still more preferably less than about 10% chemical precursors of non-RHOA dominant negative polypeptide chemicals, and most preferably less than about 5% chemical precursors of non-RHOA dominant negative polypeptide chemicals. In preferred embodiments, isolated polypeptides or biologically active portions thereof lack contaminating polypeptides from the same animal from which the RHOA dominant negative polypeptide is derived. Typically, such polypeptides are produced by recombinant expression of, for example, a human RHOA dominant negative polypeptide in a nonhuman cell.

In preferred embodiments, the protein or portion thereof comprises an amino acid sequence which is sufficiently homologous to an amino acid sequence of SEQ ID NO 1, 2, or 3, or fragment thereof, such that the protein or portion thereof maintains one or more of the following biological activities or, in complex, modulates (e.g., reduce) one or more of the following biological activities: cancer cell survival, cancer cell proliferation, and tumor size/volume. The portion of the protein is preferably a biologically active portion as described herein. In another preferred embodiment, the RHOA dominant negative polypeptides has an amino acid sequence shown in SEQ ID NO 1, 2, or 3, or fragment thereof, respectively, or an amino acid sequence which is at least about 50%, 55%, 60%, 65%, 70%, 75%, 80%, 85%, 90%, 91%, 92%, 93%, 94%, 95%, 96%, 97%, 98%, 99% or more homologous to the amino acid sequence shown in SEQ ID NO 1, 2, or 3, or fragment thereof. In yet another preferred embodiment, the RHOA dominant negative polypeptide has an amino acid sequence which is encoded by a nucleotide sequence which hybridizes, e.g., hybridizes under stringent conditions, to the nucleotide sequence of SEQ ID NO 4, 5, 6, 7, 8, 9, 10, or 11, or fragment thereof, or a nucleotide sequence which is at least about 50%, preferably at least about 60%, more preferably at least about 70%, yet more preferably at least about 80%, still more preferably at least about 90%, and most preferably at least about 95% or more homologous to the nucleotide sequence shown in SEQ ID NO 4, 5, 6, 7, 8, 9, 10, or 11, or fragment thereof. The preferred RHOA dominant negative polypeptides of the present invention also preferably possess at least one of the RHOA dominant negative polypeptide biological activities described herein.

Biologically active portions of a RHOA dominant negative protein include peptides comprising amino acid sequences derived from the amino acid sequence of the RHOA dominant negative protein, e.g., the amino acid sequence shown in SEQ ID NO 1, 2, or 3, or fragment thereof, or the amino acid sequence of a protein homologous to the RHOA dominant negative protein, which include fewer amino acids than the full-length RHOA dominant negative protein or the full-length polypeptide which is homologous to the RHOA dominant negative protein, and exhibit at least one activity of the RHOA dominant negative protein. Typically, biologically active portions (peptides, e.g., peptides which are, for example, 50, 55, 60, 65, 70, 75, 80, 85, 90, 95, 100 or more amino acids in length) comprise a domain or motif, (e.g., the full-length protein minus the signal peptide). In a preferred embodiment, the biologically active portion of the protein which includes one or more the domains/motifs described herein can modulate (e.g., reduce) one ore more the following biological activities: cancer cell survival, cancer cell proliferation, and tumor size/volume. Moreover, other biologically active portions, in which other regions of the protein are deleted, can be prepared by recombinant techniques and evaluated for one or more of the activities described herein. Preferably, the biologically active portions of the RHOA dominant negative protein include one or more selected domains/motifs or portions thereof having biological activity. In one embodiment, a dominant negative RHOA fragment of interest consists of a portion of a full-length dominant negative RHOA protein that is less than 240, 230, 220, 210, 200, 195, 190, 185, 180, 175, 170, 165, 160, 155, 150, 145, 140, 135, 130, 125, 120, 115, 110, 105, 100, 95, 90, 85, 80, 75, or 70 amino acids in length.

RHOA dominant negative proteins can be produced by recombinant DNA techniques. For example, a nucleic acid molecule encoding the protein is cloned into an expression vector (as described above), the expression vector is introduced into a host cell (as described above) and the RHOA dominant negative protein is expressed in the host cell. The RHOA dominant negative protein can then be isolated from the cells by an appropriate purification scheme using standard protein purification techniques. Alternative to recombinant expression, a RHOA dominant negative protein, polypeptide, or peptide can be synthesized chemically using standard peptide synthesis techniques. Moreover, native RHOA dominant negative protein can be isolated from cells (e.g., cancer cells that harboring RHOA dominant negative mutations), for example using an anti-RHOA antibody.

The invention also provides dominant RHOA chimeric or fusion proteins. As used herein, a dominant RHOA "chimeric protein" or "fusion protein" comprises a RHOA dominant negative polypeptide operatively linked to a non-RHOA dominant negative polypeptide. An "RHOA dominant negative polypeptide" refers to a polypeptide having an amino acid sequence corresponding to dominant negative RHOA, whereas a "non-RHOA dominant negative polypeptide" refers to a polypeptide having an amino acid sequence corresponding to a protein which is not substantially homologous to the dominant negative RHOA protein, e.g., a protein which is different from the RHOA dominant negative protein and which is derived from the same or a different organism. Within the fusion protein, the term "operatively linked" is intended to indicate that the RHOA dominant negative polypeptide and the non-RHOA dominant negative polypeptide are fused in-frame to each other. The non-RHOA dominant negative polypeptide can be fused to the N-terminus or C-terminus of the RHOA dominant negative polypeptide. For example, in one embodiment the fusion protein is a dominat negative RHOA-GST and/or dominat negative RHOA-Fc fusion protein in which the dominat negative RHOA sequences, respectively, are fused to the N-terminus of the GST or Fc sequences. Such fusion proteins can be made using dominat negative RHOA polypeptides. Such fusion proteins can also facilitate the purification, expression, and/or bioavailability of recombinant dominat negative RHOA. In another embodiment, the fusion protein is a dominat negative RHOA protein containing a heterologous signal sequence at its C-terminus. In certain host cells (e.g., mammalian host cells), expression and/or secretion of dominat negative RHOA can be increased through use of a heterologous signal sequence.

Preferably, a dominat negative RHOA chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). A dominat negative RHOA-encoding nucleic acid can be cloned into such an expression vector such that the fusion moiety is linked in-frame to the RHOA dominat negative protein.

The present invention also pertains to homologues of the RHOA dominat negative proteins. Homologues of the dominat negative RHOA protein can be generated by mutagenesis, e.g., discrete point mutation or truncation of the dominat negative RHOA protein, respectively. As used herein, the term "homologue" refers to a variant form of the dominant negative RHOA protein. In one embodiment, treatment of a subject with a homologue having a subset of the biological activities of the naturally occurring form of the protein has fewer side effects in a subject relative to treatment with the naturally occurring form of the dominant negative RHOA protein.

In an alternative embodiment, homologues of the dominat negative RHOA protein can be identified by screening combinatorial libraries of mutants, e.g., truncation mutants, of the dominat negative RHOA protein. In one embodiment, a variegated library of dominat negative RHOA variants is generated by combinatorial mutagenesis at the nucleic acid level and is encoded by a variegated gene library. A variegated library of dominat negative RHOA variants can be produced by, for example, enzymatically ligating a mixture of synthetic oligonucleotides into gene sequences such that a degenerate set of potential dominat negative RHOA sequences is expressible as individual polypeptides, or alternatively, as a set of larger fusion proteins (e.g., for phage display) containing the set of dominat negative RHOA sequences therein. There are a variety of methods which can be used to produce libraries of potential dominat negative RHOA homologues from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential dominat negative RHOA sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477.

In addition, libraries of fragments of the dominat negative RHOA protein coding can be used to generate a variegated population of dominat negative RHOA fragments for screening and subsequent selection of homologues of a RHOA dominant negative protein. In one embodiment, a library of coding sequence fragments can be generated by treating a double stranded PCR fragment of an dominat negative RHOA coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with Si nuclease, and ligating the resulting fragment library into an expression vector. By this method, an expression library can be derived which encodes N-terminal, C-terminal and internal fragments of various sizes of the dominat negative RHOA protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of dominat negative RHOA homologues. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify dominat negative RHOA homologues (Arkin and Youvan (1992) *Proc. Natl. Acad. Sci. USA* 89:7811-7815).

III. Methods of Selecting Agents and Compositions

Another aspect of the present invention relates to methods of selecting agents (e.g., a RHOA mutant polypeptide) that reduce viability or proliferation of a cancer cell with a reduced level of CDH1. Such methods can use screening assays, including cell-based and non-cell based assays.

In one embodiment, the invention relates to assays for screening candidate or test compounds which reduce viability or proliferation of a cancer cell with a reduced level of CDH1. Such compounds include, without limitation, RHOA mutant polypeptides.

In one embodiment, an assay is a cell-based assay for screening for agents that reduce viability or proliferation of a cancer cell with a reduced level of CDH1, comprising: a) contacting the cancer cell with a test agent selected from the group consisting of 1) a nucleic acid encoding a RHOA mutant, or biologically active fragment thereof and 2) a RHOA mutant polypeptide, or biologically active fragment thereof; and b) determining a reduced viability or proliferation of the cancer cell relative to a control, thereby identifying the test agent to reduce viability or proliferation of the cancer cell. For example, cellular proliferation or invasion can be determined by monitoring cell number count, cellular movement, matrigel assays, induction of proliferation- and/or invasion-related gene expression, and the like, as described further herein.

In another embodiment, an assay of the present invention is a cell-free assay in which a RHOA mutant polypeptide, or biologically active fragment thereof, are contacted with GTP, and the ability of the test RHOA mutant polypeptide to incorporate GTP, is determined. The uptake of the GTP into the test RHOA mutant polypeptide, can be determined by different methods. For example, a RhoGEF exchange assay kit (cytoskeleton, Inc.) can be used which analyzes the uptake of the fluorescent nucleotide analog N-methylanthraniloyl-GTP (mant-GTP) into RHOA by measuring the spectroscopic difference between free and RHOA-bound mant-GTP. The enhancement of mant-GTP fluorescent intensity in the presence of RHOA indicates nucleotide uptake by the GTPase.

In another aspect, the invention pertains to a combination of two or more of the assays described herein. For example, a modulating agent can be identified using a cell-based or a cell-free assay, and the ability of the agent to reduce viability or proliferation of a cancer cell with a reduced level of CDH1 can be confirmed in vivo, e.g., in an animal such as an animal model for cellular transformation and/or tumorigenesis.

This invention further pertains to novel agents identified by the above-described screening assays. Accordingly, it is within the scope of this invention to further use an agent identified as described herein in an appropriate animal model. For example, an agent identified as described herein can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

IV. Subjects

In one embodiment, the subject for whom an agent reducing viability or proliferation of cancer cells which have a reduced level of CDH1 is administered (e.g., at least one agent selected from the group consisting of 1) a nucleic acid encoding a RHOA dominant negative polypeptide or biologically active fragment thereof and 2) a RHOA dominant negative polypeptide or biologically active fragment thereof), or whose predicted likelihood of efficacy of the agent for treating a cancer that has a reduced level of CDH1 is determined, is a mammal (e.g., mouse, rat, primate, non-human mammal, domestic animal, such as a dog, cat, cow, horse, and the like), and is preferably a human. In another embodiment, the subject is an animal model of cancer. For example, the animal model can be an orthotopic xenograft animal model of a human-derived cancer.

In another embodiment of the methods of the present invention, the subject has not undergone treatment, such as chemotherapy, radiation therapy, targeted therapy, and/or immunotherapies. In still another embodiment, the subject has undergone treatment, such as chemotherapy, radiation therapy, targeted therapy, and/or immunotherapies.

In certain embodiments, the subject has had surgery to remove cancerous or precancerous tissue. In other embodiments, the cancerous tissue has not been removed, e.g., the cancerous tissue may be located in an inoperable region of the body, such as in a tissue that is essential for life, or in a region where a surgical procedure would cause considerable risk of harm to the patient.

V. Methods of Treatment

The present invention provides for both prophylactic and therapeutic methods of treating a subject at risk of (or susceptible to) a cancer that has a reduced level of CDH1. In some embodiments, the cancer has a loss of CDH1 expression, e.g., CDH1-null cancer. In some embodiments, the cancer is undergoing or has undergone epithelal to mesenchymal transition (EMT). In certain embodiments, the cancer is diffuse gastric cancer (DGC) or lobular breast cancer.

1. Prophylactic Methods

In one aspect, the present invention provides a method for preventing a subject afflicted with cancer that has a reduced level of CDH1, by administering to the subject a therapeutically effective amount of at least one agent selected from the group consisting of 1) a nucleic acid encoding a RHOA dominant negative polypeptide or biologically active fragment thereof and 2) a RHOA dominant negative polypeptide or biologically active fragment thereof. Administration of a prophylactic agent can occur prior to the manifestation of symptoms characteristic of cancer that has a reduced level of CDH1, such that a cancer is prevented or, alternatively, delayed in its progression.

2. Therapeutic Methods

Another aspect of the present invention pertains to methods treating a subject afflicted with cancer that has a reduced level of CDH1, by administering to the subject a therapeutically effective amount of at least one agent selected from the group consisting of 1) a nucleic acid encoding a RHOA dominant negative polypeptide or biologically active fragment thereof and 2) a RHOA dominant negative polypeptide or biologically active fragment thereof.

Modulatory methods of the present invention involve contacting a cancer cell that has a reduced level of CDH1 with at least one agent selected from the group consisting of 1) a nucleic acid encoding a RHOA dominant negative polypeptide or biologically active fragment thereof and 2) a RHOA dominant negative polypeptide or biologically active fragment thereof.

These modulatory methods can be performed in vitro (e.g., by contacting the cell with the agent) or, alternatively, by contacting an agent with cells in vivo (e.g., by administering the agent to a subject). In one embodiment, the method involves administering an agent (e.g., an agent described herein, or an agent identified by a screening assay described herein), or combination of agents that selected from the group consisting of 1) a nucleic acid encoding a RHOA dominant negative polypeptide or biologically active fragment thereof and 2) a RHOA dominant negative polypeptide or biologically active fragment thereof.

In addition, these modulatory agents can also be administered in combination therapy with, e.g., chemotherapeutic agents, hormones, antiangiogens, radiolabelled, compounds, or with surgery, cryotherapy, and/or radiotherapy. The preceding treatment methods can be administered in conjunction with other forms of conventional therapy (e.g., standard-of-care treatments for cancer well-known to the skilled artisan), either consecutively with, pre- or post-conventional therapy. For example, these modulatory agents can be administered with a therapeutically effective dose of chemotherapeutic agent. In another embodiment, these modulatory agents are administered in conjunction with chemotherapy to enhance the activity and efficacy of the chemotherapeutic agent. The Physicians' Desk Reference (PDR) discloses dosages of chemotherapeutic agents that have been used in the treatment of various cancers. The dosing regimen and dosages of these aforementioned chemotherapeutic drugs that are therapeutically effective will depend on the particular cancer being treated, the extent of the disease and other factors familiar to the physician of skill in the art, and can be determined by the physician.

The term "targeted therapy" refers to administration of agents that selectively interact with a chosen biomolecule to thereby treat cancer. For example, targeted therapy regarding the inhibition of immune checkpoint inhibitor is useful in combination with the methods of the present invention. The term "immune checkpoint inhibitor" means a group of molecules on the cell surface of CD4+ and/or CD8+ T cells that fine-tune immune responses by down-modulating or inhibiting an anti-tumor immune response. Immune checkpoint proteins are well-known in the art and include, without limitation, CTLA-4, PD-1, VISTA, B7-H2, B7-H3, PD-L1, B7-H4, B7-H6, 2B4, ICOS, HVEM, PD-L2, CD160, gp49B, PIR-B, KIR family receptors, TIM-1, TIM-3, TIM-4, LAG-3, BTLA, SIRPalpha (CD47), CD48, 2B4 (CD244), B7.1, B7.2, ILT-2, ILT-4, TIGIT, and A2aR (see, for example, WO 2012/177624). Inhibition of one or more immune checkpoint inhibitors can block or otherwise neutralize inhibitory signaling to thereby upregulate an immune response in order to more efficaciously treat cancer.

Immunotherapy is one form of targeted therapy that may comprise, for example, the use of cancer vaccines and/or sensitized antigen presenting cells. For example, an oncolytic virus is a virus that is able to infect and lyse cancer cells, while leaving normal cells unharmed, making them potentially useful in cancer therapy. Replication of oncolytic viruses both facilitates tumor cell destruction and also produces dose amplification at the tumor site. They may also act as vectors for anticancer genes, allowing them to be specifically delivered to the tumor site. The immunotherapy can involve passive immunity for short-term protection of a host, achieved by the administration of pre-formed antibody directed against a cancer antigen or disease antigen (e.g., administration of a monoclonal antibody, optionally linked to a chemotherapeutic agent or toxin, to a tumor antigen). For example, anti-VEGF and mTOR inhibitors are known to be effective in treating renal cell carcinoma. Immunotherapy can also focus on using the cytotoxic lymphocyte-recognized epitopes of cancer cell lines. Alternatively, antisense polynucleotides, ribozymes, RNA interference molecules, triple helix polynucleotides and the like, can be used to selectively modulate biomolecules that are linked to the initiation, progression, and/or pathology of a tumor or cancer.

The term "untargeted therapy" referes to administration of agents that do not selectively interact with a chosen biomolecule yet treat cancer. Representative examples of untargeted therapies include, without limitation, chemotherapy, gene therapy, and radiation therapy.

In one embodiment, chemotherapy is used. Chemotherapy includes the administration of a chemotherapeutic agent. Such a chemotherapeutic agent may be, but is not limited to, those selected from among the following groups of compounds: platinum compounds, cytotoxic antibiotics, antimetabolities, anti-mitotic agents, alkylating agents, arsenic compounds, DNA topoisomerase inhibitors, taxanes, nucleoside analogues, plant alkaloids, and toxins; and synthetic derivatives thereof. Exemplary compounds include, but are not limited to, alkylating agents: cisplatin, treosulfan, and trofosfamide; plant alkaloids: vinblastine, paclitaxel, docetaxol; DNA topoisomerase inhibitors: teniposide, crisnatol, and mitomycin; anti-folates: methotrexate, mycophenolic acid, and hydroxyurea; pyrimidine analogs: 5-fluorouracil, doxifluridine, and cytosine arabinoside; purine analogs: mercaptopurine and thioguanine; DNA antimetabolites: 2'-deoxy-5-fluorouridine, aphidicolin glycinate, and pyrazoloimidazole; and antimitotic agents: halichondrin, colchicine, and rhizoxin. Compositions comprising one or more chemotherapeutic agents (e.g., FLAG, CHOP) may also be used. FLAG comprises fludarabine, cytosine arabinoside (Ara-C) and G-CSF. CHOP comprises cyclophosphamide, vincristine, doxorubicin, and prednisone. In another embodiment, PARP (e.g., PARP-1 and/or PARP-2) inhibitors are used and such inhibitors are well-known in the art (e.g., Olaparib, ABT-888, BSI-201, BGP-15 (N-Gene Research Laboratories, Inc.); INO-1001 (Inotek Pharmaceuticals Inc.); PJ34 (Soriano et al. (2001) *Circ. Res.* 89(8): 684-91; Pacher et al. (2002) *Br. J. Pharmacol.* 135(6): 1347-1350); 3-aminobenzamide (Trevigen); 4-amino-1,8-naphthalimide; (Trevigen); 6(5H)-phenanthridinone (Trevigen); benzamide (U.S. Pat. Re. 36,397); and NU1025 (Bowman et al. (2001) *Br. J. Cancer* 84(1):106-12). The mechanism of action is generally related to the ability of PARP inhibitors to bind PARP and decrease its activity. PARP catalyzes the conversion of .beta.-nicotinamide adenine dinucleotide (NAD+) into nicotinamide and poly-ADP-ribose (PAR). Both poly (ADP-ribose) and PARP have been linked to regulation of transcription, cell proliferation, genomic stability, and carcinogenesis (Bouchard V. J. et.al. Experimental Hematology, Volume 31, Number 6, June 2003, pp. 446-454(9); Herceg Z.; Wang Z.-Q. Mutation Research/Fundamental and Molecular Mechanisms of Mutagenesis, Volume 477, Number 1, 2 Jun. 2001, pp. 97-110(14)). Poly(ADP-ribose) polymerase 1 (PARP1) is a key molecule in the repair of DNA single-strand breaks (SSBs) (de Murcia et al. (1997) *Proc Natl Acad Sci USA* 94:7303-7307; Schreiber et al. (2006) *Nat Rev Mol Cell Biol* 7:517-528; Wang et al. (1997) *Genes Dev* 11:2347-2358). Knockout of SSB repair by inhibition of PARP1 function induces DNA double-strand breaks (DSBs) that can trigger synthetic lethality in cancer cells with defective homology-directed DSB repair (Bryant et al. (2005) *Nature* 434:913-917; Farmer et al. (2005) *Nature* 434:917-921). The foregoing examples of chemotherapeutic agents are illustrative, and are not intended to be limiting.

In another embodiment, radiation therapy is used. The radiation used in radiation therapy can be ionizing radiation. Radiation therapy can also be gamma rays, X-rays, or proton beams. Examples of radiation therapy include, but are not limited to, external-beam radiation therapy, interstitial implantation of radioisotopes (1-125, palladium, iridium), radioisotopes such as strontium-89, thoracic radiation therapy, intraperitoneal P-32 radiation therapy, and/or total abdominal and pelvic radiation therapy. For a general overview of radiation therapy, see Hellman, Chapter 16: Principles of Cancer Management: Radiation Therapy, 6th edition, 2001, DeVita et al., eds., J. B. Lippencott Company, Philadelphia. The radiation therapy can be administered as external beam radiation or teletherapy wherein the radiation is directed from a remote source. The radiation treatment can also be administered as internal therapy or brachytherapy wherein a radioactive source is placed inside the body close to cancer cells or a tumor mass. Also encompassed is the use of photodynamic therapy comprising the administration of photosensitizers, such as hematoporphyrin and its derivatives, Vertoporfin (BPD-MA), phthalocyanine, photosensitizer Pc4, demethoxy-hypocrellin A; and 2BA-2-DMHA.

In another embodiment, hormone therapy is used. Hormonal therapeutic treatments can comprise, for example, hormonal agonists, hormonal antagonists (e.g., flutamide, bicalutamide, tamoxifen, raloxifene, leuprolide acetate (LUPRON), LH-RH antagonists), inhibitors of hormone biosynthesis and processing, and steroids (e.g., dexamethasone, retinoids, deltoids, betamethasone, cortisol, cortisone, prednisone, dehydrotestosterone, glucocorticoids, mineralocorticoids, estrogen, testosterone, progestins), vitamin A derivatives (e.g., all-trans retinoic acid (ATRA)); vitamin D3 analogs; antigestagens (e.g., mifepristone, onapristone), or antiandrogens (e.g., cyproterone acetate).

In another embodiment, hyperthermia, a procedure in which body tissue is exposed to high temperatures (up to 106° F.) is used. Heat may help shrink tumors by damaging cells or depriving them of substances they need to live. Hyperthermia therapy can be local, regional, and whole-body hyperthermia, using external and internal heating devices. Hyperthermia is almost always used with other forms of therapy (e.g., radiation therapy, chemotherapy, and biological therapy) to try to increase their effectiveness. Local hyperthermia refers to heat that is applied to a very small area, such as a tumor. The area may be heated externally with high-frequency waves aimed at a tumor from a device outside the body. To achieve internal heating, one of several types of sterile probes may be used, including thin, heated wires or hollow tubes filled with warm water; implanted microwave antennae; and radiofrequency electrodes. In regional hyperthermia, an organ or a limb is heated. Magnets and devices that produce high energy are placed over the region to be heated. In another approach, called perfusion, some of the patient's blood is removed, heated, and then pumped (perfused) into the region that is to be heated internally. Whole-body heating is used to treat metastatic cancer that has spread throughout the body. It can be accomplished using warm-water blankets, hot wax, inductive coils (like those in electric blankets), or thermal chambers (similar to large incubators). Hyperthermia does not cause any marked increase in radiation side effects or complications. Heat applied directly to the skin, however, can cause discomfort or even significant local pain in about half the patients treated. It can also cause blisters, which generally heal rapidly.

In still another embodiment, photodynamic therapy (also called PDT, photoradiation therapy, phototherapy, or photochemotherapy) is used for the treatment of some types of cancer. It is based on the discovery that certain chemicals known as photosensitizing agents can kill one-celled organisms when the organisms are exposed to a particular type of light. PDT destroys cancer cells through the use of a fixed-frequency laser light in combination with a photosensitizing agent. In PDT, the photosensitizing agent is injected into the bloodstream and absorbed by cells all over the body. The agent remains in cancer cells for a longer time than it does in normal cells. When the treated cancer cells are exposed to laser light, the photosensitizing agent absorbs the light and produces an active form of oxygen that destroys the treated cancer cells. Light exposure must be timed carefully so that it occurs when most of the photosensitizing agent has left healthy cells but is still present in the cancer cells. The laser light used in PDT can be directed through a fiber-optic (a very thin glass strand). The fiber-optic is placed close to the cancer to deliver the proper amount of light. The fiber-optic can be directed through a bronchoscope into the lungs for the treatment of lung cancer or through an endoscope into the esophagus for the treatment of esophageal cancer. An advantage of PDT is that it causes minimal damage to healthy tissue. However, because the laser light currently in use cannot pass through more than about 3 centimeters of tissue (a little more than one and an eighth inch), PDT is mainly used to treat tumors on or just under the skin or on the lining of internal organs. Photodynamic therapy makes the skin and eyes sensitive to light for 6 weeks or more after treatment. Patients are advised to avoid direct sunlight and bright indoor light for at least 6 weeks. If patients must go outdoors, they need to wear protective clothing, including sunglasses. Other temporary side effects of PDT are related to the treatment of specific areas and can include coughing, trouble swallowing, abdominal pain, and painful breathing or shortness of breath. In December 1995, the U.S. Food and Drug Administration (FDA) approved a photosensitizing agent called porfimer sodium, or Photofrin®, to relieve symptoms of esophageal cancer that is causing an obstruction and for esophageal cancer that cannot be satisfactorily treated with lasers alone. In January 1998, the FDA approved porfimer sodium for the treatment of early nonsmall cell lung cancer in patients for whom the usual treatments for lung cancer are not appropriate. The National Cancer Institute and other institutions are supporting clinical trials (research studies) to evaluate the use of photodynamic therapy for several types of cancer, including cancers of the bladder, brain, larynx, and oral cavity.

In yet another embodiment, laser therapy is used to harness high-intensity light to destroy cancer cells. This technique is often used to relieve symptoms of cancer such as bleeding or obstruction, especially when the cancer cannot be cured by other treatments. It may also be used to treat cancer by shrinking or destroying tumors. The term "laser" stands for light amplification by stimulated emission of radiation. Ordinary light, such as that from a light bulb, has many wavelengths and spreads in all directions. Laser light, on the other hand, has a specific wavelength and is focused in a narrow beam. This type of high-intensity light contains a lot of energy. Lasers are very powerful and may be used to cut through steel or to shape diamonds. Lasers also can be used for very precise surgical work, such as repairing a damaged retina in the eye or cutting through tissue (in place of a scalpel). Although there are several different kinds of lasers, only three kinds have gained wide use in medicine: Carbon dioxide ($CO_2$) laser—This type of laser can remove thin layers from the skin's surface without penetrating the deeper layers. This technique is particularly useful in treating tumors that have not spread deep into the skin and certain precancerous conditions. As an alternative to traditional scalpel surgery, the $CO_2$ laser is also able to cut the skin. The laser is used in this way to remove skin cancers. Neodymium:yttrium-aluminum-garnet (Nd:YAG) laser—Light from this laser can penetrate deeper into tissue than light from the other types of lasers, and it can cause blood to clot quickly. It can be carried through optical fibers to less accessible parts of the body. This type of laser is sometimes used to treat throat cancers. Argon laser—This laser can pass through only superficial layers of tissue and is therefore useful in dermatology and in eye surgery. It also is used with light-sensitive dyes to treat tumors in a procedure known as photodynamic therapy (PDT). Lasers have several advantages over standard surgical tools, including: Lasers are more precise than scalpels. Tissue near an incision is protected, since there is little contact with surrounding skin or other tissue. The heat produced by lasers sterilizes the surgery site, thus reducing the risk of infection. Less operating time may be needed because the precision of the laser allows for a smaller incision. Healing time is often shortened; since laser heat seals blood vessels, there is less bleeding, swelling, or scarring. Laser surgery may be less complicated. For example, with fiber optics, laser light can be directed to parts of the body without making a large incision. More procedures may be done on an outpatient basis. Lasers can be used in two ways to treat cancer: by shrinking or destroying a tumor with heat, or by activating a chemical—known as a photosensitizing agent—that destroys cancer cells. In PDT, a photosensitizing agent is retained in cancer cells and can be stimulated by light to cause a reaction that kills cancer cells. $CO_2$ and Nd:YAG lasers are used to shrink or destroy tumors. They may be used with endoscopes, tubes that allow physicians to see into certain areas of the body, such as the bladder. The light from some lasers can be transmitted through a flexible endoscope fitted with fiber optics. This allows physicians to see and work in parts of the body that could not otherwise be reached except by surgery and therefore allows very precise aiming of the laser beam. Lasers also may be used with low-power microscopes, giving the doctor a clear view of the site being treated. Used with other instruments, laser systems can produce a cutting area as small as 200 microns in diameter—less than the width of a very fine thread. Lasers are used to treat many types of cancer. Laser surgery is a standard treatment for certain stages of glottis (vocal cord), cervical, skin, lung, vaginal, vulvar, and penile cancers. In addition to its use to destroy the cancer, laser surgery is also used to help relieve symptoms caused by cancer (palliative care). For example, lasers may be used to shrink or destroy a tumor that is blocking a patient's trachea (windpipe), making it easier to breathe. It is also sometimes used for palliation in colorectal and anal cancer. Laser-induced interstitial thermotherapy (LITT) is one of the most recent developments in laser therapy. LITT uses the same idea as a cancer treatment called hyperthermia; that heat may help shrink tumors by damaging cells or depriving them of substances they need to live. In this treatment, lasers are directed to interstitial areas (areas between organs) in the body. The laser light then raises the temperature of the tumor, which damages or destroys cancer cells.

The duration and/or dose of treatment with the modulatory agents described herein may vary according to the particular modulator or combination thereof. An appropriate treatment time for a particular cancer therapeutic agent will be appreciated by the skilled artisan. The invention contemplates the continued assessment of optimal treatment schedules for each cancer therapeutic agent, where the phenotype of the cancer of the subject as determined by the methods of the invention is a factor in determining optimal treatment doses and schedules.

VI. Clinical Efficacy

Clinical efficacy can be measured by any method known in the art. For example, the response to an cancer therapy (e.g., at least one agent selected from the group consisting of 1) a nucleic acid encoding a RHOA dominant negative polypeptide or biologically active fragment thereof and 2) a RHOA dominant negative polypeptide or biologically active fragment thereof), relates to any response of the cancer, e.g., a tumor, to the therapy, preferably to a change in tumor mass and/or volume after initiation of neoadjuvant or adjuvant chemotherapy. Tumor response may be assessed in a neoadjuvant or adjuvant situation where the size of a tumor after systemic intervention can be compared to the initial size and dimensions as measured by CT, PET, mammogram, ultrasound or palpation and the cellularity of a tumor can be estimated histologically and compared to the cellularity of a tumor biopsy taken before initiation of treatment. Response may also be assessed by caliper measurement or pathological examination of the tumor after biopsy or surgical resection. Response may be recorded in a quantitative fashion like percentage change in tumor volume or cellularity or using a semi-quantitative scoring system such as residual cancer burden (Symmans et al. (2007) *J. Clin. Oncol.* 25:4414-4422) or Miller-Payne score (Ogston et al. (2003) *Breast* (Edinburgh, Scotland) 12:320-327) in a qualitative fashion like "pathological complete response" (pCR), "clinical complete remission" (cCR), "clinical partial remission" (cPR), "clinical stable disease" (cSD), "clinical progressive disease" (cPD) or other qualitative criteria. Assessment of tumor response may be performed early after the onset of neoadjuvant or adjuvant therapy, e.g., after a few hours, days, weeks or preferably after a few months. A typical endpoint for response assessment is upon termination of neoadjuvant chemotherapy or upon surgical removal of residual tumor cells and/or the tumor bed.

In some embodiments, clinical efficacy of the therapeutic treatments described herein may be determined by measuring the clinical benefit rate (CBR). The clinical benefit rate is measured by determining the sum of the percentage of patients who are in complete remission (CR), the number of patients who are in partial remission (PR) and the number of patients having stable disease (SD) at a time point at least 6 months out from the end of therapy. The shorthand for this formula is CBR=CR+PR+SD over 6 months. In some embodiments, the CBR for a particular modulator of biomarkers listed in Table 1, 2, and/or 3 therapeutic regimen is at least 25%, 30%, 35%, 40%, 45%, 50%, 55%, 60%, 65%, 70%, 75%, 80%, 85%, or more.

Additional criteria for evaluating the response to cancer therapy (e.g., at least one agent selected from the group consisting of 1) a nucleic acid encoding a RHOA dominant negative polypeptide or biologically active fragment thereof and 2) a RHOA dominant negative polypeptide or biologically active fragment thereof) are related to "survival," which includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g., time of diagnosis or start of treatment) and end point (e.g., death, recurrence or metastasis). In addition, criteria for efficacy of treatment can be expanded to include response to chemotherapy, probability of survival, probability of metastasis within a given time period, and probability of tumor recurrence.

For example, in order to determine appropriate threshold values, a particular agent encompassed by the present invention can be administered to a population of subjects and the outcome can be correlated to biomarker measurements that were determined prior to administration of any cancer therapy (e.g., at least one agent selected from the group consisting of 1) a nucleic acid encoding a RHOA dominant negative polypeptide or biologically active fragment thereof and 2) a RHOA dominant negative polypeptide or biologically active fragment thereof). The outcome measurement may be pathologic response to therapy given in the neoadjuvant setting. Alternatively, outcome measures, such as overall survival and disease-free survival can be monitored over a period of time for subjects following cancer therapy (e.g., at least one agent selected from the group consisting of 1) a nucleic acid encoding a RHOA dominant negative polypeptide or biologically active fragment thereof and 2) a RHOA dominant negative polypeptide or biologically active fragment thereof) for whom biomarker measurement values are known. In certain embodiments, the same doses of the agent are administered to each subject. In related embodiments, the doses administered are standard doses known in the art for the agent. The period of time for which subjects are monitored can vary. For example, subjects may be monitored for at least 2, 4, 6, 8, 10, 12, 14, 16, 18, 20, 25, 30, 35, 40, 45, 50, 55, or 60 months. Biomarker measurement threshold values that correlate to outcome of a cancer therapy (e.g., at least one agent selected from the group consisting of 1) a nucleic acid encoding a RHOA dominant negative polypeptide or biologically active fragment thereof and 2) a RHOA dominant negative polypeptide or biologically active fragment thereof) can be determined using methods such as those described in the Examples section.

VII. Pharmaceutical Compositions

In another aspect, the present invention provides pharmaceutically acceptable compositions which comprise a therapeutically-effective amount of at least one agent selected from the group consisting of 1) a nucleic acid encoding a RHOA dominant negative polypeptide or biologically active fragment thereof and 2) a RHOA dominant negative polypeptide or biologically active fragment thereof, formulated together with one or more pharmaceutically acceptable carriers (additives) and/or diluents and/or additional active ingredients. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound.

The phrase "therapeutically-effective amount" as used herein means that amount of an agent selected from the group consisting of 1) a nucleic acid encoding a RHOA dominant negative polypeptide or biologically active fragment thereof and 2) a RHOA dominant negative polypeptide or biologically active fragment thereof, or composition comprising an agent selected from the group consisting of 1) a nucleic acid encoding a RHOA dominant negative polypeptide or biologically active fragment thereof and 2) a RHOA dominant negative polypeptide or biologically active fragment thereof, which is effective for producing some desired therapeutic effect, e.g., reduces the number of viable or proliferating cells in the cancer, and/or reduces the volume or size of a tumor comprising the cancer cells, at a reasonable benefit/risk ratio.

The phrase "pharmaceutically acceptable" is employed herein to refer to those agents, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier must be "acceptable" in the sense of being compatible with the other ingredients of the formulation and not injurious to the subject. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "pharmaceutically-acceptable salts" refers to the relatively non-toxic, inorganic and organic acid addition salts of the agents encompassed by the present invention. These salts can be prepared in situ during the final isolation and purification of the therapeutic agents, or by separately reacting a purified therapeutic agent in its free base form with a suitable organic or inorganic acid, and isolating the salt thus formed.

Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like (See, for example, Berge et al. (1977) *J. Pharm. Sci.* 66:1-19).

In other cases, the agents useful in the methods of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of the agents encompassed by the present invention. These salts can likewise be prepared in situ during the final isolation and purification of the therapeutic agents, or by separately reacting the purified therapeutic agent in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like (see, for example, Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations useful in the methods of the present invention include those suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient, which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an agent encompassed by the present invention, with the carrier and, optionally, one or more accessory ingredients. In general, the formulations are prepared by uniformly and intimately bringing into association a therapeutic agent with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a therapeutic agent as an active ingredient. A compound may also be administered as a bolus, electuary or paste.

In solid dosage forms for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered peptide or peptidomimetic moistened with an inert liquid diluent.

Tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions, which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions, which can be used include polymeric substances and waxes. The active ingredient can also be in micro-encapsulated form, if appropriate, with one or more of the above-described excipients.

Liquid dosage forms for oral administration include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active agent may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more therapeutic agents with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Formulations which are suitable for vaginal administration also include pessaries, tampons, creams, gels, pastes, foams or spray formulations containing such carriers as are known in the art to be appropriate.

Dosage forms for the topical or transdermal administration of an agent encompassed by the present invention include powders, sprays, ointments, pastes, creams, lotions, gels, solutions, patches and inhalants. The active component may be mixed under sterile conditions with a pharmaceutically-acceptable carrier, and with any preservatives, buffers, or propellants which may be required.

The ointments, pastes, creams and gels may contain, in addition to a therapeutic agent, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the agent encompassed by the present invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The agent encompassed by the present invention, can be alternatively administered by aerosol. This is accomplished by preparing an aqueous aerosol, liposomal preparation or solid particles containing the compound. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, and amino acids such as glycine, buffers, salts, sugars or sugar alcohols. Aerosols generally are prepared from isotonic solutions.

Transdermal patches have the added advantage of providing controlled delivery of a therapeutic agent to the body. Such dosage forms can be made by dissolving or dispersing the agent in the proper medium. Absorption enhancers can also be used to increase the flux of the peptidomimetic across the skin. The rate of such flux can be controlled by either providing a rate controlling membrane or dispersing the peptidomimetic in a polymer matrix or gel.

Ophthalmic formulations, eye ointments, powders, solutions and the like, are also contemplated as being within the scope of this invention.

Pharmaceutical compositions of this invention suitable for parenteral administration comprise one or more therapeutic agents in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of an agent encompassed by the present invention, in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions, which are compatible with body tissue.

When the therapeutic agents of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

Actual dosage levels of the active ingredients in the pharmaceutical compositions of this invention may be determined by the methods of the present invention so as to obtain an amount of the active ingredient, which is effective to achieve the desired therapeutic response for a particular subject, composition, and mode of administration, without being toxic to the subject.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. U.S.A.* 91:3054 3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

VIII. Administration of Agents

The term "administering" is intended to include routes of administration which allow the agent to perform its intended function. Examples of routes of administration which can be used include injection (subcutaneous, intravenous, parenterally, intraperitoneally, intrathecal), oral, inhalation, and transdermal. The injection can be bolus injections or can be continuous infusion. Depending on the route of administration, the agent can be coated with or disposed in a selected material to protect it from natural conditions which may detrimentally affect its ability to perform its intended function. The agent may be administered alone, or in conjunction with a pharmaceutically acceptable carrier. The agent also may be administered as a prodrug, which is converted to its active form in vivo. The agent may also be administered in combination with one or more additional therapeutic agent(s) (e.g., before, after or simultaneously therewith).

It will be appreciated that individual dosages may be varied depending upon the requirements of the subject in the judgment of the attending clinician, the severity of the condition being treated and the particular compound being employed. In determining the therapeutically effective amount or dose, a number of additional factors may be considered by the attending clinician, including, but not limited to, the pharmacodynamic characteristics of the particular therapeutic agent and its mode and route of administration; the desired time course of treatment; the species of mammal; its size, age, and general health; the specific disease involved; the degree of or involvement or the severity of the disease; the response of the individual subject; the particular compound administered; the mode of administration; the bioavailability characteristics of the preparation administered; the dose regimen selected; the kind of concurrent treatment; and other relevant circumstances.

Treatment can be initiated with smaller dosages which are less than the effective dose of the compound. Thereafter, in one embodiment, the dosage should be increased by small increments until the optimum effect under the circumstances is reached. For convenience, the total daily dosage may be divided and administered in portions during the day if desired.

In general, it is preferable to obtain a first sample from the subject prior to beginning therapy and one or more samples during treatment. In such a use, a baseline of expression of cells from subjects with the disorder prior to therapy is determined and then changes in the baseline state of expression of cells from subjects with the disorder is monitored during the course of therapy. Alternatively, two or more successive samples obtained during treatment can be used without the need of a pre-treatment baseline sample. In such a use, the first sample obtained from the subject is used as a baseline for determining whether the expression of cells from subjects with the disorder is increasing or decreasing.

Any means for the introduction of a polynucleotide into mammals, human or non-human, or cells thereof may be adapted to the practice of this invention for the delivery of the various constructs of the invention into the intended recipient. In one embodiment of the invention, the DNA constructs are delivered to cells by transfection, i.e., by delivery of "naked" DNA or in a complex with a colloidal dispersion system. A colloidal system includes macromolecule complexes, nanocapsules, microspheres, beads, and lipid-based systems including oil-in-water emulsions, micelles, mixed micelles, and liposomes. The preferred colloidal system of this invention is a lipid-complexed or liposome-formulated DNA. In the former approach, prior to formulation of DNA, e.g., with lipid, a plasmid containing a transgene bearing the desired DNA constructs may first be experimentally optimized for expression (e.g., inclusion of an intron in the 5' untranslated region and elimination of unnecessary sequences (Felgner, et al., (1995) *Ann NY Acad Sci* 126-139). Formulation of DNA, e.g. with various lipid or liposome materials, may then be effected using known methods and materials and delivered to the recipient mammal. See, e.g., Canonico et al (1994) *Am J Respir Cell Mol Biol* 10:24-29; Tsan et al. (1995) *Am J Physiol* 268:L1052-1056; Alton et al. (1993) *Nat Genet.* 5:135-142, and U.S. Pat. No. 5,679,647.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs, which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand. Naked DNA or DNA associated with a delivery vehicle, e.g., liposomes, can be administered to several sites in a subject (see below). Nucleic acids can be delivered in any desired vector. These include viral or non-viral vectors, including adenovirus vectors, adeno-associated virus vectors, retrovirus vectors, lentivirus vectors, and plasmid vectors. Exemplary types of viruses include HSV (herpes simplex virus), AAV (adeno associated virus), HIV (human immunodeficiency virus), BIV (bovine immunodeficiency virus), and MLV (murine leukemia virus). Nucleic acids can be administered in any desired format that provides sufficiently efficient delivery levels, including in virus particles, in liposomes, in nanoparticles, and complexed to polymers.

The nucleic acids encoding a protein or nucleic acid of interest may be in a plasmid or viral vector, or other vector as is known in the art. Such vectors are well known and any can be selected for a particular application. In one embodiment of the invention, the gene delivery vehicle comprises a promoter and a demethylase coding sequence. Preferred promoters are tissue-specific promoters and promoters which are activated by cellular proliferation, such as the thymidine kinase and thymidylate synthase promoters. Other preferred promoters include promoters which are activatable by infection with a virus, such as the α- and β-interferon promoters, and promoters which are activatable by a hormone, such as estrogen. Other promoters which can be used include the Moloney virus LTR, the CMV promoter, and the mouse albumin promoter. A promoter may be constitutive or inducible.

In another embodiment, naked polynucleotide molecules are used as gene delivery vehicles, as described in WO 90/11092 and U.S. Pat. No. 5,580,859. Such gene delivery vehicles can be either growth factor DNA or RNA and, in certain embodiments, are linked to killed adenovirus (Curiel et al. (1992) *Hum. Gene. Ther.* 3:147-154). Other vehicles which can optionally be used include DNA-ligand (Wu et al. (1989) *J. Biol. Chem.* 264:16985-16987), lipid-DNA combinations (Feigner et al. (1989) *Proc. Natl. Acad. Sci. USA* 84:7413-7417), liposomes (Wang et al. (1987) *Proc. Natl. Acad. Sci.* 84:7851-7855) and microprojectiles (Williams et al. (1991) *Proc. Natl. Acad. Sci.* 88:2726-2730).

A gene delivery vehicle can optionally comprise viral sequences such as a viral origin of replication or packaging signal. These viral sequences can be selected from viruses such as astrovirus, coronavirus, orthomyxovirus, papovavirus, paramyxovirus, parvovirus, picornavirus, poxvirus, retrovirus, togavirus or adenovirus. In a preferred embodiment, the growth factor gene delivery vehicle is a recombinant retroviral vector. Recombinant retroviruses and various uses thereof have been described in numerous references including, for example, Mann et al. (1983) *Cell* 33:153, Cane and Mulligan (1984) *Proc. Nat'l. Acad. Sci. USA* 81:6349, Miller et al. (1990) *Human Gene Therapy* 1:5-14, U.S. Pat. Nos. 4,405,712, 4,861,719, and 4,980,289, and PCT Application Nos. WO 89/02,468, WO 89/05,349, and WO 90/02,806. Numerous retroviral gene delivery vehicles can be utilized in the present invention, including for example those described in EP 0,415,731; WO 90/07936; WO 94/03622; WO 93/25698; WO 93/25234; U.S. Pat. No. 5,219,740; WO 9311230; WO 9310218; Vile and Hart (1993) *Cancer Res.* 53:3860-3864; Vile and Hart (1993) *Cancer Res.* 53:962-967; Ram et al. (1993) *Cancer Res.* 53:83-88; Takamiya et al. (1992) *J. Neurosci. Res.* 33:493-503; Baba et al. (1993) *J. Neurosurg.* 79:729-735 (U.S. Pat. No. 4,777,127, GB 2,200,651, EP 0,345,242 and WO91/02805).

Other viral vector systems that can be used to deliver a polynucleotide of the invention have been derived from herpes virus, e.g., Herpes Simplex Virus (U.S. Pat. No. 5,631,236 by Woo et al., issued May 20, 1997 and WO 00/08191 by Neurovex), vaccinia virus (Ridgeway (1988) "Mammalian expression vectors," In: Rodriguez R L, Denhardt D T, ed. Vectors: A survey of molecular cloning vectors and their uses. Stoneham: Butterworth; Baichwal and Sugden (1986) "Vectors for gene transfer derived from animal DNA viruses: Transient and stable expression of transferred genes," In: Kucherlapati R, ed. Gene transfer. New York: Plenum Press; Coupar et al. (1988) Gene, 68:1-10), and several RNA viruses. Preferred viruses include an alphavirus, a poxivirus, an arena virus, a vaccinia virus, a polio virus, and the like. They offer several attractive features for various mammalian cells (Friedmann (1989) *Science* 244: 1275-1281; Ridgeway, 1988, supra; Baichwal and Sugden, 1986, supra; Coupar et al., 1988, supra; Horwich et al. (1990) *J. Virol.* 64:642-650).

In other embodiments, target DNA in the genome can be manipulated using well-known methods in the art. For example, the target DNA in the genome can be manipulated by deletion, insertion, and/or mutation are retroviral insertion, artificial chromosome techniques, gene insertion, random insertion with tissue specific promoters, gene targeting, transposable elements and/or any other method for introducing foreign DNA or producing modified DNA/modified nuclear DNA. Other modification techniques include deleting DNA sequences from a genome and/or altering nuclear DNA sequences. Nuclear DNA sequences, for example, may be altered by site-directed mutagenesis.

In other embodiments, recombinant RHOA dominant negative polypeptides, and fragments thereof, can be administered to subjects. In some embodiments, fusion proteins can be constructed and administered which have enhanced biological properties (e.g., Fc fusion proteins discussed above). In addition, the RHOA dominant negative polypeptides, and fragment thereof, can be modified according to well-known pharmacological methods in the art (e.g., pegylation, glycosylation, oligomerization, etc.) in order to further enhance desirable biological activities, such as increased bioavailability and decreased proteolytic degradation.

EXEMPLIFICATION

This invention is further illustrated by the following examples, which should not be construed as limiting.

Example 1: Materials and Methods for Example 2 a. Mouse Colonies

Mist1-CreERT2, Cdh1flox/flox, Tomation/GFP mice, which carry conditional alleles with loxP sites flanking exon 2-3 of Cdh1, were kindly provided by Timothy C. Wang at Columbia University. Cre recombinase was activated by oral administration of tamoxifen (Sigma, T5648) TAM (1-5 mg/0.2 ml corn oil, as indicated). All animal studies and procedures were approved by the ethics committees at Dana-Farber Cancer Institute.

b. Isolation and Culture of Mouse Stomach Organoids

The protocol as previously described in Miyoshi et al. (2013) *Nat. Prot.* 8:2471-2482 was performed as follows: Euthanize mice using a chemical reagent, open the stomach longitudinally and roughly remove contents on the paper towel. Rinse the tissue with ice cold PBS in a 90 mm petri dish, then wash the tissue with ~20 ml ice cold PBS in a 50 ml centrifuge tube by vigorous shaking. After washing, place the tissue in a 35 mm petri dish and bring the dish to a biological hood and mince the tissue with fine scissors. Add 1 ml collagenase solution (Invitrogen, 17100-0017, 2 mg/ml) using a 1,000 μl pipette and suspend tissue fragments in solution and incubate the petri dish in a cell culture incubator and pipette tissue mixture vigorously every 5-10 minutes using a 1,000 μl pipette. After pipetting, check if single epithelial units (crypts/pits) have been separated from the larger tissue fragments using a phase or dissection microscope. Set a 70 μm cell strainer in a 50 ml centrifuge tube, and filtrate tissue mixture through the cell strainer using a 1,000 μl pipette. Wash the strainer with 9 ml washing media and transfer filtrated cell suspension to a 15 ml centrifuge tube then centrifuge the tube at 20×g for 5 minutes. Add 500 μl-1 ml washing media and resuspend the cells in the tube. Transfer appropriate volume of suspension to a 1.5 ml tube (1,000-3,000 intact epithelial units per tube) and centrifuge the tube at 200×g for 5 minutes. Place the tube on ice and resuspend epithelial units in Matrigel (BD, 356234, 15 μl per tube). Place the tube and a 24-well plate on ice and add 15 μl of cell-Matrigel suspension to the center of each well using a 20 μl pipette and spread it carefully with a pipette tip. Incubate the plates in a cell culture incubator to polymerize the Matrigel. Turn the plates upside down to avoid the attachment of epithelial units to the surface of the plates. Add 500 μl 50% conditioned media to each well. For the small intestine and cecum, add 500 μl 50% conditioned media (add recombinant Wnt3a ((R&D Systems, 5036-WN-010) (100 ng/ml) and R-spondin 1 ((R&D Systems, 347-t-RS-050) (500 ng/ml) to advanced DMEM/F-12((invitrogen, 12634-010) containing 10 μM Y27632(R&D Systems, 1254) and 10 μM SB431542 (R&D Systems, 1614). Change media at least every 2 days.

c. *Lenti*-Virus Infection of Organoids

The following protocol was used: Grow organoids in a 24-well for 2-3 days and scratch and suspend Matrigel in culture media with a p1000 pipette. Transfer organoids suspension into a 15 ml tube and combine suspension from multiple wells depending on the assay scale. Centrifuge the tube at 200×g for 5 minutes and aspirate supernatant with around 100 µl left over. Resuspend organoids in 200 µl trypsin-EDTA and incubate the tube in 37° C. for 5 minutes. Add 1 ml washing media and dissociate organoids by vigorous pipetting. Centrifuge the tube at 200 g for 5 minutes and then resuspend cells in 25011.1 lentiviral solution (concentrated by LentiX™ Concentrator (Clontech, Cat. #631231), with 8 µg/ml polybrene (Sigma, TR-1003), 10 µM Y27632). Transfer the suspension into a well on a 48 well plate. Seal the plate with parafilm and perform spin-colation by centrifuging the plate at 600×g 32° C. for 1 hour. Incubate the plate at 37° C. for 6 hours to allow transduction. Add 1 ml conditioned medium to the well, resuspend and transfer the suspension to a 1.5 ml tube. Centrifuge the tube at 200×g 5 minutes and resuspend the cells in 15 µl matrigel and follow the procedures of culturing organoids and select with appropriate antibiotics.

d. Cell Viability Assay

Cell viability assay was performed by following the protocol of CellTiter-Glo® (Promega, Cat #G7570).

e. Xenograft Tumor Growth

The 4-week-old male nude mice (BALB/cA-nu (nu/nu)) were injected subcutaneously at each flank with cells infected with dox inducible control or RHOA mutant virus. All animals were maintained and used in accordance with the guidelines of the Institutional Animal Care and Use Committee of Dana-Farber Cancer Institute.

Example 2: RHOA Dominant Negative Mutants Kill CDH1-Null Cancer Cells

Diffuse Gastric Cancer (DGC) is a highly lethal variant of gastric cancer, which is prone to early invasion and metastasis, and lacks effective molecularly targeted therapies. DGC initiation typically follows loss of tumor suppressor CDH1 which encodes the cellular adhesion protein E-cadherin. Reduction in and/or loss of E-cadherin (CDH1) is the key hallmark of invasive lobular breast cancer and loss-of-function mutations targeting CDH1 are present in 50%-60% of invasive lobular breast cancer and are believed to be an early event often observed in matching lobular carcinoma in situ (McCart Reed et al. (2015) *Breast Cancer Res.* 17:12). It is demonstrated herein that ectopic expression of the small GTPase RHOA dominant negative forms, such as T19N, G17V, G17E, and the like, led to significant inhibition of proliferation and induction of cell-death in CDH1-null cells, but not in cells with intact CDH1. These results were confirmed by using isogenic stomach organoids model (with or without E-cadherin) and isogenic breast epithelial cells model (with or without E-cadherin)) and a xenograft tumor growth model with E-cadherin loss NUGC4 and MKN45 diffuse gastric cell lines. Cancers with an epithelial-mesenchymal transition (EMT), diffuse gastric cancer, and lobular breast cancer are similar in that E-cadherin is lost and/or downregulated. These findings indicate that RHOA dominant negative forms can be used as an effective therapy for DGC and lobular breast cancer as well as other cancers with the EMT phenotype.

INCORPORATION BY REFERENCE

The contents of all references, patent applications, patents, and published patent applications, as well as the Figures and the Sequence Listing, cited throughout this application are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method of treating a subject afflicted with cancer that has a reduced level of CDH1, comprising administering to the subject a therapeutically effective amount of at least one agent selected from the group consisting of 1) a nucleic acid encoding a RHOA dominant negative polypeptide encoding the sequence of SEQ ID NO: 1 and 2) a RHOA dominant negative polypeptide having the sequence of SEQ ID NO: 1.

2. The method of claim 1, wherein
   a) the cancer has a loss of CDH1 expression;
   b) the cancer is undergoing or has undergone epithelial to mesenchymal transition (EMT); and/or
   c) the cancer is selected from the group consisting of diffuse gastric cancer (DGC), lobular breast cancer, metastatic breast cancer, metastatic lung cancer, metastatic non small-cell lung cancer, colon cancer, pancreatic cancer, prostate cancer, brain cancer and melanoma.

3. The method of claim 1, wherein
   a) the agent comprises a RHOA dominant negative polypeptide sequence of SEQ ID NO: 1;
   b) the agent is a RHOA dominant negative polypeptide, and further comprises a heterologous polypeptide fused thereto, optionally wherein (i) the fused polypeptide has greater half-life and/or cell permeability than the corresponding unfused RHOA dominant negative polypeptide, or biologically active fragment thereof; and/or (ii) the heterologous polypeptide is an Fc domain and/or a cell permeable peptide; and/or
   c) the agent is a nucleic acid that is comprised within an expression vector or a cell.

4. The method of claim 1, further comprising administering to the subject an immunotherapy and/or cancer therapy, optionally wherein the immunotherapy and/or cancer therapy is administered before, after, or concurrently with the agent.

5. The method of claim 4, wherein
   a) the immunotherapy is cell-based;
   b) the immunotherapy comprises a cancer vaccine and/or virus;
   c) the immunotherapy inhibits an immune checkpoint, optionally wherein the immune checkpoint is selected from the group consisting of CTLA-4, PD-1, VISTA, B7-H2, B7-H3, PD-L1, B7-H4, B7-H6, ICOS, HVEM, PD-L2, CD160, gp49B, PIR-B, KIR family receptors, TIM-1, TIM-3, TIM-4, LAG-3, GITR, 4-IBB, OX-40, BTLA, SIRPalpha (CD47), CD48, 2B4 (CD244), B7.1, B7.2, ILT-2, ILT-4, TIGIT, HHLA2, butyrophilins, and A2aR; and/or
   d) the cancer therapy is selected from the group consisting of radiation, a radiosensitizer, and a chemotherapy.

6. The method of claim 1,
   a) wherein the agent reduces the number of viable or proliferating cells in the cancer, and/or reduces the volume or size of a tumor comprising the cancer cells;
   b) further comprising administering to the subject at least one additional therapeutic agent or regimen for treating the cancer;
   c) wherein the agent is administered in a pharmaceutically acceptable formulation;
   d) wherein the subject is an animal model of the cancer, optionally wherein the animal model is a mouse model; and/or
   e) wherein the subject is a mammal, optionally wherein the mammal is a mouse or human, optionally wherein the mammal is a human.

7. A method of reducing viability or proliferation of cancer cells which have a reduced level of CDH1, comprising contacting the cancer cells with at least one agent selected from the group consisting of 1) a nucleic acid encoding a RHOA dominant negative polypeptide encoding the sequence of SEQ ID NO: 1 and 2) a RHOA dominant negative polypeptide having the sequence of SEQ ID NO: 1.

8. The method of claim 7, wherein
   a) the cancer cells have a loss of CDH1 expression;
   b) the cancer cells are undergoing or have undergone epithelial to mesenchymal transition (EMT); and/or
   c) the cancer cells are obtained from a subject having a cancer selected from the group consisting of diffuse gastric cancer (DGC), lobular breast cancer, metastatic breast cancer, metastatic lung cancer, metastatic non small-cell lung cancer, colon cancer, pancreatic cancer, prostate cancer, brain cancer and melanoma.

9. The method of claim 7, wherein
a) the agent comprises a RHOA dominant negative polypeptide sequence of SEQ ID NO: 1;
b) the agent is a RHOA dominant negative polypeptide, and further comprises a heterologous polypeptide fused thereto, optionally wherein (i) the fused polypeptide has greater half-life and/or cell permeability than the corresponding unfused RHOA dominant negative polypeptide, or biologically active fragment thereof; and/or (ii) the heterologous polypeptide is an Fc domain and/or a cell permeable peptide; and/or
c) the agent is a nucleic acid that is comprised within an expression vector or a cell.

10. The method of claim 7, further comprising contacting the cancer cells with an immunotherapy and/or cancer therapy, optionally wherein the immunotherapy and/or cancer therapy is administered before, after, or concurrently with the agent.

11. The method of claim 10, wherein
a) the immunotherapy is cell-based;
b) the immunotherapy comprises a cancer vaccine and/or virus;
c) the immunotherapy inhibits an immune checkpoint, optionally wherein the immune checkpoint is selected from the group consisting of CTLA-4, PD-1, VISTA, B7-H2, B7-H3, PD-L1, B7-H4, B7-H6, ICOS, HVEM, PD-L2, CD160, gp49B, PIR-B, KIR family receptors, TIM-1, TIM-3, TIM-4, LAG-3, GITR, 4-IBB, OX-40, BTLA, SIRPalpha (CD47), CD48, 2B4 (CD244), B7.1, B7.2, ILT-2, ILT-4, TIGIT, HHLA2, butyrophilins, and A2aR; and/or
d) the cancer therapy is selected from the group consisting of radiation, a radiosensitizer, and a chemotherapy.

12. The method of claim 7, wherein
a) the agent is administered in a pharmaceutically acceptable formulation;
b) the step of contacting occurs in vivo, ex vivo, or in vitro;
c) the subject is an animal model of the cancer, optionally wherein the animal model is a mouse model; and/or
d) the subject is a mammal, optionally wherein the mammal is a mouse or human, optionally wherein the mammal is a human.

13. The method of claim 1, wherein the cancer is diffuse gastric cancer (DGC).

14. The method of claim 7, wherein the cancer cells are obtained from a subject having diffuse gastric cancer (DGC).

* * * * *

SEQUENCE LISTING

```
<160> NUMBER OF SEQ ID NOS: 12

<210> SEQ ID NO 1
<211> LENGTH: 193
<212> TYPE: PRT
<213> ORGANISM: Homo sapiens

<400> SEQUENCE: 1

Met Ala Ala Ile Arg Lys Lys Leu Val Ile Val Gly Asp Gly Ala Cys
1               5                   10                  15

Gly Lys Asn Cys Leu Leu Ile Val Phe Ser Lys Asp Gln Phe Pro Glu
            20                  25                  30

Val Tyr Val Pro Thr Val Phe Glu Asn Tyr Val Ala Asp Ile Glu Val
        35                  40                  45

Asp Gly Lys Gln Val Glu Leu Ala Leu Trp Asp Thr Ala Gly Gln Glu
    50                  55                  60

Asp Tyr Asp Arg Leu Arg Pro Leu Ser Tyr Pro Asp Thr Asp Val Ile
65                  70                  75                  80

Leu Met Cys Phe Ser Ile Asp Ser Pro Asp Ser Leu Glu Asn Ile Pro
                85                  90                  95

Glu Lys Trp Thr Pro Glu Val Lys His Phe Cys Pro Asn Val Pro Ile
            100                 105                 110

Ile Leu Val Gly Asn Lys Lys Asp Leu Arg Asn Asp Glu His Thr Arg
        115                 120                 125
```

```
Arg Glu Leu Ala Lys Met Lys Gln Glu Pro Val Lys Pro Glu Glu Gly
        130                 135                 140

Arg Asp Met Ala Asn Arg Ile Gly Ala Phe Gly Tyr Met Glu Cys Ser
145                 150                 155                 160

Ala Lys Thr Lys Asp Gly Val Arg Glu Val Phe Glu Met Ala Thr Arg
                165                 170                 175

Ala Ala Leu Gln Ala Arg Arg Gly Lys Lys Lys Ser Gly Cys Leu Val
                180                 185                 190

Leu

<210> SEQ ID NO 2
<211> LENGTH: 193
<212> TYPE: PRT
<213> ORGANISM: Homo sapiens

<400> SEQUENCE: 2

Met Ala Ala Ile Arg Lys Lys Leu Val Ile Val Gly Asp Gly Ala Cys
1               5                   10                  15

Val Lys Thr Cys Leu Leu Ile Val Phe Ser Lys Asp Gln Phe Pro Glu
                20                  25                  30

Val Tyr Val Pro Thr Val Phe Glu Asn Tyr Val Ala Asp Ile Glu Val
            35                  40                  45

Asp Gly Lys Gln Val Glu Leu Ala Leu Trp Asp Thr Ala Gly Gln Glu
        50                  55                  60

Asp Tyr Asp Arg Leu Arg Pro Leu Ser Tyr Pro Asp Thr Asp Val Ile
65                  70                  75                  80

Leu Met Cys Phe Ser Ile Asp Ser Pro Asp Ser Leu Glu Asn Ile Pro
                85                  90                  95

Glu Lys Trp Thr Pro Glu Val Lys His Phe Cys Pro Asn Val Pro Ile
                100                 105                 110

Ile Leu Val Gly Asn Lys Lys Asp Leu Arg Asn Asp Glu His Thr Arg
            115                 120                 125

Arg Glu Leu Ala Lys Met Lys Gln Glu Pro Val Lys Pro Glu Glu Gly
        130                 135                 140

Arg Asp Met Ala Asn Arg Ile Gly Ala Phe Gly Tyr Met Glu Cys Ser
145                 150                 155                 160

Ala Lys Thr Lys Asp Gly Val Arg Glu Val Phe Glu Met Ala Thr Arg
                165                 170                 175

Ala Ala Leu Gln Ala Arg Arg Gly Lys Lys Lys Ser Gly Cys Leu Val
                180                 185                 190

Leu

<210> SEQ ID NO 3
<211> LENGTH: 193
<212> TYPE: PRT
<213> ORGANISM: Homo sapiens

<400> SEQUENCE: 3

Met Ala Ala Ile Arg Lys Lys Leu Val Ile Val Gly Asp Gly Ala Cys
1               5                   10                  15

Glu Lys Thr Cys Leu Leu Ile Val Phe Ser Lys Asp Gln Phe Pro Glu
                20                  25                  30

Val Tyr Val Pro Thr Val Phe Glu Asn Tyr Val Ala Asp Ile Glu Val
            35                  40                  45

Asp Gly Lys Gln Val Glu Leu Ala Leu Trp Asp Thr Ala Gly Gln Glu
```

```
              50                  55                  60
Asp Tyr Asp Arg Leu Arg Pro Leu Ser Tyr Pro Asp Thr Asp Val Ile
 65                  70                  75                  80

Leu Met Cys Phe Ser Ile Asp Ser Pro Asp Ser Leu Glu Asn Ile Pro
                 85                  90                  95

Glu Lys Trp Thr Pro Glu Val Lys His Phe Cys Pro Asn Val Pro Ile
            100                 105                 110

Ile Leu Val Gly Asn Lys Lys Asp Leu Arg Asn Asp Glu His Thr Arg
                115                 120                 125

Arg Glu Leu Ala Lys Met Lys Gln Glu Pro Val Lys Pro Glu Glu Gly
        130                 135                 140

Arg Asp Met Ala Asn Arg Ile Gly Ala Phe Gly Tyr Met Glu Cys Ser
145                 150                 155                 160

Ala Lys Thr Lys Asp Gly Val Arg Glu Val Phe Glu Met Ala Thr Arg
                165                 170                 175

Ala Ala Leu Gln Ala Arg Arg Gly Lys Lys Lys Ser Gly Cys Leu Val
            180                 185                 190

Leu

<210> SEQ ID NO 4
<211> LENGTH: 582
<212> TYPE: DNA
<213> ORGANISM: Homo sapiens

<400> SEQUENCE: 4
atggctgcca tccggaagaa actggtgatt gttggtgatg agcctgtgg aaagaattgc      60 ttgctcatag tcttcagcaa ggaccagttc ccagaggtgt atgtgcccac agtgtttgag    120
aactatgtgg cagatatcga ggtggatgga aagcaggtag agttggcttt gtgggacaca    180
gctgggcagg aagattatga tcgcctgagg cccctctcct acccagatac cgatgttata    240
ctgatgtgtt tttccatcga cagccctgat agtttagaaa acatcccaga aaagtggacc    300
ccagaagtca gcatttctg tcccaacgtg cccatcatcc tggttgggaa taagaaggat    360
cttcggaatg atgagcacac aaggcgggag ctagccaaga tgaagcagga gccggtgaaa    420
cctgaagaag gcagagatat ggcaaacagg attggcgctt ttgggtacat ggagtgttca    480
gcaaagacca agatgggagt gagagaggtt tttgaaatgg ctacgagagc tgctctgcaa    540
gctagacgtg ggaagaaaaa atctgggtgc cttgtcttgt ga                      582

<210> SEQ ID NO 5
<211> LENGTH: 582
<212> TYPE: DNA
<213> ORGANISM: Homo sapiens

<400> SEQUENCE: 5
atggctgcca tccggaagaa actggtgatt gttggtgatg agcctgtgg aaagaactgc      60 ttgctcatag tcttcagcaa ggaccagttc ccagaggtgt atgtgcccac agtgtttgag    120
aactatgtgg cagatatcga ggtggatgga aagcaggtag agttggcttt gtgggacaca    180
gctgggcagg aagattatga tcgcctgagg cccctctcct acccagatac cgatgttata    240
ctgatgtgtt tttccatcga cagccctgat agtttagaaa acatcccaga aaagtggacc    300
ccagaagtca gcatttctg tcccaacgtg cccatcatcc tggttgggaa taagaaggat    360
cttcggaatg atgagcacac aaggcgggag ctagccaaga tgaagcagga gccggtgaaa    420
cctgaagaag gcagagatat ggcaaacagg attggcgctt ttgggtacat ggagtgttca    480
```

```
gcaaagacca aagatggagt gagagaggtt tttgaaatgg ctacgagagc tgctctgcaa      540
gctagacgtg ggaagaaaaa atctgggtgc cttgtcttgt ga                        582

<210> SEQ ID NO 6
<211> LENGTH: 582
<212> TYPE: DNA
<213> ORGANISM: Homo sapiens

<400> SEQUENCE: 6
atggctgcca tccggaagaa actggtgatt gttggtgatg agcctgtgt taagacatgc       60 ttgctcatag tcttcagcaa ggaccagttc ccagaggtgt atgtgcccac agtgtttgag     120
aactatgtgg cagatatcga ggtggatgga aagcaggtag agttggcttt gtgggacaca     180
gctgggcagg aagattatga tcgcctgagg cccctctcct acccagatac cgatgttata     240
ctgatgtgtt tttccatcga cagccctgat agtttagaaa acatcccaga aaagtggacc     300
ccagaagtca agcatttctg tcccaacgtg cccatcatcc tggttgggaa taagaaggat     360
cttcggaatg atgagcacac aaggcgggag ctagccaaga tgaagcagga gccggtgaaa     420
cctgaagaag gcagagatat ggcaaacagg attggcgctt tgggtacat ggagtgttca      480 gcaaagacca aagatggagt gagagaggtt tttgaaatgg ctacgagagc tgctctgcaa     540
gctagacgtg ggaagaaaaa atctgggtgc cttgtcttgt ga                        582

<210> SEQ ID NO 7
<211> LENGTH: 582
<212> TYPE: DNA
<213> ORGANISM: Homo sapiens

<400> SEQUENCE: 7
atggctgcca tccggaagaa actggtgatt gttggtgatg agcctgtgt caagacatgc       60 ttgctcatag tcttcagcaa ggaccagttc ccagaggtgt atgtgcccac agtgtttgag     120
aactatgtgg cagatatcga ggtggatgga aagcaggtag agttggcttt gtgggacaca     180
gctgggcagg aagattatga tcgcctgagg cccctctcct acccagatac cgatgttata     240
ctgatgtgtt tttccatcga cagccctgat agtttagaaa acatcccaga aaagtggacc     300
ccagaagtca agcatttctg tcccaacgtg cccatcatcc tggttgggaa taagaaggat     360
cttcggaatg atgagcacac aaggcgggag ctagccaaga tgaagcagga gccggtgaaa     420
cctgaagaag gcagagatat ggcaaacagg attggcgctt tgggtacat ggagtgttca      480 gcaaagacca aagatggagt gagagaggtt tttgaaatgg ctacgagagc tgctctgcaa     540
gctagacgtg ggaagaaaaa atctgggtgc cttgtcttgt ga                        582

<210> SEQ ID NO 8
<211> LENGTH: 582
<212> TYPE: DNA
<213> ORGANISM: Homo sapiens

<400> SEQUENCE: 8
atggctgcca tccggaagaa actggtgatt gttggtgatg agcctgtgt gaagacatgc       60 ttgctcatag tcttcagcaa ggaccagttc ccagaggtgt atgtgcccac agtgtttgag     120
aactatgtgg cagatatcga ggtggatgga aagcaggtag agttggcttt gtgggacaca     180
gctgggcagg aagattatga tcgcctgagg cccctctcct acccagatac cgatgttata     240
ctgatgtgtt tttccatcga cagccctgat agtttagaaa acatcccaga aaagtggacc     300
```

-continued

| ccagaagtca agcatttctg tcccaacgtg cccatcatcc tggttgggaa taagaaggat | 360 |
| cttcggaatg atgagcacac aaggcgggag ctagccaaga tgaagcagga gccggtgaaa | 420 |
| cctgaagaag gcagagatat ggcaaacagg attggcgctt ttgggtacat ggagtgttca | 480 |
| gcaaagacca aagatggagt gagagaggtt tttgaaatgg ctacgagagc tgctctgcaa | 540 |
| gctagacgtg ggaagaaaaa atctgggtgc cttgtcttgt ga | 582 |

<210> SEQ ID NO 9
<211> LENGTH: 582
<212> TYPE: DNA
<213> ORGANISM: Homo sapiens

<400> SEQUENCE: 9

| atggctgcca tccggaagaa actggtgatt gttggtgatg agcctgtgt aaagacatgc | 60 |
| ttgctcatag tcttcagcaa ggaccagttc ccagaggtgt atgtgcccac agtgtttgag | 120 |
| aactatgtgg cagatatcga ggtggatgga aagcaggtag agttggcttt gtgggacaca | 180 |
| gctgggcagg aagattatga tcgcctgagg cccctctcct acccagatac cgatgttata | 240 |
| ctgatgtgtt tttccatcga cagccctgat agtttagaaa acatcccaga aaagtggacc | 300 |
| ccagaagtca agcatttctg tcccaacgtg cccatcatcc tggttgggaa taagaaggat | 360 |
| cttcggaatg atgagcacac aaggcgggag ctagccaaga tgaagcagga gccggtgaaa | 420 |
| cctgaagaag gcagagatat ggcaaacagg attggcgctt ttgggtacat ggagtgttca | 480 |
| gcaaagacca aagatggagt gagagaggtt tttgaaatgg ctacgagagc tgctctgcaa | 540 |
| gctagacgtg ggaagaaaaa atctgggtgc cttgtcttgt ga | 582 |

<210> SEQ ID NO 10
<211> LENGTH: 582
<212> TYPE: DNA
<213> ORGANISM: Homo sapiens

<400> SEQUENCE: 10

| atggctgcca tccggaagaa actggtgatt gttggtgatg agcctgtga aaagacatgc | 60 |
| ttgctcatag tcttcagcaa ggaccagttc ccagaggtgt atgtgcccac agtgtttgag | 120 |
| aactatgtgg cagatatcga ggtggatgga aagcaggtag agttggcttt gtgggacaca | 180 |
| gctgggcagg aagattatga tcgcctgagg cccctctcct acccagatac cgatgttata | 240 |
| ctgatgtgtt tttccatcga cagccctgat agtttagaaa acatcccaga aaagtggacc | 300 |
| ccagaagtca agcatttctg tcccaacgtg cccatcatcc tggttgggaa taagaaggat | 360 |
| cttcggaatg atgagcacac aaggcgggag ctagccaaga tgaagcagga gccggtgaaa | 420 |
| cctgaagaag gcagagatat ggcaaacagg attggcgctt ttgggtacat ggagtgttca | 480 |
| gcaaagacca aagatggagt gagagaggtt tttgaaatgg ctacgagagc tgctctgcaa | 540 |
| gctagacgtg ggaagaaaaa atctgggtgc cttgtcttgt ga | 582 |

<210> SEQ ID NO 11
<211> LENGTH: 582
<212> TYPE: DNA
<213> ORGANISM: Homo sapiens

<400> SEQUENCE: 11

| atggctgcca tccggaagaa actggtgatt gttggtgatg agcctgtga gaagacatgc | 60 |
| ttgctcatag tcttcagcaa ggaccagttc ccagaggtgt atgtgcccac agtgtttgag | 120 |
| aactatgtgg cagatatcga ggtggatgga aagcaggtag agttggcttt gtgggacaca | 180 |

```
gctgggcagg aagattatga tcgcctgagg cccctctcct acccagatac cgatgttata    240
ctgatgtgtt tttccatcga cagccctgat agtttagaaa acatcccaga aaagtggacc    300
ccagaagtca agcatttctg tcccaacgtg cccatcatcc tggttgggaa taagaaggat    360
cttcggaatg atgagcacac aaggcgggag ctagccaaga tgaagcagga gccggtgaaa    420
cctgaagaag gcagagatat ggcaaacagg attggcgctt ttgggtacat ggagtgttca    480
gcaaagacca aagatggagt gagagaggtt tttgaaatgg ctacgagagc tgctctgcaa    540
gctagacgtg ggaagaaaaa atctgggtgc cttgtcttgt ga                      582

<210> SEQ ID NO 12
<211> LENGTH: 9
<212> TYPE: PRT
<213> ORGANISM: Artificial Sequence
<220> FEATURE:
<223> OTHER INFORMATION: /note="Description of Artificial Sequence:
      linker amino acid sequence"

<400> SEQUENCE: 12

Gly Gly Gly Gly Ala Gly Gly Gly Gly
1               5
```